(12) United States Patent
Ling

(10) Patent No.: US 11,963,677 B2
(45) Date of Patent: *Apr. 23, 2024

(54) FACIAL INVASIVE TISSUE TREATMENT METHOD

(71) Applicant: Xiaoqin Ling, Temple City, CA (US)

(72) Inventor: Xiaoqin Ling, Temple City, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 17/856,962

(22) Filed: Jul. 2, 2022

(65) Prior Publication Data

US 2023/0190265 A1 Jun. 22, 2023

Related U.S. Application Data

(63) Continuation of application No. 17/555,393, filed on Dec. 18, 2021, now Pat. No. 11,413,038.

(51) Int. Cl.
*A61B 17/06* (2006.01)
*A61B 90/00* (2016.01)
(Continued)

(52) U.S. Cl.
CPC .. *A61B 17/06166* (2013.01); *A61B 17/06066* (2013.01); *A61B 90/39* (2016.02); *A61B 2017/00792* (2013.01); *A61B 2017/0414* (2013.01); *A61B 2017/0464* (2013.01); *A61B 2017/06176* (2013.01); *A61B 2090/395* (2016.02)

(58) Field of Classification Search
CPC ........ A61B 17/06166; A61B 17/06066; A61B 2017/00792; A61B 2017/0414; A61B 2017/0464; A61B 2017/06176; A61B 2090/395

See application file for complete search history.

(56) References Cited

U.S. PATENT DOCUMENTS 7,513,904 B2 * 4/2009 Sulamanidze ... A61B 17/06166
606/224
9,033,999 B2 * 5/2015 Mueller ............. A61B 17/0482
606/139

(Continued)

*Primary Examiner* — Phong Son H Dang
(74) *Attorney, Agent, or Firm* — David & Raymond Patent Firm; Raymond Y Chan

(57) ABSTRACT

A facial invasive tissue treatment method includes the following procedures. Mark five to ten facelift suture path lines on each half face of a user in a predetermined pattern according to the facial condition of the user, wherein each facelift suture path line has an upper segment, a lower segment, and an insertion mark between the upper segment and the lower segment. After sterilization of the user's face, perform anesthesia at portions of the user's face where the needles inserting in and penetrating by injecting anesthetics at least at the insertion marks and the outlet marks of the facelift suture path lines marked on both half faces of the user. Thereafter, it is preferred to perform another sterilization to the user's face. Implant five to ten invasive sutures in the subcutaneous tissue layer of both half faces of the user along and underlying the facelift suture path lines marked thereon respectively. Perform facial shaping by tightening the underlying tissue through the implanted sutures while straddling, pushing, pressing, squeezing, shoving, extruding, and/or caressing the facial skin and tissue around the implanted sutures.

20 Claims, 38 Drawing Sheets

(51) Int. Cl.
　　　*A61B 17/00*　　　(2006.01)
　　　*A61B 17/04*　　　(2006.01)

(56) References Cited

U.S. PATENT DOCUMENTS

2011/0270304 A1* 11/2011 Lee .................. A61B 17/06166
　　　　　　　　　　　　　　　　　606/222
2014/0155913 A1* 6/2014 Kim ................... A61B 17/0469
　　　　　　　　　　　　　　　　　606/144
2021/0338236 A1* 11/2021 Greene ............ A61B 17/06166

* cited by examiner

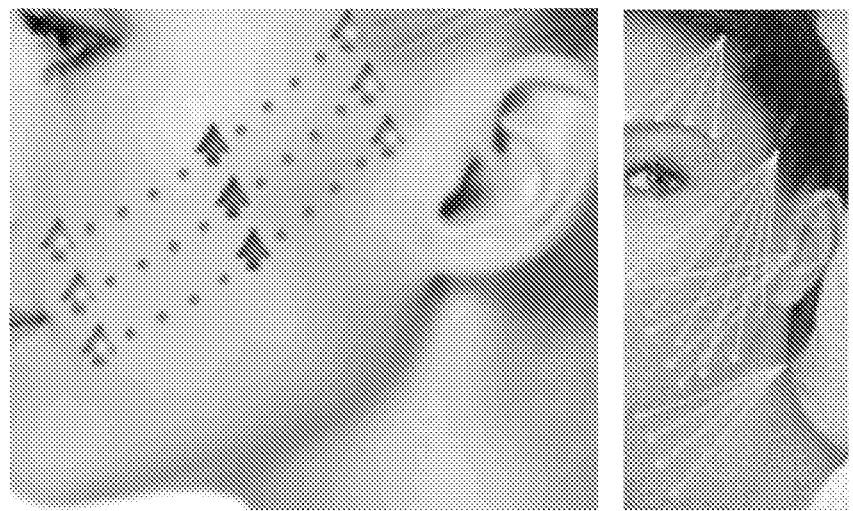
FIG. 5A
PRIOR ART
FIG. 5B
PRIOR ART
FIG. 6
PRIOR ART

FACIAL INVASIVE TISSUE TREATMENT METHOD

CROSS REFERENCE OF RELATED APPLICATION

This application is a Continuation application that claims the benefit of priority under 35U.S.C.§ 120 to a non-provisional application, application Ser. No. 17/555,393, filed Dec. 18, 2021, which is incorporated herewith by reference in its entirety.

BACKGROUND OF THE PRESENT INVENTION

Field of Invention

The present invention relates to facial tissue suspension and/or lifting treatment with suture assembly for tissue approximation, support, suspension, lifting and/or fixation, and more particularly to a three-dimensional facial invasive tissue treatment method with multiple invasive sutures each of which comprises an elongated flexible thread body supporting a plurality of frusto-conically shaped tissue engaging elements.

Description of Related Arts

Facial surgery or rhytidectomy such as cranial suspension has been used to reduce wrinkles and lift sagging facial tissue, wherein facial tissues are accessed via an incision before the ear and sutures are then used to lift the underlying tissue and repositioning sagging tissue of the face and neck. In order to minimize the invasion, non-surgical facelift such as minimally invasive tissue support system is used for facial structural shaping by means of suspension sutures, wherein an invasive suture assembly 10 including two elongated needles 11, 12, an elongated flexible thread body (thread) 13 supporting a plurality of frusto-conically shaped tissue engaging elements (cones) 14, which is a soft tissue anchor as shown in FIGS. 1 and 2, is used in supporting facial tissue by introducing the plurality of tissue engaging elements 14 into the facial soft tissue. U.S. Pat. No. 7,468,068 discloses a conventional suture for tissue support, suspension and fixation. U.S. Pat. No. 8,632,454 also discloses an application of such soft tissue anchor in minimally invasive tissue support system and method for supporting patient's breast or another tissue, wherein at least one inferior soft tissue anchor is introduced into a patient, such that at least one inferior tissue engaging element is suspended from the superior tissue engaging element.

FIGS. 3A to 3Y are schematic views from sinclairpharma.com illustrating a "Silhouette Soft®" reabsorbable suture (suture invasive assembly) comprising a plurality of frusto-conically shaped tissue engaging elements (cones) of Sinclair Pharmaceuticals Limited as an example of the above mentioned invasive suture assembly, wherein a pointed end of a first needle 11 is inserted into a subcutaneous layer of a facial skin of a patient (user) at a designated insertion position on the skin surface until the pointed end penetrates through the epidermis layer and the dermis layer under the skin for about three to five millimeters and is positioned in the subcutaneous tissue layer (FIG. 3A). Then, the first needle 11 is rotates for a predetermined angle to be inclined with respect to the facial skin surface (FIGS. 3B to 3D) to prepare for insertion of the first needle 11 into the subcutaneous tissue layer by extruding the adjacent facial skin to raise through the inclined first needle 11 (FIG. 3E). Continuously insert the first needle 11 into the subcutaneous tissue layer (FIGS. 3F and 3G), generally parallel to the subcutaneous tissue layer, and stab the pointed end of the first needle 11 out of the facial skin of the patient at another designated stab out position (FIGS. 3H to 3I) so as to pull the elongated flexible thread body (thread) 13 and a first section of the frusto-conically shaped tissue engaging elements (cones) 14 into the subcutaneous tissue layer (FIGS. 3J to 3K), wherein the narrow ends of the first section of tissue engaging elements 141 are directed to the first needle 11. Therefore, the first section of the plurality of tissue engaging elements (cones) 141 is distributed and extended between the insertion position and the stab out position within the subcutaneous tissue layer (FIG. 3L).

Thereafter, a pointed end of a second needle 12 in inserted into the subcutaneous tissue layer of the facial skin of the patient at the same designated insertion position of the first needle 11 preferably (FIG. 3M) on the skin surface until the pointed end of the second needle 12 penetrates through the stratum corneum layer and the pigment layer and is positioned in the subcutaneous tissue layer (FIG. 3N). Similarly, the second needle 12 is rotates for a predetermined angle to be inclined with respect to the facial skin surface (FIG. 3O) to prepare for insertion of the second needle 12 into the subcutaneous tissue layer by extruding the adjacent facial skin tissue to raise through the inclined second needle 12 (FIG. 3P). Then, continuously insert the second needle 12 into the subcutaneous tissue layer (FIGS. 3Q and 3R), generally parallel to the subcutaneous tissue layer, and stab the pointed end of the second needle 12 out of the facial skin of the patient at a second designated stab out position (FIGS. 3S to 3T) so as to pull the elongated flexible thread body 13 and a second section of frusto-conically shaped tissue engaging elements (cones) 142 into the subcutaneous tissue layer (FIG. 3U), wherein the narrow ends of the second segment of tissue engaging elements 142 are directed to the second needle 12. Therefore, by pulling a first end and a second end of the flexible thread body 13, the first and second sections of the plurality of tissue engaging elements (cones) 141, 142 are bidirectional and able to be entirely buried, distributed and extended within a treatment section of the subcutaneous tissue layer, i.e. between the first stab out position and the second stab out position (FIG. 3V).

The tension of the flexible thread body 13 and the distribution of the engaging elements 14 can be controlled by the gradually pulling either one or both the first and second ends of the flexible thread body 13. In other words, the buried tissue engaging elements 14 are substantially supported the suspended by the tissue of the treatment section of the subcutaneous tissue layer. The operator is then capable of performing further facial invasive tissue treatment by adjusting the tension of the flexible thread body 13, the positions of the tissue engaging elements (cones) through the facial skin tissue around the treatment section of the tissue engaging elements 14 in the subcutaneous tissue layer from the skin surface, as shown in FIGS. 3W-3Y, for facial operations and treatments such as tissue approximation, support, suspension, fixation, and etc.

Referring to FIG. 4, for example, the conventional method of a correct and efficient suture placement to correct sagging of the nasolabial crease is an invasive suture 10 comprising a plurality of frusto-conically shaped tissue engaging elements (cones) is positioned perpendicularly to lift tissue and reduce the nasolabial fold. To correct sagging of malar mound and jowl, two or more sutures are parallelly positioned to upwardly lift tissue as shown in FIG. 5A or inclinedly aligned to upwardly lift tissue as shown in FIG. 6.

Tissue lifting by single suture or parallel sutures is easier to operate but the result fails to provide a nature look since the facial wrinkles and sagging are occurred on a facial surface with a depth while the single suture or parallel sutures merely provide linear lift of facial tissue. Some professionals may perform a more complicated treatment with crossing sutures. As shown in FIG. 6, generally two to three sutures are invasively extended from jowls upwardly towards the ear as a first set of invasive sutures and another two to three invasive sutures are invasively extended from jowls upwardly towards the eyes as a second set of sutures, wherein the first set and second set of invasive sutures are intersecting in a crisscrossing manner. However, to drive crisscross lines on the face like FIG. 6 is easy but to operate multiple tissue engaging element intersecting with each other in the thin subcutaneous tissue layer is extremely complicated and difficult that may easy go wrong, and cause horror and tragic consequences as shown in FIGS. 7A-7C. Therefore, the conventional full treatment of suture facial lift is to place four to six invasive sutures in total in the subcutaneous tissue layer of a half face of the patient that greatly limits the possibility of achieving desired facial reshaping and lifting effect. However, the human facial skin is three-dimensional tissue that linear lifting through the invasive sutures, placement of just several invasive sutures is very different to provide even lifting and suspension three-dimensionally. How to place multiple invasive sutures in the subcutaneous tissue layer of the facial skin, especially comprising multiple frusto-conically shaped tissue engaging elements in the limited space and thickness of the subcutaneous tissue layer of the patient becomes a difficulty to the treatment in order to avoid any failure operation.

The aging processes of sagging are the main reasons of the skin of a person getting thinner that the thin skin develops wrinkles or volume loss. The skin of Asian is usually thicker than that of the westerners. Therefore, the sagging of skin due to aging, rather than wrinkling, is the major problem to be addressed for Asian skin. Generally, Asian skin is relatively large in area and thick that causes sagging and thus the facelifting technology by the Silhouetter Soft or Silhouetter Instalift sutures will be more effective to the Asian.

SUMMARY OF THE PRESENT INVENTION

The invention is advantageous in that it provides a facial invasive tissue treatment method for effective tissue suspension, tissue support and/or tissue fixation for lifting facial tissue, reducing wrinkles, lifting underlying tissue, repositioning sagging tissue, tissue suspension, and the like of the face and neck, wherein five to ten reabsorbable invasive sutures, each of which comprises an elongated flexible thread body supporting a plurality of frusto-conical shaped tissue engaging elements, are capable of placing and introducing in skin tissue, wherein the plurality of frusto-conical shaped tissue engaging elements are arranged and distributed in the subcutaneous tissue layer of each half face of a user in various arrangements for facial sagging correction of malar mound, nasojugal groove, palpebro-malar groove, mid-cheek groove, and jowl, wrinkles reduction such as nasolabial fold reduction, crow's foot wrinkles reduction, tissue suspension, face lifting and the like.

Another advantage of the invention is to provide a facial invasive tissue treatment method for placing five to ten reabsorable invasion sutures underlying skin tissue of each half face of a user in a three-dimensional manner so as to allow facial tissue reposition, suspension, supporting and/or lifting to provide a natural look.

Another advantage of the invention is to provide a facial invasive tissue treatment method for placing five to ten reabsorable invasion sutures underneath in the subcutaneous tissue layer of the facial skin tissue of each half face of a user in a such a manner that the invasion sutures are arranged in a three-dimensional intersecting and crossing layout.

Another advantage of the invention is to provide a facial invasive tissue treatment method for placing five to ten reabsorable invasion sutures in the subcutaneous tissue layer of the facial skin tissue of each half face of a user in a such a manner that one or more invasion sutures are arranged in a L-shaped layout.

Another advantage of the invention is to provide a facial invasive tissue treatment method for placing five to ten reabsorable invasion sutures underneath the facial skin tissue of each half face of a user, allowing facial reshaping operation through arranging and distributing two bidirectional sets of frusto-conically shaped tissue engaging elements along the flexible thread body to form an upper segment and a lower segment of each invasive suture introduced in the facial skin tissue in a three-dimensional manner.

Another advantage of the invention is to provide a facial invasive tissue treatment method for placing five to ten reabsorable invasion sutures underneath the facial skin tissue of each half face of a user in such a manner each invasive suture placed and introduced in the subcutaneous tissue layer of the skin tissue can be arranged to be supported through one or more other invasive sutures through the tension of the flexible thread body and/or the distribution of the frusto-conically shaped tissue engaging elements thereof.

Another advantage of the invention is to provide a facial invasive tissue treatment method that effectively reduces nasolabial fold.

Another advantage of the invention is to provide a facial invasive tissue treatment method that effectively corrects lip line and marionette line.

Another advantage of the invention is to provide a facial invasive tissue treatment method that effectively corrects crow's foot wrinkles, malar mound, nasojugal groove, palpebro-malar groove, and/or mid-cheek groove.

Another advantage of the invention is to provide a facial invasive tissue treatment method that effectively reshapes chin line, jawline and/or mouth line.

Additional advantages and features of the invention will become apparent from the description which follows and may be realized by means of the instrumentalities and combinations particular point out in the appended claims.

According to the present invention, the foregoing and other objects and advantages are attained by a facial invasive tissue treatment method comprising the following procedures:

(A) Mark five to ten facelift suture path lines on each half face of a user in a predetermined pattern according to the facial condition of the user, wherein each facelift suture path line has an upper segment, a lower segment, and an insertion mark between the upper segment and the lower segment.

(B) After sterilization of the user's face, at least perform anesthesia at portions of the user's face where the needles inserting in and penetrating by injecting anesthetics at least at the insertion marks and the outlet marks of the facelift suture path lines marked on both half faces of the user. Thereafter, it is preferred to perform another sterilization to the user's face.

(C) Implant five to ten invasive sutures in the subcutaneous tissue layer of each half face of the user along and underlying the facelift suture path lines marked thereon respectively.

(D) Perform facial shaping by tightening the underlying tissue through the implanted invasive sutures while straddling, pushing, pressing, squeezing, shoving, extruding, and/or caressing the facial skin and tissue around the implanted invasive sutures.

(E) Remove residual flexible thread body of the first segment and the second segment of each implanted invasive suture piercing out of the face of the user.

Before the procedure (D), the treatment method further comprises a procedure of removing the facelift suture path lines on the user's face.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 5A and FIG. 5B are schematic views illustrating conventional alignment of conventional sutures.

FIG. 6 is schematic view illustrating another conventional alignment of conventional sutures.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
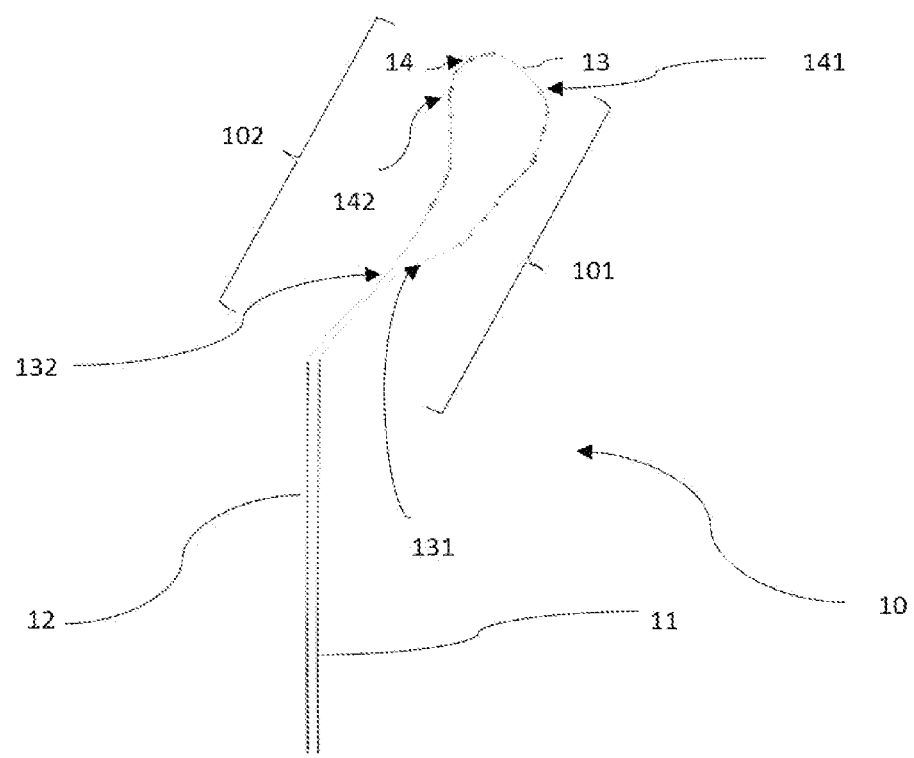
FIG. 1 is a perspective view illustrating a "Silhouette Soft" reabsorable invasive suture.
Figure 2:
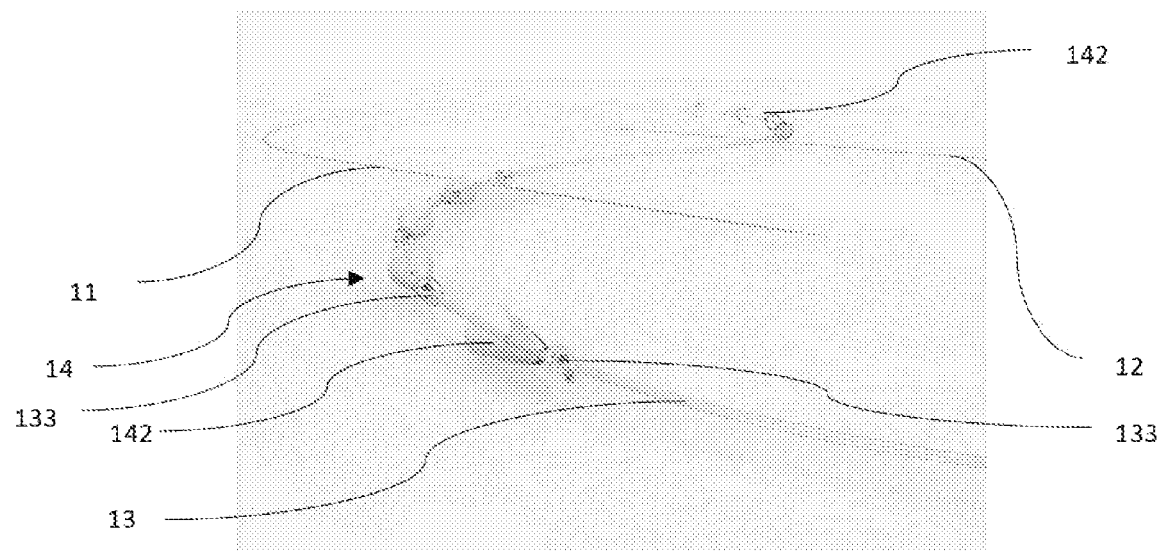
FIG. 2 is an enlarged perspective view of the "Silhouette Soft" invasive suture.

A facial invasive tissue treatment method according to a preferred embodiment is disclosed for implanting five to ten "Silhouette Soft" or "Silhouette Instalift" reabsorbable invasive sutures 10, as shown in FIGS. 1 and 2, in each half face of a user. The invasive suture 10 comprises a first needle 11 and a second needle 12, an elongated flexible thread body 13 which is extended between the first needle 11 and the second needle 12 and has a first segment 131 having a first length and a second segment 132 having a second length, a predetermined number of first frusto-conical shaped tissue engaging elements 141 being provided along the first segment 131 of the flexible thread body 13 and each having a smaller narrow end directing to the first needle 11 to form an upper segment of suture 101, and a predetermined number of second frusto-conical shaped tissue engaging elements 142 being provided along the second segment 132 of the flexible thread body 13 and each having a smaller narrow end directing to the second needle 12 to form a lower segment of suture 102. A plurality of thread nodes 133, each having a size smaller than a size of a conical opening end and larger than the smaller narrow end of the frusto-conical shaped tissue engaging element 14, is preferred to be provided before and after each of the first and second frusto-conical shaped tissue engaging elements 141, 142, wherein each frusto-conical shaped tissue engaging element 141, 142 is movable along the flexible thread body 13 between the adjacent front and rear thread nodes 133.

Figure 8:
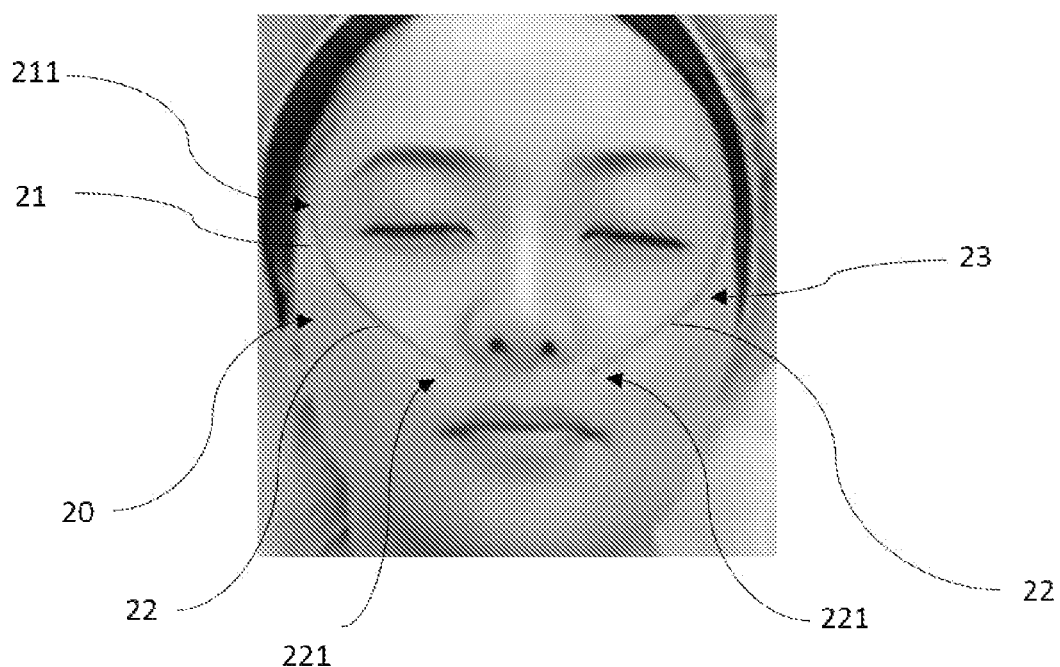
FIG. 8 is a schematic view illustrating a pair of facelift suture path lines respectively marked on a left half face and a right half face of a user according to a preferred embodiment of the present invention.
Figure 9:
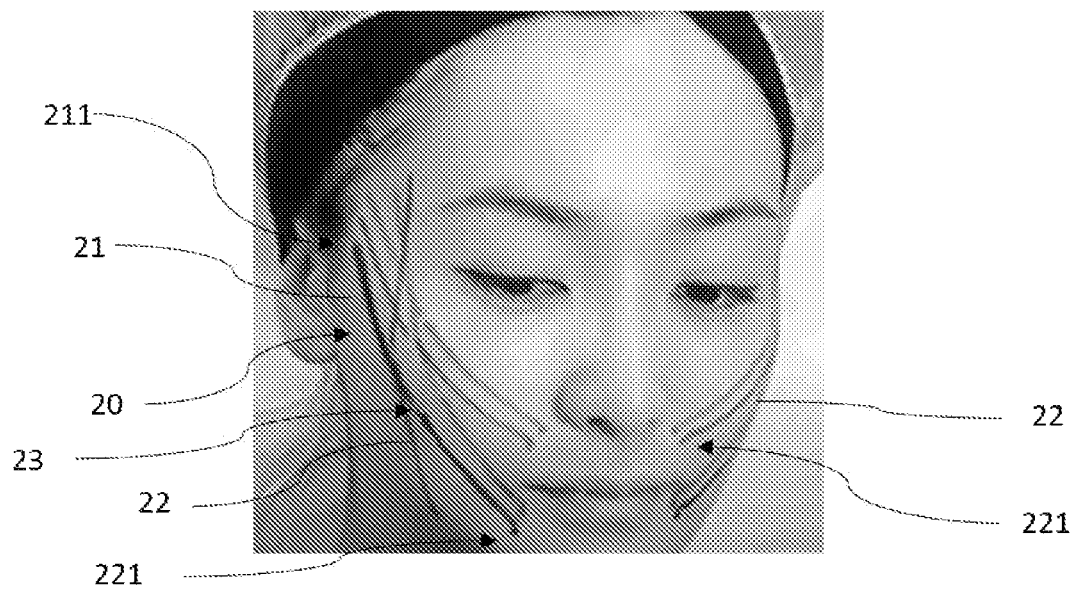
FIG. 9 is a schematic view illustrating an example set of five facelift suture path lines marked on each half face of the user according to the above preferred embodiment of the present invention.

The treatment method comprises the following procedures:

(A) Mark five to ten facelift suture path lines 20 on each of the left and right half faces of a user, referring to FIGS. 8-9 and FIGS. 16A-20D, in a predetermined pattern according to the facial and skin condition of the user as shown FIGS. 16A to 20D, wherein each facelift suture path line has an upper segment 21, a lower segment 22, and an insertion mark 23 between the upper segment 21 and the lower segment 22 (as shown in FIG. 8).

Figure 10:
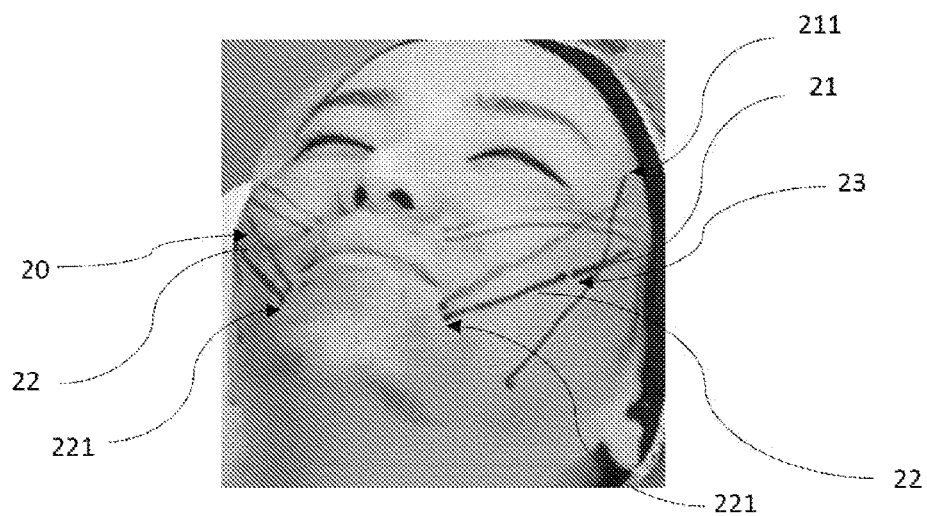
FIG. 10 is a schematic view illustrating the sterilization of the face of the user marked with a set of five facelift suture path lines according to the above preferred embodiment of the present invention.
Figures 11A, 11B, 11C:
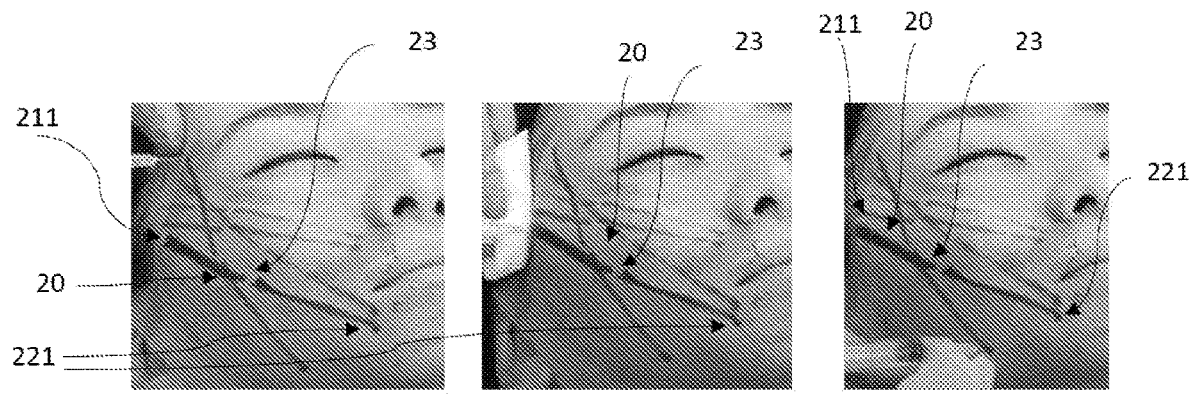
FIGS. 11A to 11E are schematic view illustrating the injection of anesthetics to the user's face according to the facelift suture path lines according to the above preferred embodiment of the present invention.
Figures 11D, 11E:
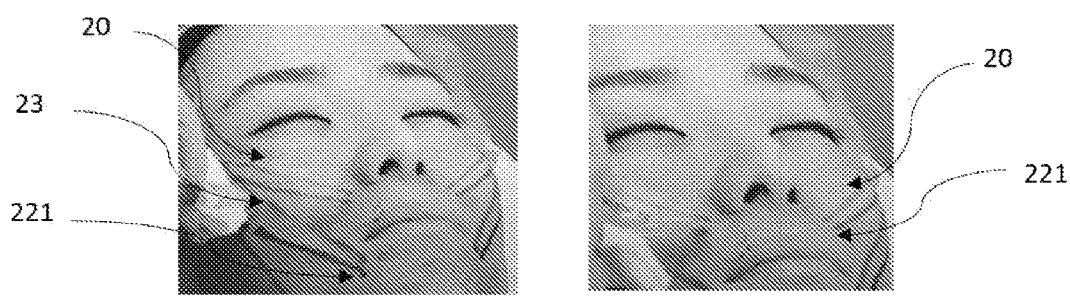

(B) After sterilization of the user's face as shown in FIG. 10, perform anesthesia to at least portions of the user's face where the needles 11, 12 (as shown in FIGS. 1 and 2) inserting in and penetrating by injecting anesthetics at least at the insertion marks 23 and the outlet marks 211, 221 of the facelift suture path lines 20 marked on both half faces of the user, as shown in FIGS. 11A to 11E. Thereafter, it is preferred to perform another sterilization to the user's face.

Figure 12A:
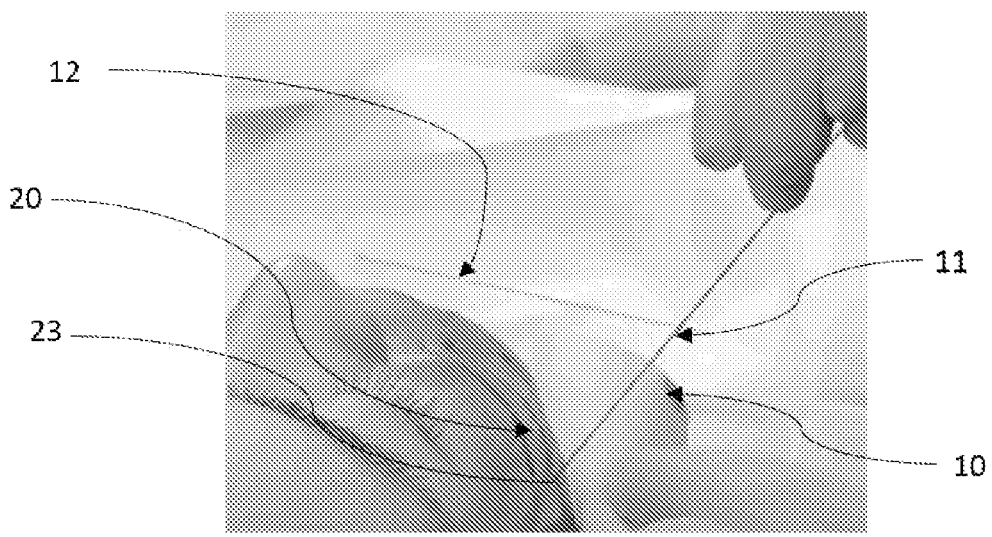
FIGS. 12A to 12T are schematic views illustrating the implant of invasive sutures according to the facelift suture path lines according to the above preferred embodiment of the present invention.
Figure 12B:
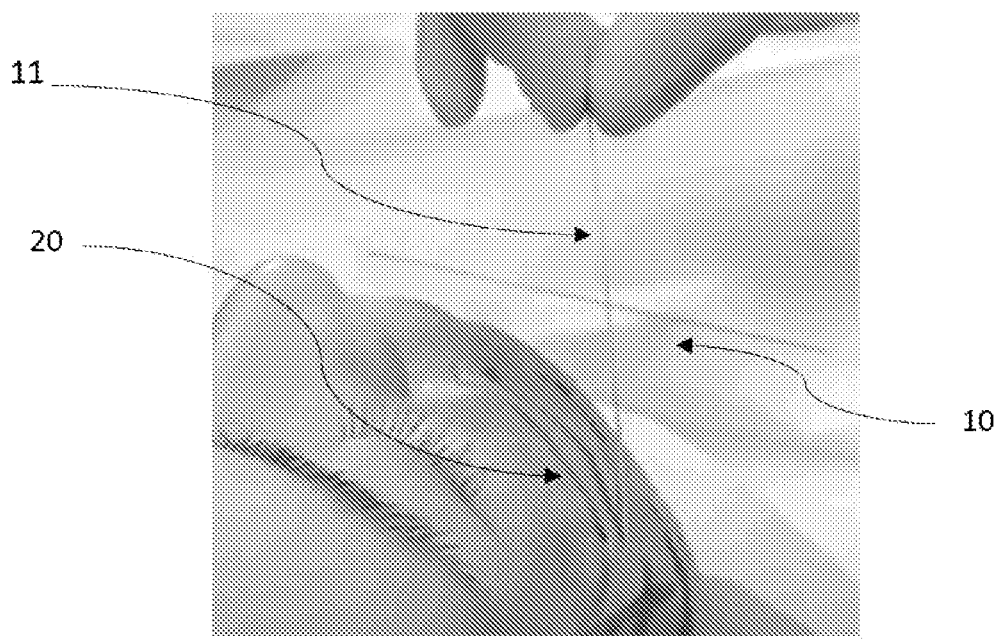
Figure 12C:
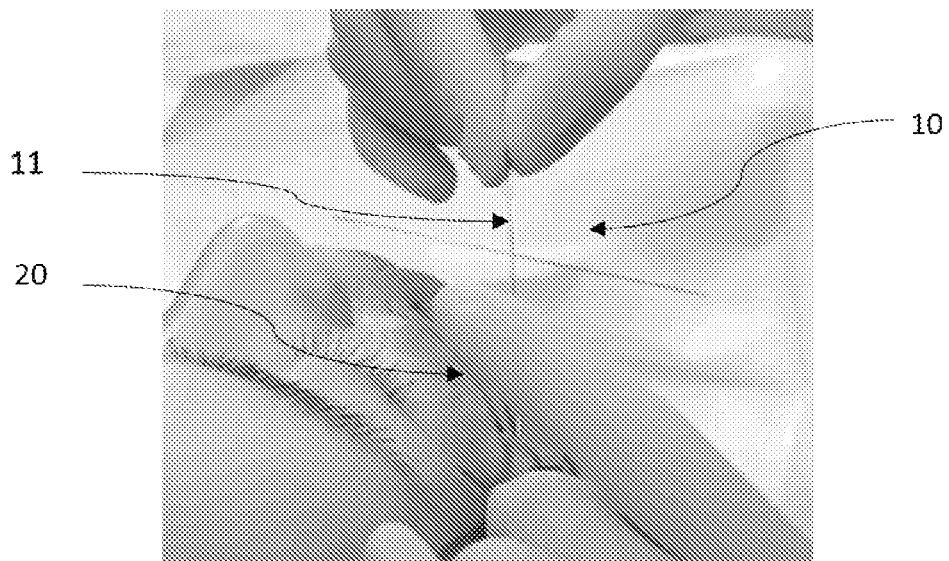
Figure 12D:
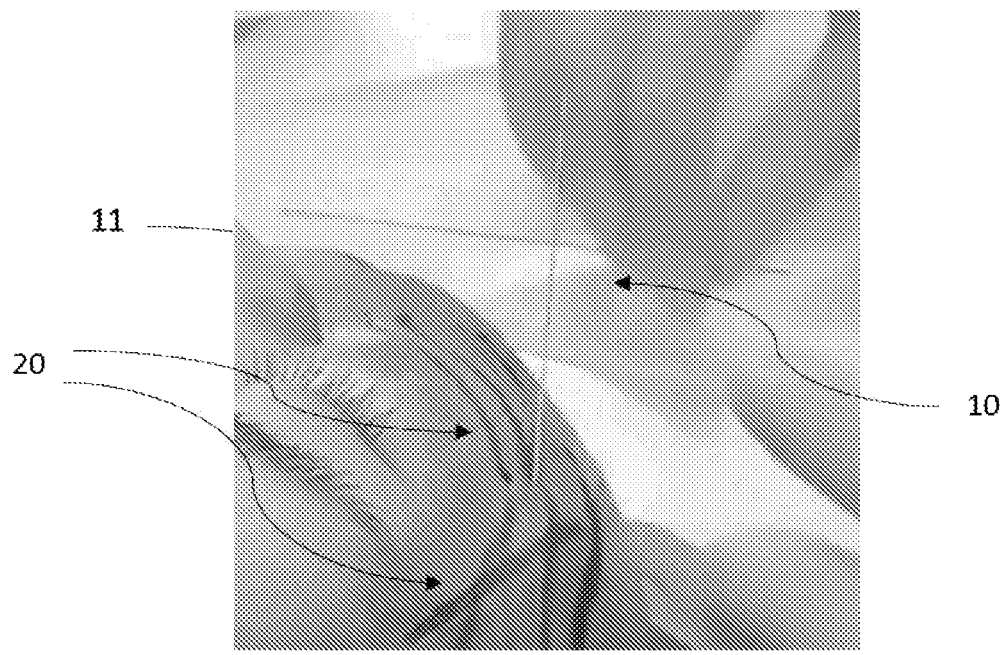
Figure 12E:
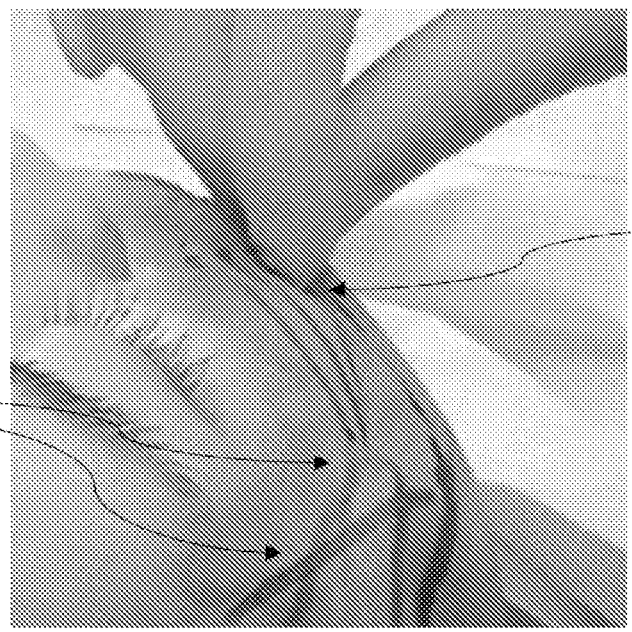
Figure 12F:
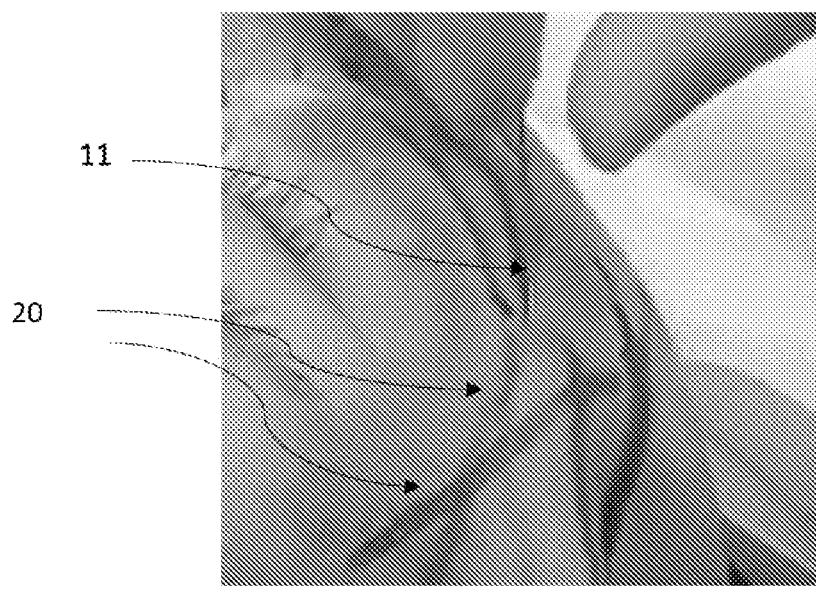
Figure 12G:
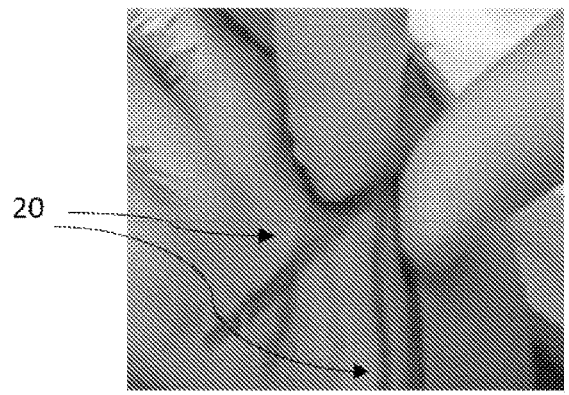
Figure 12H:
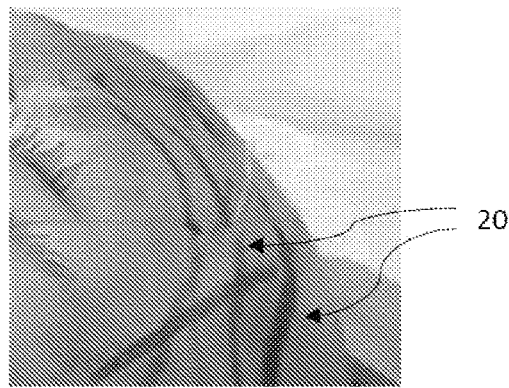
Figure 12I:
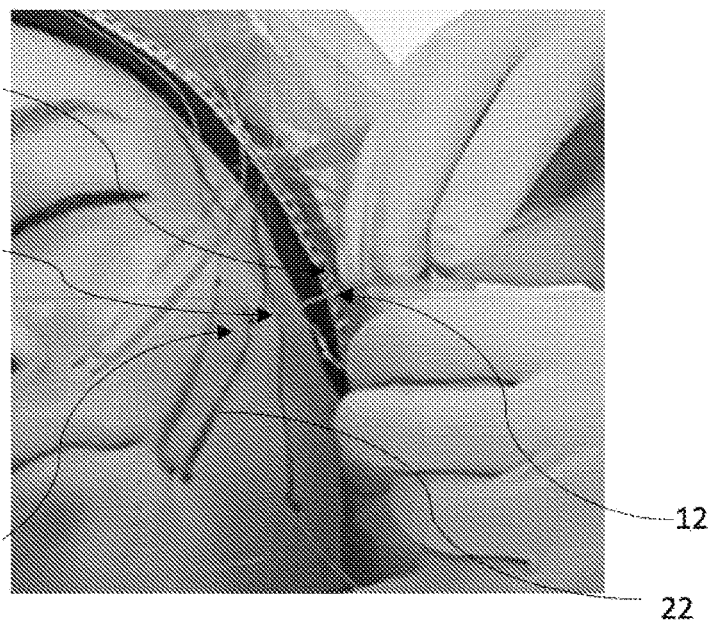
Figure 12J:
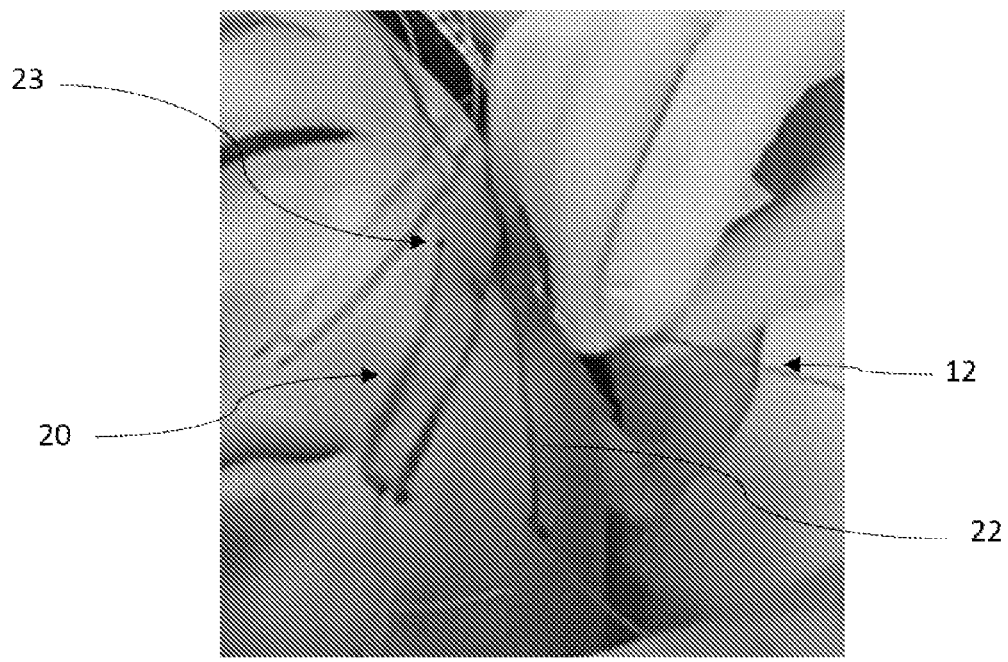
Figure 12K:
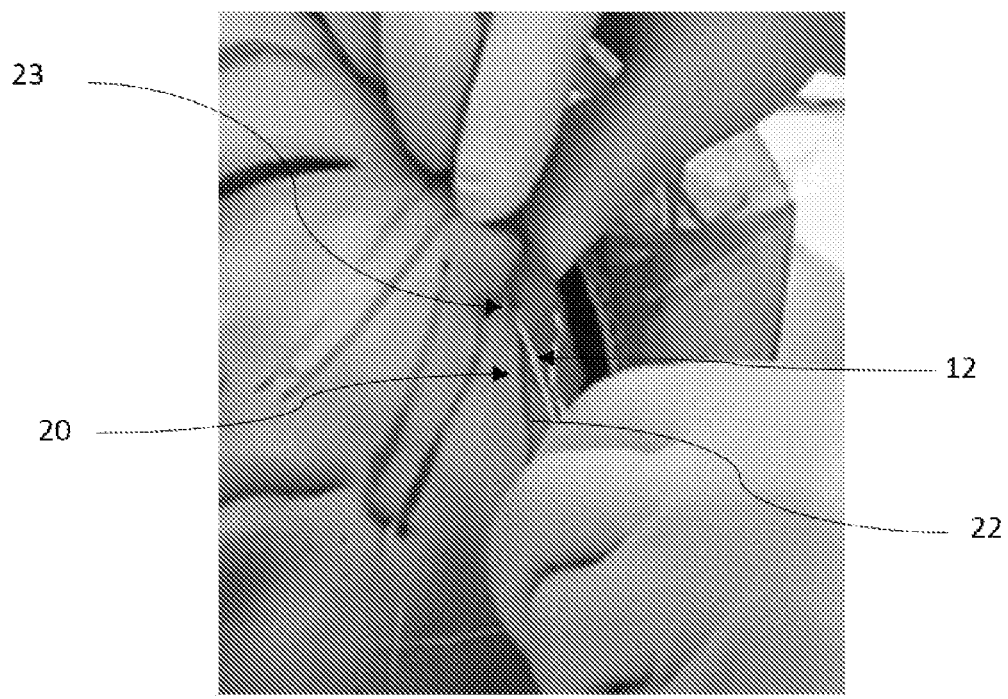
Figure 12L:
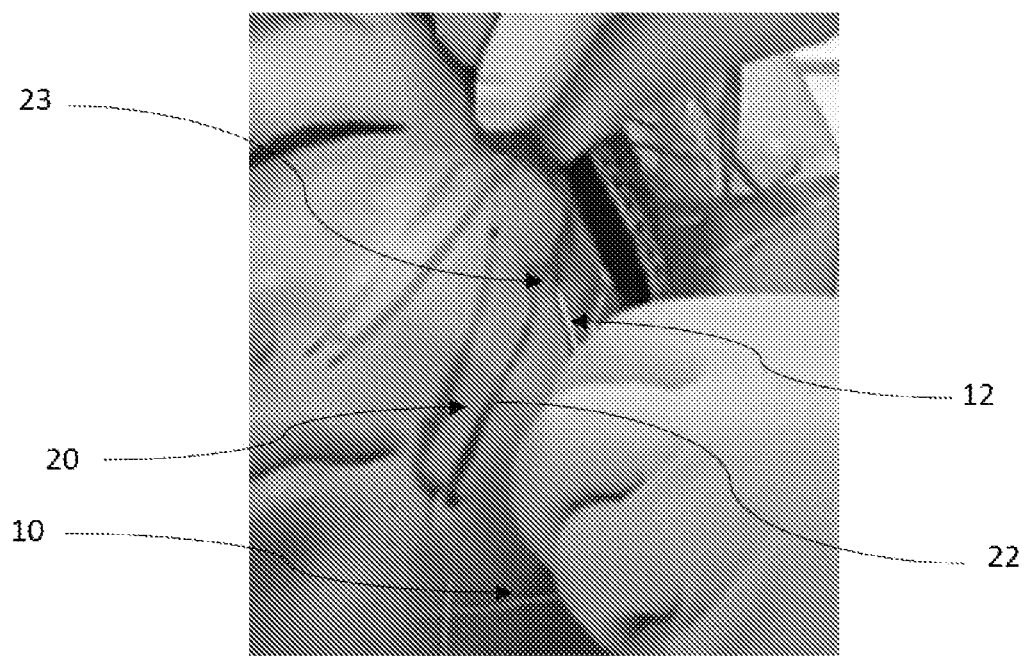
Figure 12M:
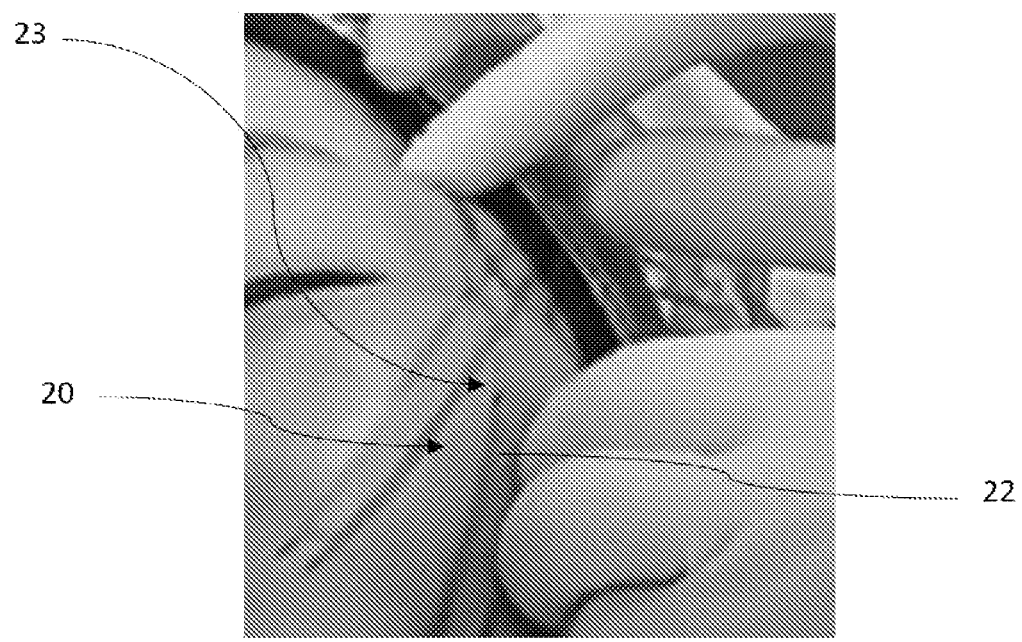
Figure 12N:
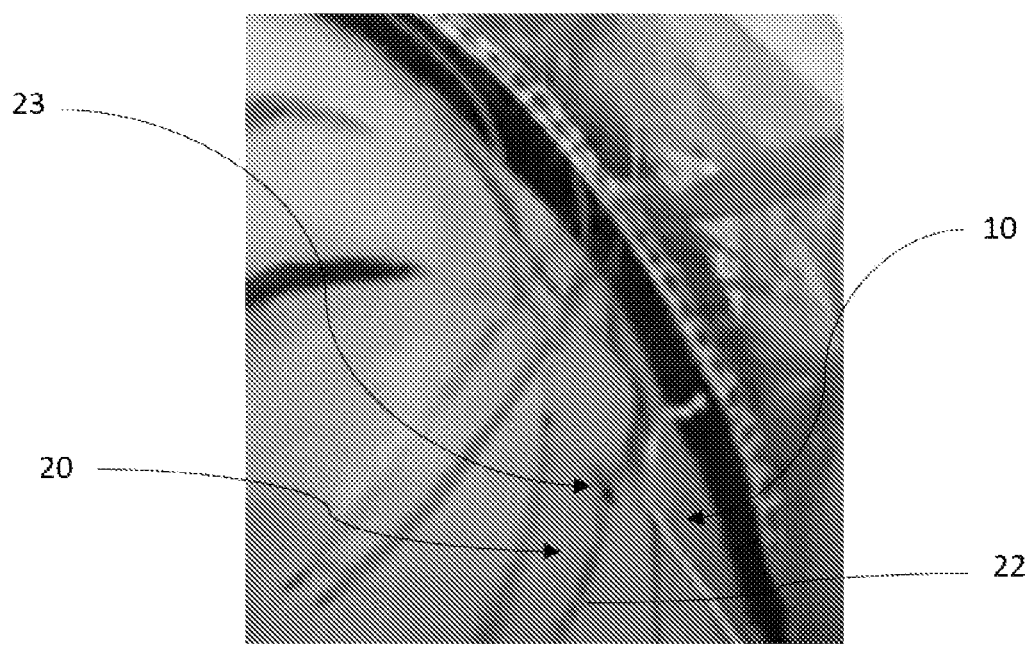
Figure 12O:
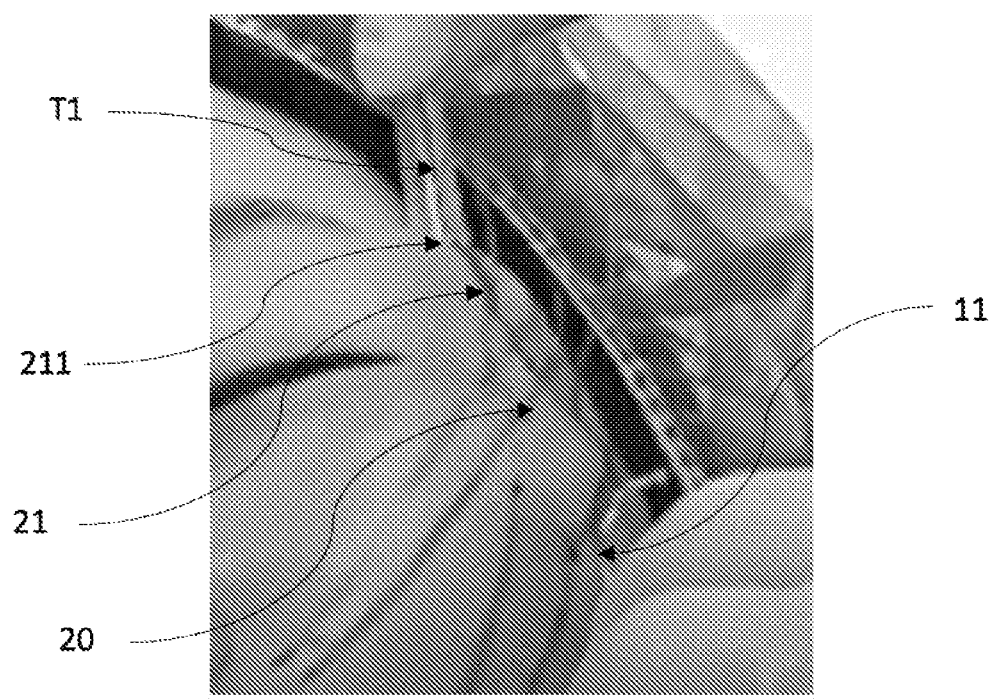
Figure 12P:
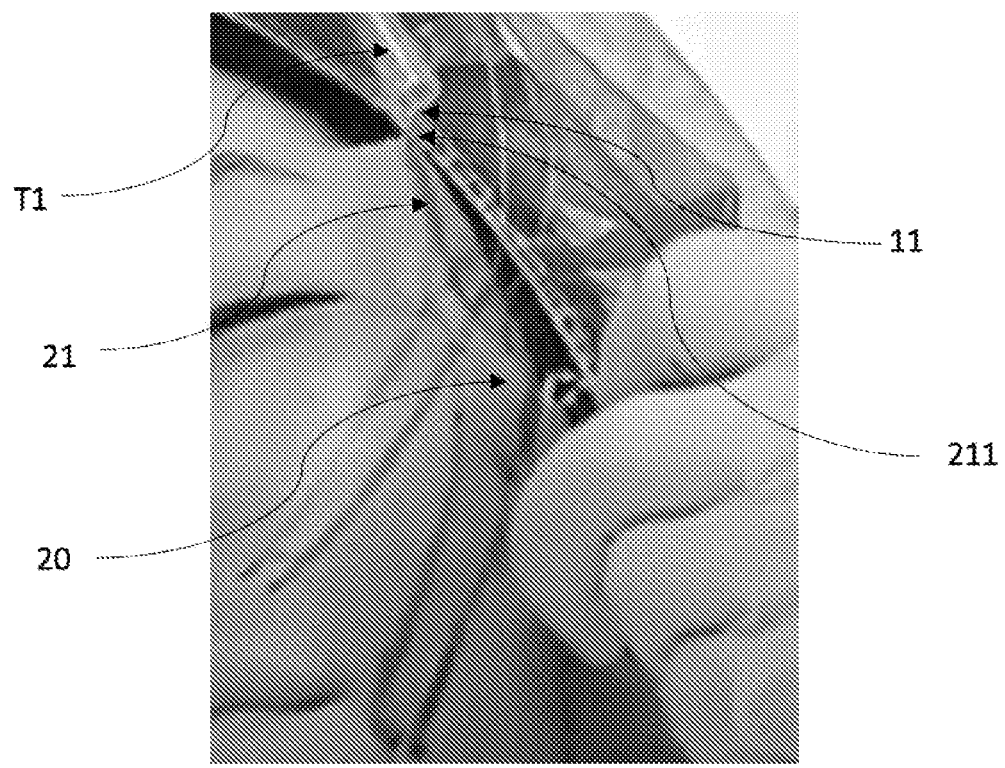
Figure 12Q:
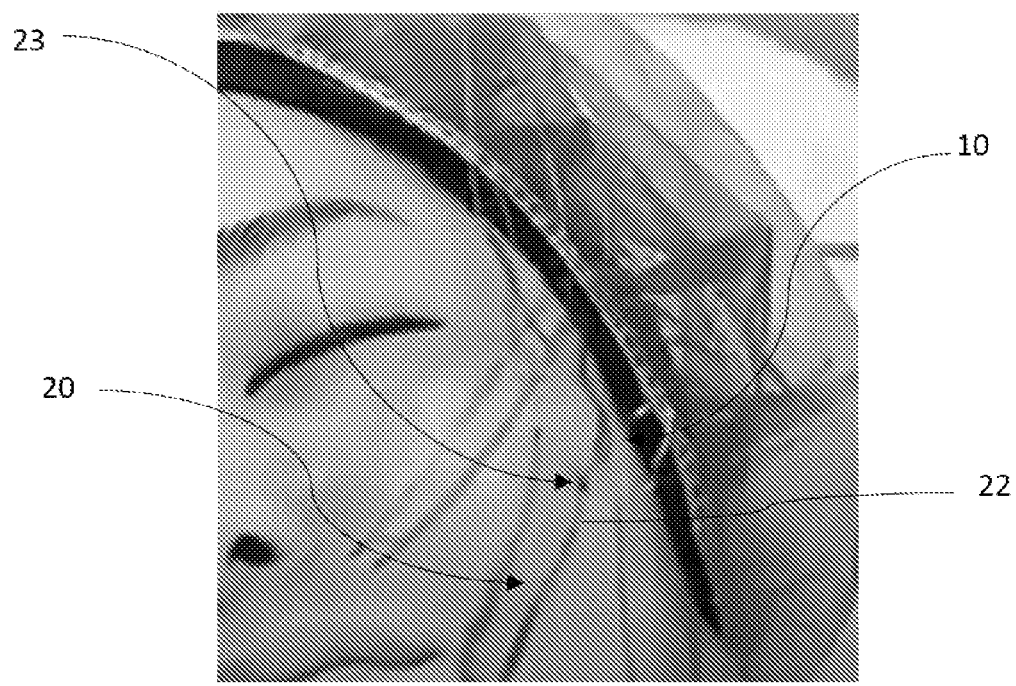
Figure 12R:
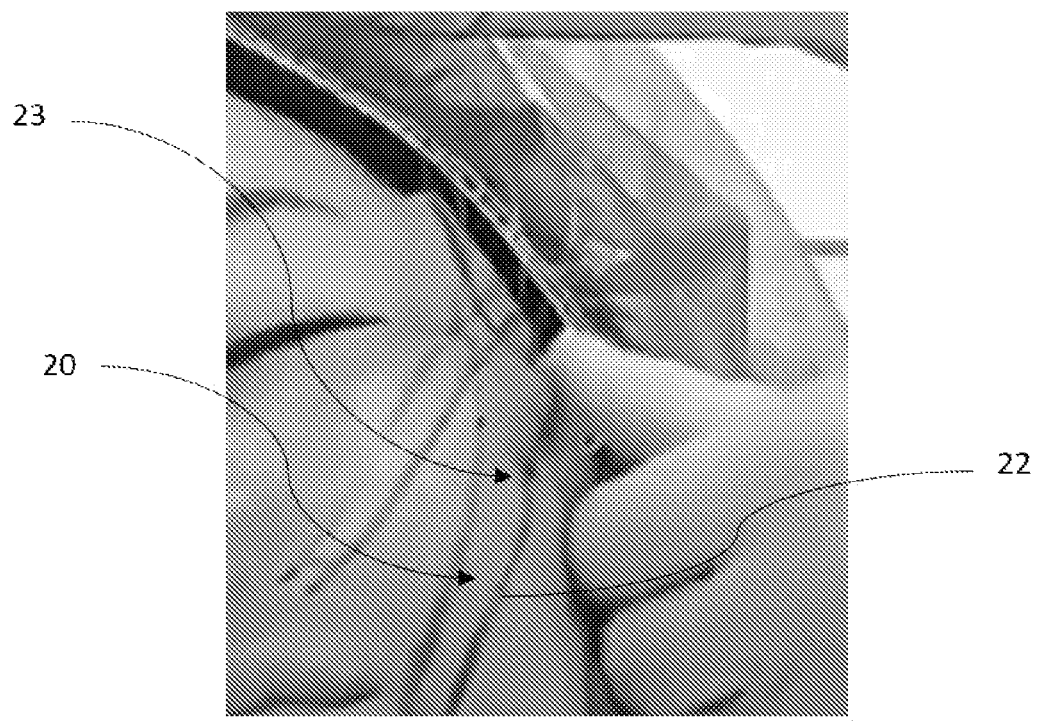
Figure 12S:
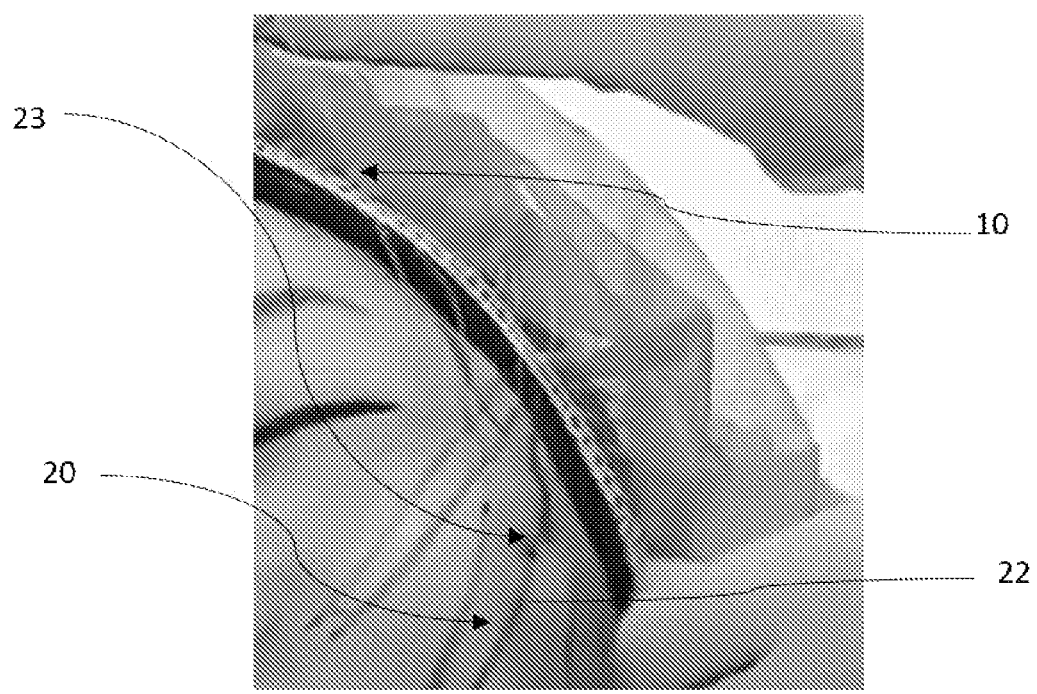
Figure 12T:

(C) Implant five to ten invasive sutures 10 in the subcutaneous tissue layer of each half face of the user along and underlying the facelift suture path lines 20 marked thereon respectively, as shown in FIGS. 12A to 12T.

(D) Perform facial shaping through tightening the underlying tissue by the implanted sutures while straddling, pushing, pressing, squeezing, shoving, extruding, and/or caressing the facial skin and tissue around the implanted sutures, as shown in FIGS. 14A to 14H.

Figures 15A, 15B:
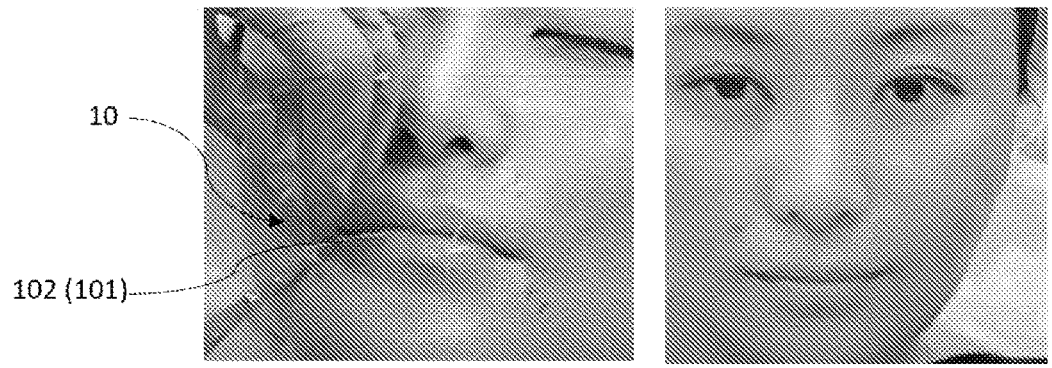
FIGS. 15A to 15B are schematic views illustrating the removal of the residual flexible thread bodies of the invasive sutures piercing out of the user's face according to the above preferred embodiment of the present invention.

(E) Remove residual flexible thread bodies of the first segment 101 and the second segment 102 of each implanted suture 10 piercing out of the face of the user, as shown in FIGS. 15A and 15B.

Figure 13:
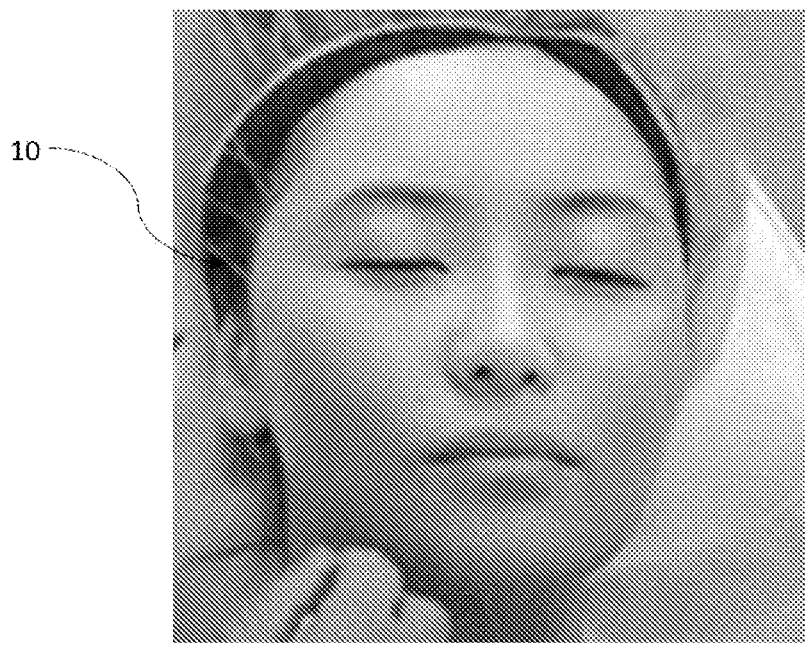
FIG. 13 is a schematic view illustrating the user's face after removal of the facelift suture path lines on the user's face according to the above preferred embodiment of the present invention.

Before the procedure (D), the treatment method further comprises a procedure of removing the facelift suture path lines 20 on the user's face, as shown in FIG. 13.

The procedure (A) further comprises marking an upper outlet mark 211 at an upper end of the upper segment 21 and a lower outlet mark 221 at a lower end of the lower segment 22 while the insertion mark 23 is positioned between a lower end of the upper segment 21 and an upper end of the lower segment 23. Each of the outlet marks 211, 221 can be the upper end of the upper segment 21 and the lower end of the lower segment 22 respectively or an enlarged mark formed at each end of the upper segment 21 and the lower segment 22. The facelift suture path lines 10 are marked by one or more colored marker pens, wherein it is preferred that each type of the facelift suture path lines 20 on each half face is marked with different color. A flexible marker ruler may be used to help the marking of the upper segment 21 and lower segment 22 of the facelift suture path line 20 to match the length of the first segment 131 and the second segment 132 of the flexible thread body 13 of the kind of suture 10 (as shown in FIG. 1) to be used.

According to the preferred embodiment, referring to FIG. 8, the insertion mark 23 is embodied as a space left blank between the lower end of the upper segment 21 and the upper end of the lower segment 22 while the outlet marks 211 and 221 of the upper segment 21 and lower segment 22 are embodied as thicker dot mark.

Figure 22:
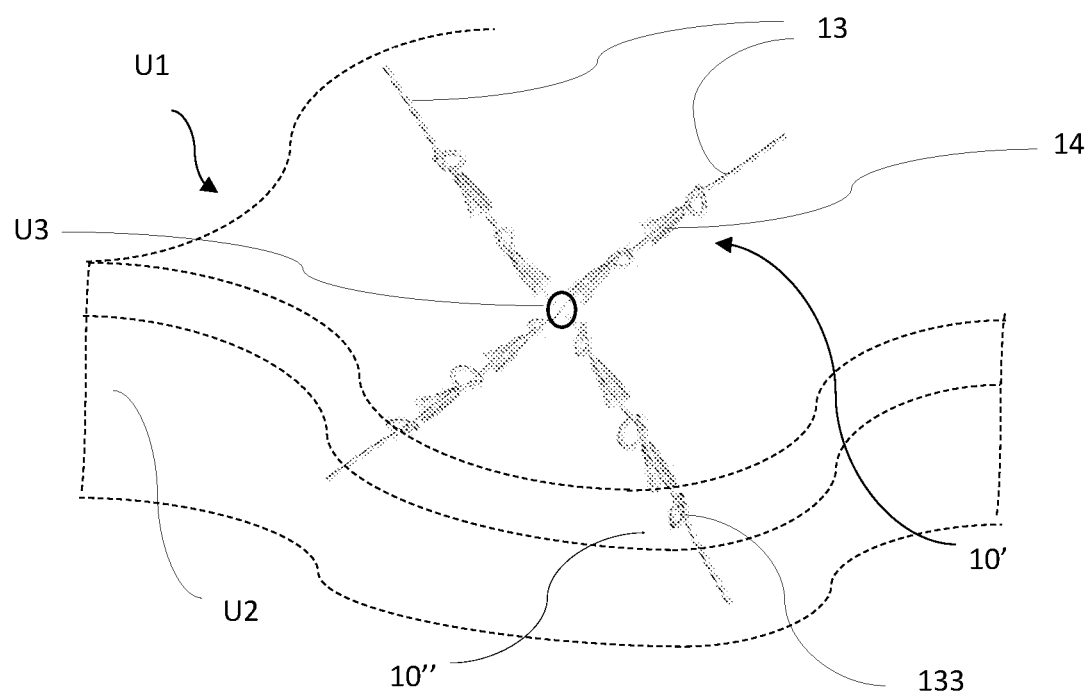
FIG. 22 is a perspective schematic view illustrating the arrangement of two intersecting invasive sutures in the subcutaneous tissue layer of the user's skin according to the preferred embodiment of the present invention.

It is worth mentioning that multiple conventional sutures which merely comprise elongated reaborabable flexible threads without cones (frusto-conically shaped tissue engaging elements) are easily to be implanted and crossing with each other in the subcutaneous tissue layer of the skin, even contacting with each other, as shown in FIGS. 5A to 6, wherein the conventional sutures can be aligned parallelly as shown in FIG. 5A, grouped inclinedly to have one end of each suture together as combined pulling point so as to pull the bundle of sutures upwards to shape the portion of face implanted with the group of inclined sutures as shown in FIG. 5B, or aligned crossing to form a grid of sutures to shape the user's face as shown in FIG. 6. However, for invasive suture 10 such as "Silhouette Soft" or "Silhouette Lift", generally four to six frusto-conical shaped tissue engaging elements 142 are movably mounted along each of the first segment 131 and the second segment 132 of the thread body 13 (as shown in FIG. 1). It is difficult to align invasive sutures 10 in an intersecting and overlapping manner as shown in FIG. 6 and FIG. 22. Therefore, the maximum number "Sihouette Soft" or "Sihouette Intralift" invasive sutures to be implanted is six and aligned in generally parallel manner traditionally. In addition, it is even more difficult to place and introduce the "Sihouette Soft", "Sihouette Intralift" or the like sutures as shown in FIGS. 1 and 2 in the V bundle arrangements intersecting with each other, as shown in FIG. 5B for failing to overlapping the tissue engaging elements 14 in the thin subcutaneous tissue layer of the skin tissue without contacting with each other.

The present invention provides an innovative treatment method for placing the "Sihouette Soft", "Sihouette Intralift" or the like sutures as many as five to ten in haft face of a user in such a way that forms an effective suspension and lifting layout and arrangement to efficiently enable the operator, such as a physician, plastic surgeon, beautician, and etc., to perform facelifting and facial shaping in multiple directions effectively and efficiently for various needs, situations and treatments. It is noted that, in order to enable the operator to perform a more flexible and effective treatment to the skin tissue of the user, the layout and arrangement of the invasive sutures implanted in the facial skin tissue are preferred to be as many as possible so as to corelate with each face portion that needs to be reshaped through different lifting and tightening levels and orders of the implant invasive sutures. Simply speaking, it likes the construction of a cement or concrete structure, the more complicated and pressure supporting portion of the structure needs, the more reinforcing rebars or steel bars are arranged in a crossing, intersecting, and overlapping manner in that portion. The sagging skin portion prefers to have more support, suspension and/or lifting through the effective arrangement of invasive sutures in a three-dimensional manner.

Face suspension and lifting treatment with invasive sutures generally applies at least for:

(i) preventive treatment that the aging sagging is relatively mild;

(ii) anti-aging treatment for whose marionette folds and patterns, nasolabial folds and patterns, more severe aging sagging of facial tissue such as apple muscles and etc., and infant hypertrophy, and the like;

(iii) treatment for tighter and plumper face while lifting the face; and (iv) treatment for user having large face plate.

Figure 4:
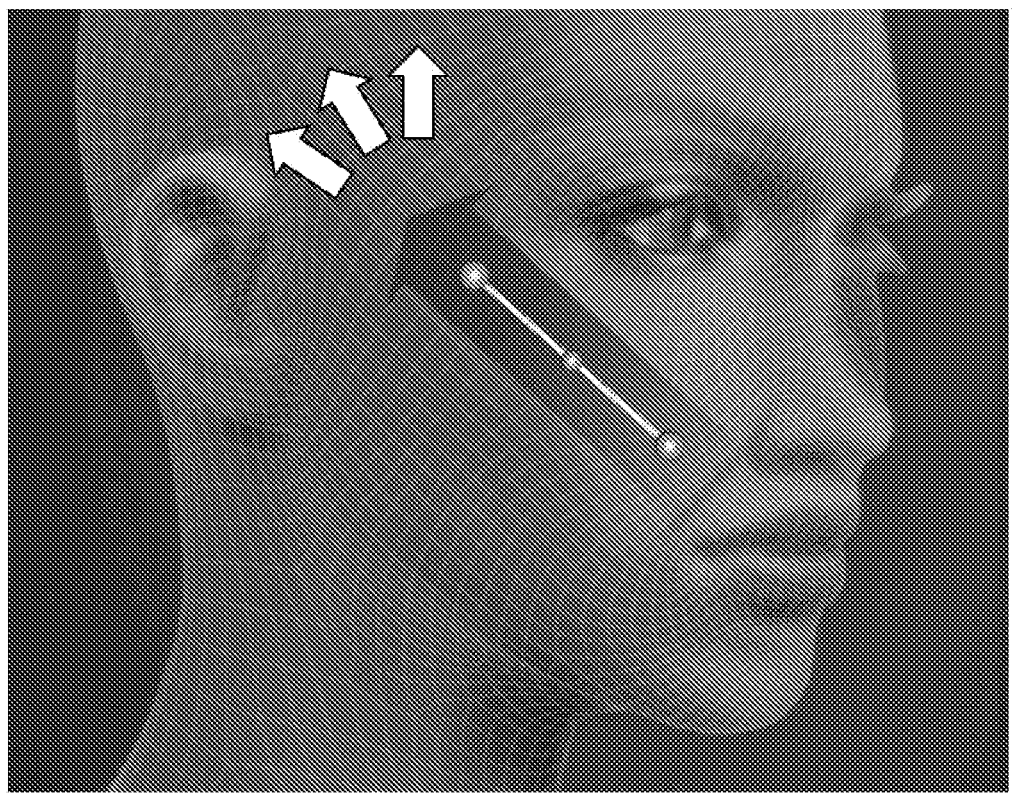
FIG. 4 is a schematic view illustrating the alignment of a suture in half face of a user.
Figure 7A:
FIG. 7A to FIG. 7C are schematic views illustrating common failures of conventional suture implant.
Figure 7B:
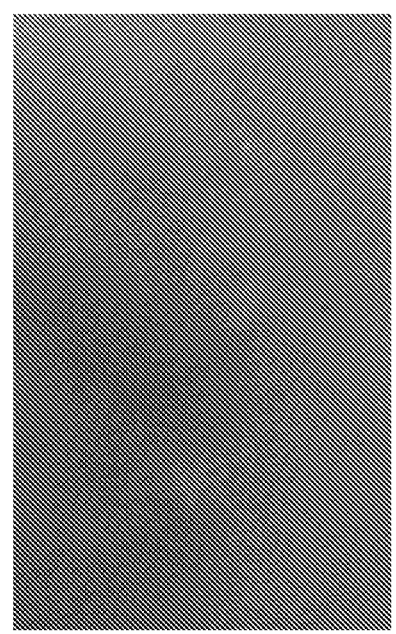
Figure 7C:

Along with the aging of a person, wrinkles slowly appear, such as nasolabial (nose to mouth) lines or folds, crows feet, bunny lines, frown lines, marionette (mouth to chin) lines or folds, and etc., and sagging occurs at the brow, under eyes, mid-face, cheeks, jawline, apple muscles, apple chin, and/or malar mound portions of the user's face. Suspension and lifting of facial tissue towards an upward and rearward directions as shown in FIG. 4 substantially and effectively reduce the folds and fine lines, eye bags, and crows feet, and lift eye brows, cheeks, apple muscles, jawline and jowls due to aging sagging. The problem is how to suspend and lift the facial tissue through as many invasive sutures as possible. The present invention significantly provides effective suture implant technique and suture layout arrangement for the above treatments.

For preventive treatment, since the aging sagging is relatively mild, five invasive sutures 10 are implanted in each half face of the user as illustrated in FIGS. 9 to 15B, including a pair of front facelift sutures 10, a pair mid facelift sutures 10, and one side facelift suture 10. Correspondingly, in procedure (A), a pair of front facelift suture path lines 20A, a pair of mid facelift suture path lines 20B, one side facelift suture path line 20C are marked on the user's half face with assistance of the marker ruler, as shown in FIG. 16A.

Figure 16A:
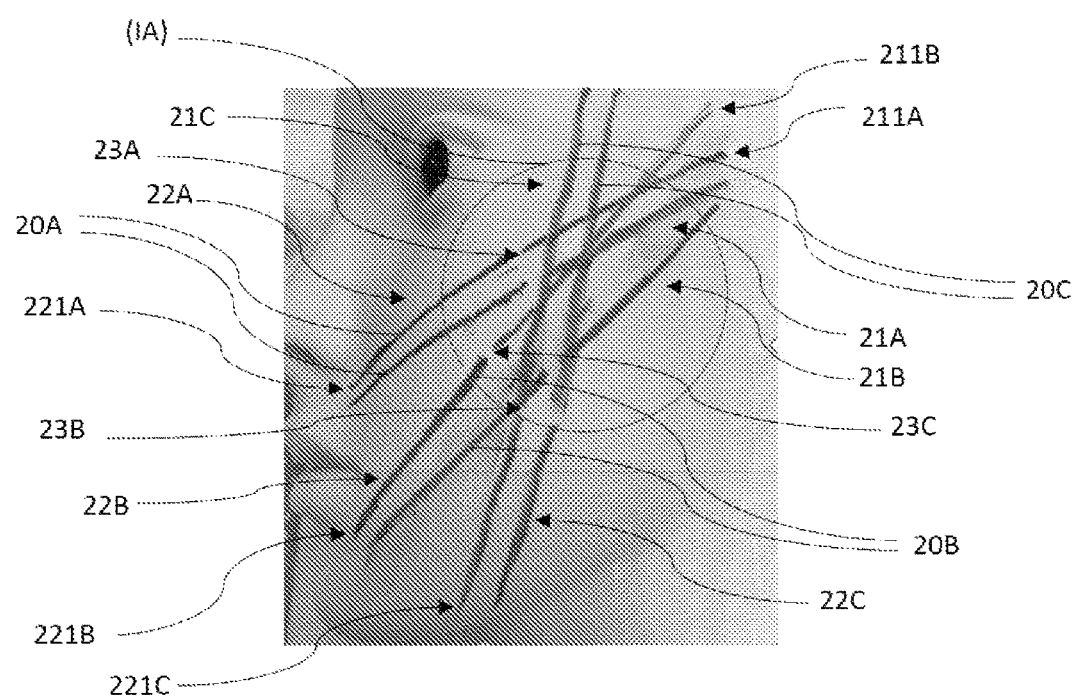
FIGS. 16A to 16C are schematic views illustrating patterns of marking layout and arrangement of six facelift suture path lines on each half face of a user according to the preferred embodiment of the present invention.
Figure 16B:
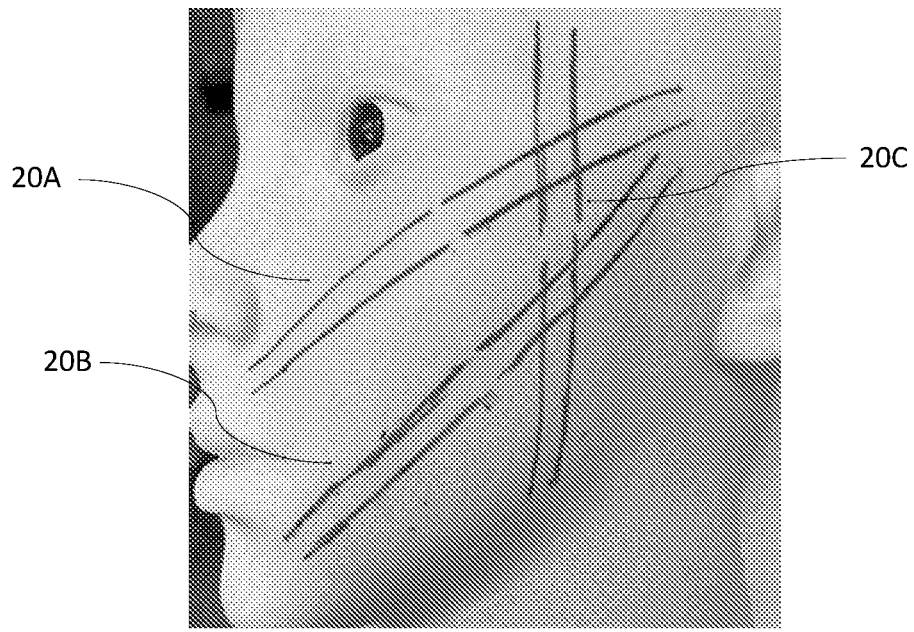
Figure 16C:
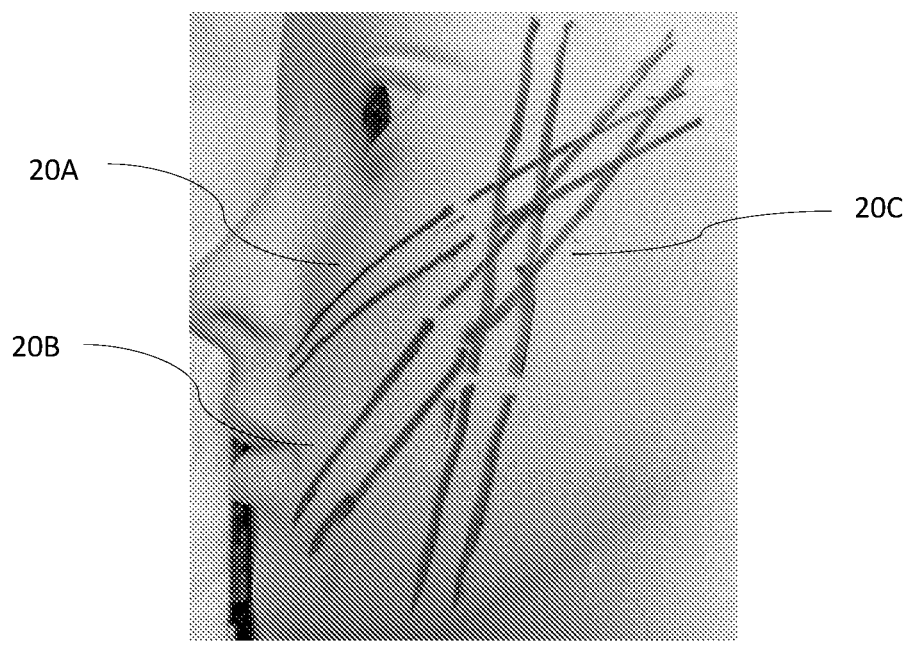

Or, alternatively, three pairs of invasive sutures 10 are implanted in each half face of the user, referring to FIGS. 16A to 16C, including a pair of front facelift sutures 10, a pair of mid facelift sutures 10 and a pair of side facelift sutures 10. Correspondingly, in procedure (A), three pairs of suture path lines 20A, 20B, 20C are marked on the user's half face with assistance of the marker ruler, including a pair of front facelift suture path lines 20A, a pair of mid facelift suture path lines 20B and a pair of side facelift suture path lines 20C. That is one more side facelift suture path line 20C is marked in addition to the example pattern as shown in FIGS. 9 to 15B.

It is appreciated that the lower segment (second segment) of suture 102 of each invasive suture 10 is implanted in a lower portion of the user's face for suspension and lifting effect and the upper segment (first segment) of suture 101 of each invasive suture 10 is implanted in an upper portion of the user's face for lifting and fixing effect. The lower segment 22 and the upper segment 21 of each facelift suture path line 20 are marked for implanting the lower segment of suture 102 and the upper segment of suture 101 of the corresponding invasive suture 10 therealong respectively, while the insertion mark 23 between the upper segments 21 and the lower segment 22 of each facelift suture path line 20 is marked for the first and second needles 11, 12 of the corresponding invasive suture 10 to insert there through the same insertion hole. If the first needle 11 is inserted first, the second needle 12 is preferred to insert at the same hole that the first needle 11 inserted, vice verse.

Referring to FIG. 16A, the pair of front facelift suture path lines 20A is extended starting from the position of the nasolabial fold to the malar mound and then ended at a position adjacent to the ear of the user on each half face of the user upwardly, rearwardly and inclinedly while the insertion marks 23A thereof are positioned around the malar mound of the user. It is important that the lower end or outlet mark 221A of the lower segment 22A of each of the front facelift suture path lines 20A must be extended and marked beyond the nasolabial fold, preferably perpendicular thereto approximately. The two front facelift suture path lines 20A can be marked in parallel manner or having a narrower distance between the lower ends or lower outlet marks 221A of the lower segments 22A (i.e. at the position of the nasolabial fold) and a wider distance between the upper ends or upper outlet marks 211A of the upper segments 21A (i.e. at the position adjacent to the ear). In other words, the two lower ends or outlet marks 221 of the two front facelift suture path lines 20A are preferred to be marked beyond the nasolabial fold and positioned between the nose and mouth corner such that, for example, if the nasolabial fold is deeper, positioned closer to the nose and if there are more marionette lines, positioned closer to the mouth corner.

The pair of mid facelift suture path lines 20B is extended starting from the position of the marionette line to the cheek and then ended at the position adjacent to the temple position of the user on each half face of the user upwardly, rearwardly and inclinedly while the insertion mark 23B is positioned at the cheek of the user. The lower end or outlet mark 221B of the lower segment 22B of each of the pair of mid facelift suture path lines 20B is marked beyond the marionette line(s), preferably perpendicular thereto approximately. The two mid facelift path lines 20B are marked to have a narrower distance between the lower ends or lower outlet marks 221B of the lower segments 22B (i.e. at the position of the marionette line(s)) and a wider distance between the two upper ends or upper outlet marks 211B of the upper segments 21B (i.e. at the temple position), wherein one of the pair of mid facelift suture path lines 20B is arranged and marked at an upper position with the upper end or upper outlet mark 211B of its upper segment 21B positioned above the upper end or upper outlet mark 211A of the upper front facelift path line 20A, while another one of the pair of mid facelift suture lines 20B is arranged and marked at a lower position below the upper end or upper outlet mark 211A of the lower front facelift path line 20A, such that the upper ends or upper outlet marks 211A, 211B are positioned and aligned at the temple position and adjacent to the user's ear. In addition, the upper segment 21B of the upper mid facelift path line 20B is extended intersecting with the upper segments 21A of the two front facelift suture path lines 20A.

The pair of side facelift suture path lines 20C is extended starting from the jowl position to the crows feet position on each half face of the user upwardly while the insertion mark 23C is positioned below the pair of mid facelift suture path lines 20B. The two side facelift suture path lines 20C can be marked in parallel manner or having a narrower distance between the lower ends or lower outlet marks 221C of the lower segments 22C (i.e. the jowl position) and a wider distance between the upper ends or upper outlet marks 211C of the upper segments 21C (i.e. the crows feet position). Both upper segments 21C of the two side facelift suture path lines 20C are extended upwardly to intersect with the two mid facelift suture path lines 20B and then the two front facelift suture path lines 20A.

It is worth mentioning that no insertion mark 23A, 23B, 23C of any of the front, mid and side facelift suture path lines 20A, 20B, 20C should positioned at the upper segments 21A, 21B, 21C nor the lower segments 22A, 22B, 22C of the front, mid and side facelift suture path lines 20A, 20B, 20C.

The layout and arrangement of the front, mid and side facelift suture path lines 20A, 20B, 20C as shown in FIG. 16A is specifically preferred for user who would like to provide more suspension and lifting effect to the mid face area (the portion around the cheek of the user) such that an intersection area (IA) is provided where the three pairs of front, mid and side facelift suture path lines 20 are arranged intersecting with each other at the encircle portion as shown in FIG. 16A that significantly enables a three-dimensional enhanced suspension and lifting effect through the intersecting invasive sutures 10 respectively implanted along the intersecting facelift suture path lines 20A, 20B, 20C.

The layout and arrangement of the three pairs of front, mid and side facelift suture path lines 20A, 20B, 20C not only provides suspended lifting effect to lower portion of the user's face, including the positions of nasolabial fold, marionette line and jowl as well as lifting and fixing effect to the upper portion of the user's face upwardly, rearwardly and sidewardly, but also provides a suspension and tighten effect to mid face of the user, including the positions of malar mound and cheek after the corresponding six invasive sutures 10 implanted along the six facelift suture path lines 20A, 20B, 20C. The intersecting area of the three pairs of front, mid and side facelift suture path lines 20A, 20B, 20C.

To younger user who does not have wrinkle but simply like to reshape the face, only one front facelift suture path line 20A or only one mid facelift suture path line 20B or only one side facelift suture path line 20C of the corresponding pair of facelift path line marks as shown in FIGS. 16A to 16C is marked so that only three to five invasive sutures 10 are implanted along with the following facelift suture path line marking arrangements:

(i) One front facelift suture path line 20A, one mid facelift suture path line 20B and one side facelift suture path line 20C are marked on the user face.

(ii) One front facelift suture path line 20A, one mid facelift suture path line 20B and a pair of side facelift suture path lines 20C are marked on the user face.

(iii) One front facelift suture path line 20A, a pair of mid facelift suture path lines 20B and one side facelift suture path line 20C are marked on the user face.

(iv) a pair of front facelift suture path lines 20A, one mid facelift suture path line 20B and one side facelift suture path line 20C are marked on the user face.

(v) One front facelift suture path line 20A, a pair of mid facelift suture path lines 20B and a pair of side facelift suture path lines 20C are marked on the user face.

(vi) a pair of front facelift suture path line 20A, one mid facelift suture path line 20B and a pair of side facelift suture path lines 20C are marked on the user face.

(vii) a pair of front facelift suture path lines 20A, a pair of mid facelift suture path lines 20B and one side facelift suture path line 20C are marked on the user face.

Referring to FIG. 16B, the three pairs of front, mid and side facelift suture path lines 20A, 20B, 20C are arranged in a general parallel manner while the pair of front facelift suture path lines 20A and the pair of mid facelift suture path lines 20B have not intersection and only the pair of side facelift suture path lines 20C is intersected with the pair of the front facelift suture path lines 20A extended in an upper position and the pair of mid facelift suture path lines 20B extended in a lower position. This layout and arrangement of the front, mid and side facelift suture path lines 20A, 20B, 20C is specifically preferred for user who would like to reshape his or her jawline and to preform eyelifting effect with the suspended and lifting invasive sutures 10 respectively implanted along the front, mid and side facelift suture path lines 20A, 20B, 20C, wherein the uplifting of the invasive sutures 10 implanted along the side facelift suture path lines 20C will also provide suspension and lifting effect to the facial portion around the front and mid facelift suture path lines 20A, 20B.

Referring to FIG. 16C, an alternative mode of the six facelift suture path lines 20A, 20B, 20C arrangement as shown in FIG. 16A is illustrated, wherein three pairs of front, mid and side facelift suture path lines 20A, 20B, 20C are also arranged in a general parallel manner where the pair of front facelift suture path lines 20A and the pair of side facelift suture path liens 20C are intersected at a rear portion adjacent to the ear of the user's face after the intersection of the side facelift suture path lines 20C with the pairs of front and mid facelift suture path lines 20A and 20B. Such arrangement is specifically preferred for user who likes to have more suspension and lifting effect to the skin tissue around cheek of the user.

Figure 17A:
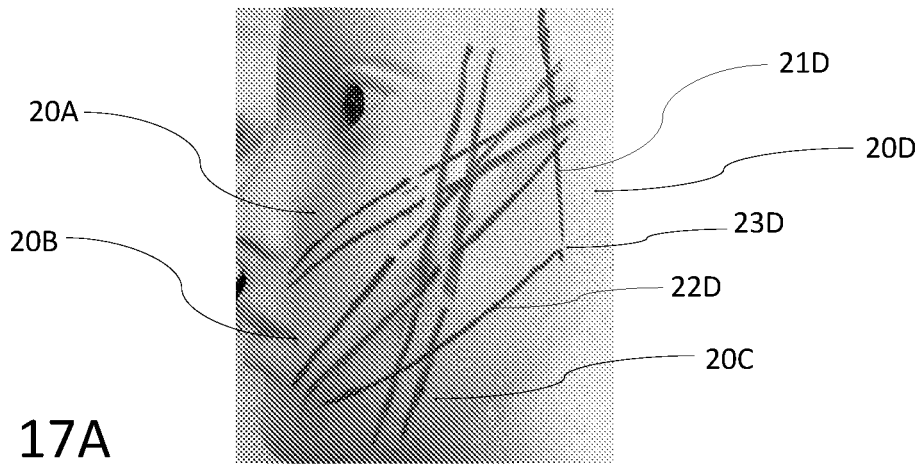
FIGS. 17A to 17C are schematic views illustrating patterns of marking layout and arrangement of seven facelift suture path lines on each half face of a user according to the preferred embodiment of the present invention.
Figure 17B:
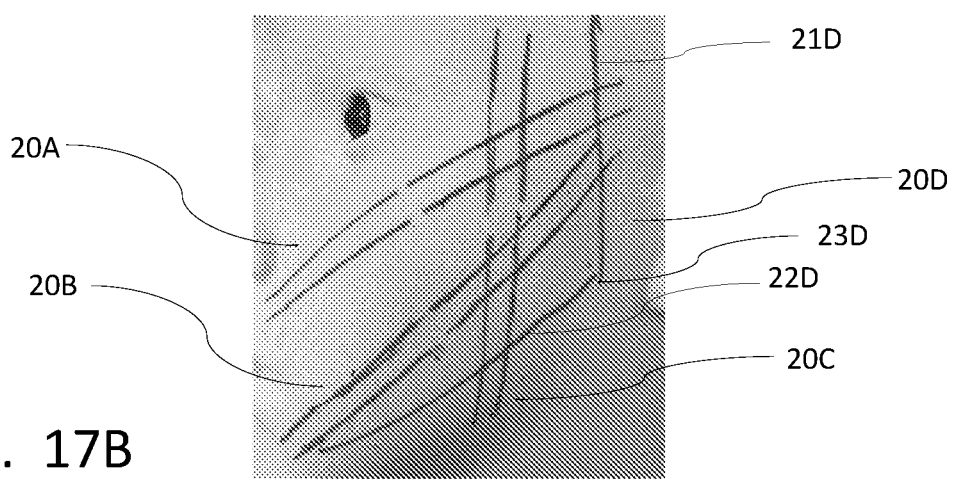
Figure 17C:
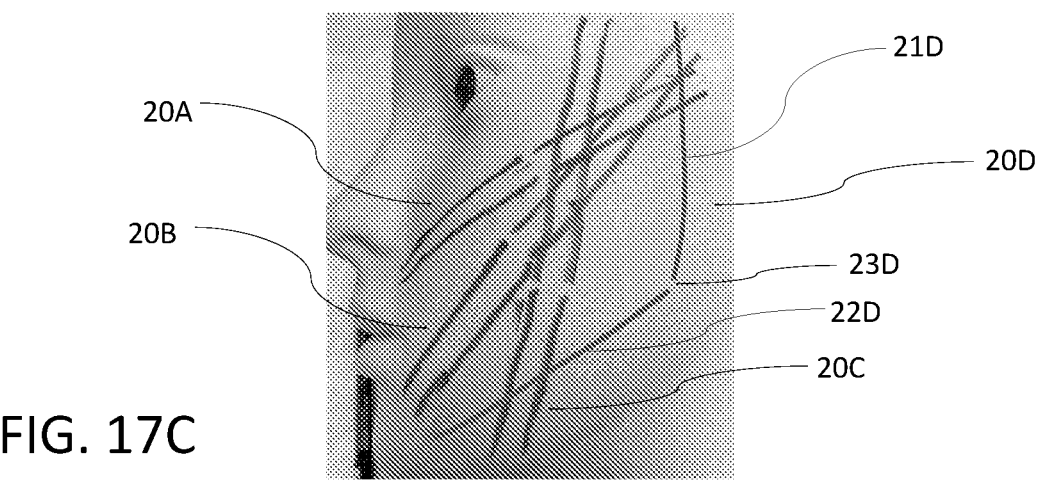

For anti-aging treatment, referring to FIGS. 17A to 17C, the aging sagging is more severe that an additional invasive suture 10 is implanted along the jawline, wherein an additional jawline facelift suture path line 20D is marked in addition to the three arrangements as illustrated in FIGS. 16A to 16C respectively. The jawline facelift suture path line 20D is different to the elongated linear shape of the front, mid and side pairs of facelift suture path lines 20A, 20B, 20B, wherein the jawline facelift suture path line 20D is in general L shape which has a lower segment 22D extended inclinedly and rearwardly along the user's jawline, generally from the chin portion to the jaw portion of the user, an upper segment 21D extended upwardly along a rear portion of the user, generally from the user's jaw portion to behind the user's temple portion, and an insertion mark 23D positioned at the user's jaw portion preferably, wherein the lower segment 22D of the jawline facelift suture path line 20D intersects with the lower segments 22C of the two side facelift suture path lines 20C and the upper segment 21D of the jawline facelift suture path line 20D intersects with the upper segments 21A of the two front facelift suture path lines 20A and the upper segments 21B of the two mid facelift suture path lines 20B. The invasive suture 10 implanted along the jawline facelift suture path line 20D provides further reinforcing suspension, lifting and fixing effects to the face tissue of the user to improve and reduce neck lines and the aging sagging of the apple chin, jowls and jawline of the user.

For treatment for tighter and plumper face as well as for anti-aging treatment to a user whose aging sagging is relatively more severe, referring to FIGS. 18A to 18F, one more invasive suture 10 can be selectively implanted, such that an additional facelift suture path line 20 is marked and added to the pair of front, mid or side facelift suture path lines 20A, 20B, 20C or a pair of jawline facelift suture path lines 20D.

Figure 18A:
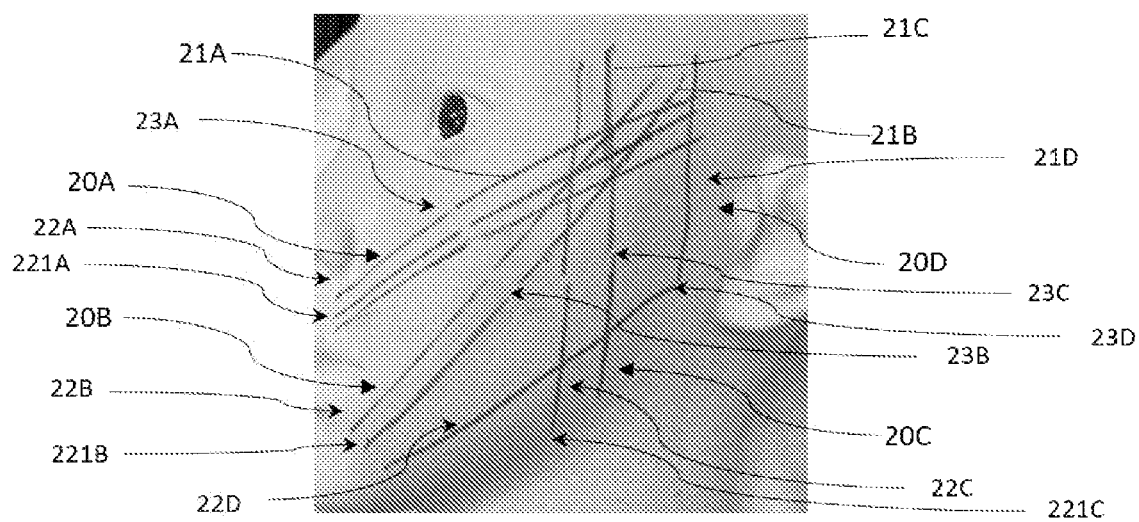
FIGS. 18A to 18F are schematic views illustrating patterns of marking layout and arrangement of eight facelift suture path lines on each half face of a user according to the preferred embodiment of the present invention.

Referring to FIG. 18A, three front facelift suture path lines 20A are extended starting from the position of the nasolabial fold to the malar mound and then ended at a position adjacent to the ear of the user on each half face of the user upwardly, rearwardly and inclinedly while the insertion marks 23A are positioned around the malar mound of the user. In other words, an additional front facelift suture path lines 20A is marked generally in parallel to at least one of the pair of front facelift suture path lines 20A as shown in FIG. 16A or FIG. 17C. Same principle applied that the lower end or outlet mark 221A of the lower segment 22A of each of the three front facelift suture path lines 20A must be marked beyond the nasolabial fold, preferably perpendicular thereto approximately.

Similarly, a pair of mid facelift suture path lines 20B is extended starting from the position of the marionette line to the cheek and then ended at the position adjacent to the temple position of the user on each half face of the user upwardly, rearwardly and inclinedly while the insertion mark 23B is positioned at the cheek of the user. The lower end or outlet mark 221B of the lower segment 22B of each of the two mid facelift suture path lines 20B is marked beyond the marionette line(s), preferably perpendicular thereto approximately.

The pair of side facelift suture path lines 20C is extended starting from the jowl position to the crows feet position on each half face of the user upwardly while the insertion mark 23C is positioned below the pair of mid facelift suture path lines 20B. The two side facelift suture path lines 20C can be marked in parallel manner or having a narrower distance between the upper ends or upper outlet marks 211C of the upper segments 21C (i.e. the crows feet position) and a wider distance between the lower ends or lower outlet marks 221C of the lower segments 22C (i.e. the jowl position).

Also, a L-shape jawline facelift suture path line 20D is marked, wherein a lower segment 22D thereof is extended inclinedly and rearwardly along the user's jawline, generally from the chin portion to the jaw portion of the user, an upper segment 21D thereof is extended upwardly along a rear portion of the user, generally from the user's jaw portion to behind the user's temple portion, and an insertion mark 23D thereof is positioned near the user's jaw portion, wherein the lower segment 22D of the jawline facelift suture path line 20D intersects with the lower segments 22C of the two side facelift suture path lines 20C and the upper segment 21D of the jawline facelift suture path line 20D intersects with the upper segments 21A of the two front facelift suture path lines 20A and the upper segments 21B of the two mid facelift suture path lines 20B.

The two upper segments 21B of the two mid facelift suture path lines 20B are intersected with the three upper segments 21A of the three front facelift suture path lines 20A. Both upper segments 21C of the two side facelift suture path lines 20C are extended upwardly to intersect with the two mid facelift suture path lines 20B and the two front facelift suture path lines 20A. Accordingly, the three upper segments 21A of the three front facelift suture path lines 20A, two upper segments 21B of the two mid facelift suture path lines 20B and the two upper segments 21C of the two side facelift suture path lines 20C are intersected around the temple and cheek portion of the user's face, such that seven upper segments of invasive sutures 10 are intersectingly implanted accordingly. Since three invasive sutures (front facelift sutures) 10 are implanted along the three front facelift suture path lines 20A, the suspension and lifting abilities to the front and mid face portion, removal of the nasolabial fold(s) and tightening the portion between nose and the eye of the user are enhanced by correlatively adjusting the relative positions and the lifting effect of the three front facelift sutures 10.

In addition to the reinforcing suspension, lifting and fixing effects provided by the invasive suture 10 implanted along the jawline facelift suture path line 20D, the seven intersecting upper segments 11 of the three front facelift sutures 10, the two mid facelift sutures 10 and two side facelift sutures 10 implanted along the seven upper segments 21A, 21B, 21C of the three front, two mid and two side facelift suture path lines 20A, 20B, 20C provide a better suspension, lifting and fixing effect resulting in a firmer and plump face.

Figure 18B:
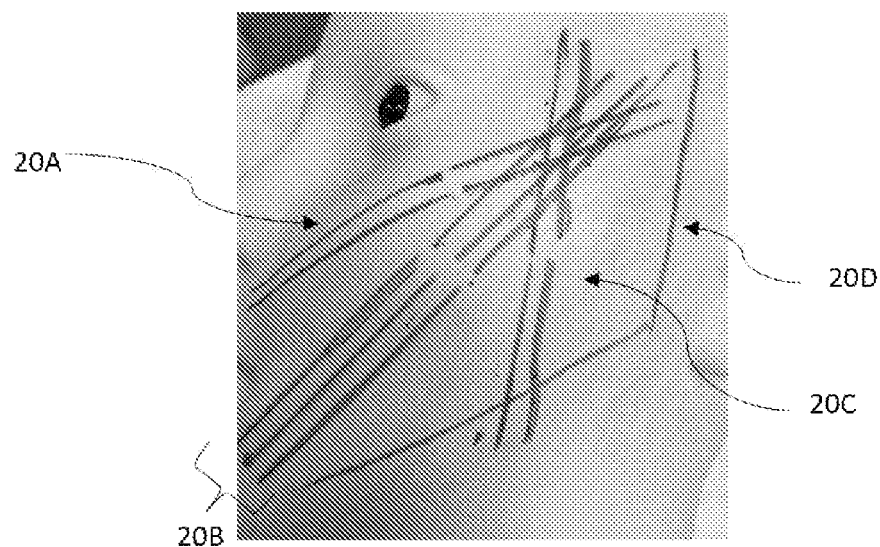

Referring to FIG. 18B, an alternative mode of the facelift suture path line marking layout and arrangement as shown in FIG. 18A is illustrated, wherein instead of marking three front facelift suture path lines 20A, an additional mid facelift suture path lines 20B is added the pair of mid facelift suture path lines 20B as illustrated in FIG. 16A or FIG. 17C. In other words, a total of three mid facelift suture path lines 20B are marked with the pair of front facelift suture path lines 20A, the pair of side facelift suture path lines 20C and the jawline facelift suture path line 20C. Since three invasive sutures (mid facelift sutures) 10 are implanted along the three mid facelift suture path lines 20B, the suspension and lifting abilities to the mid face and malar mound portion, removal of the marionette line(s) and making cheeks firmer for the user are enhanced by correlatively adjusting the relative positions and the lifting effect of the three mid facelift sutures 10.

In addition to the reinforcing suspension, lifting and fixing effects provided by the invasive suture 10 implanted along the jawline facelift suture path line 20D, the seven intersecting upper segments 11 of the two front facelift sutures 10, the three mid facelift sutures 10 and two side facelift sutures 10 (as shown in FIG. 1) implanted along the seven upper segments 21A, 21B, 21C of the two front, three mid and two side facelift suture path lines 20A, 20B, 20C provide a better suspension, lifting and fixing effect resulting in a firmer and plump cheek and temple portions of the user's face.

Figure 18C:
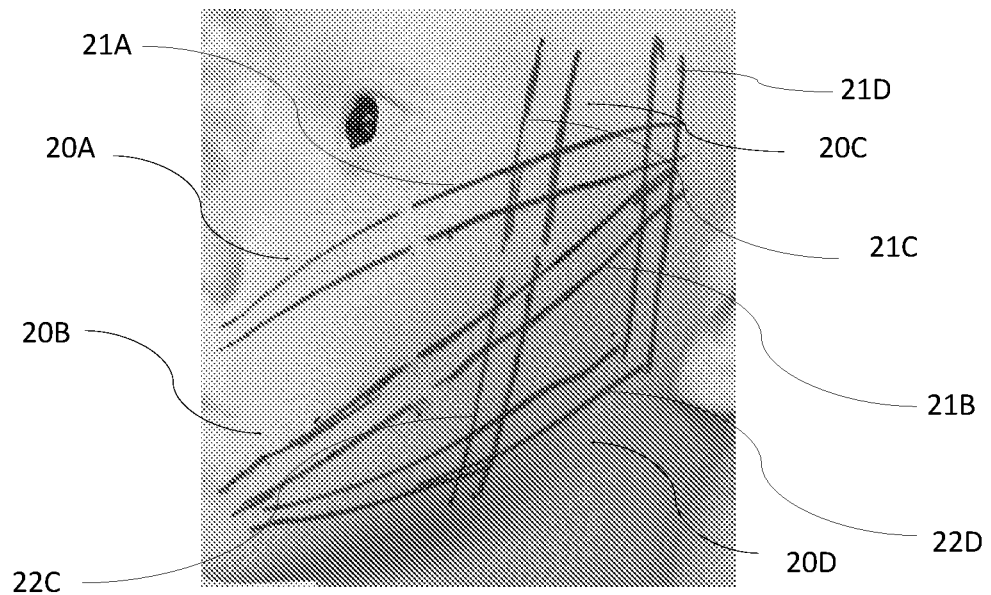

Referring to FIG. 18C, an alternative mode of the facelift suture path line marking layout and arrangement as shown in FIG. 16B or FIG. 17B is illustrated, wherein two L-shape jawline facelift suture path lines 20D are marked, wherein the two lower segments 22D of the two jawline facelift suture path lines 20D are intersected with the two lower segments 22C of the two side facelift suture path lines 20C and the two upper segments 21D of the two jawline facelift suture path lines 20D are intersected with the two upper segments 21B of the two mid facelift suture path lines 20B and then the two upper segments 21A of the two front facelift suture path lines 20A. Accordingly, the two jawline facelift sutures 10 implanted along the two jawline facelift suture path lines 20D not only provide further suspension and lifting ability to the jawline portion of the user, but also provide a fixing effect to the reshaped jawline of the user and enhance the suspending and lifting ability of the upper segments 11 of the front and mid facelift sutures 10 (as shown in FIG. 1) implanted along the two upper segments 21B of the two mid facelift suture path lines 20B and the two upper segments 21A of the two front facelift suture path lines 20A. Such arrangement substantially will provide a firmer jawline for the user.

Figure 18D:
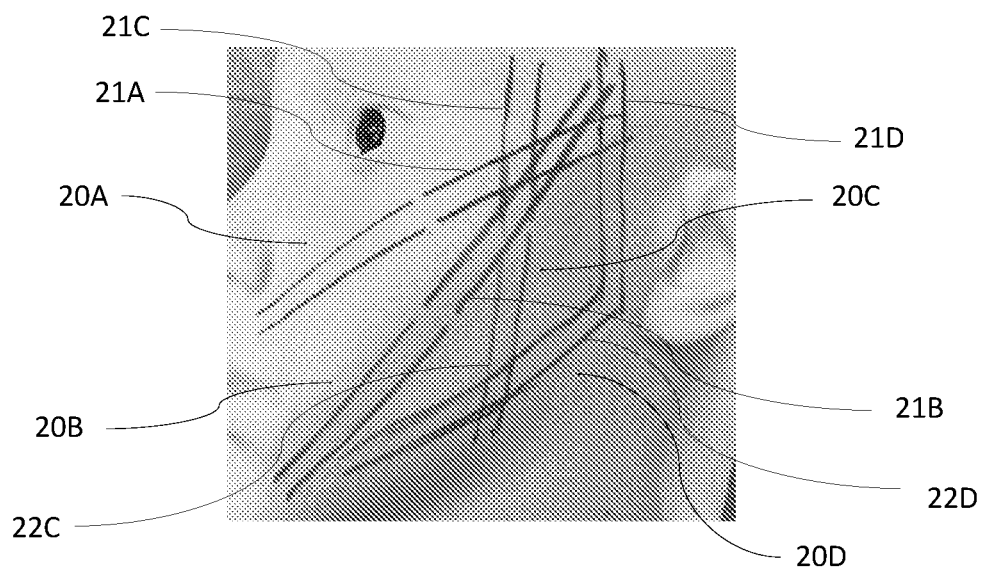

Referring to FIG. 18D, an alternative mode of the facelift suture path line marking layout and arrangement as shown in FIG. 16C or FIG. 17C is illustrated, wherein two L-shape jawline facelift suture path lines 20D are marked, wherein the two lower segments 22D of the two jawline facelift suture path lines 20D are intersected with the two lower segments 22C of the two side facelift suture path lines 20C and the two upper segments 21D of the two jawline facelift suture path lines 20D are intersected with the two upper segments 21B of the two mid facelift suture path lines 20B and then at least one upper segment 21A of the two front facelift suture path lines 20A. Accordingly, the two jawline facelift sutures 10 implanted along the two jawline facelift suture path lines 20D not only provide further suspension and lifting ability to the jawline portion of the user, but also provide a fixing effect to the reshaped jawline of the user and enhance the suspending and lifting ability of the upper segments 11 of the front and mid facelift sutures 10 (as shown in FIG. 1) implanted along the two upper segments 21B of the two mid facelift suture path lines 20B and the two upper segments 21A of the two front facelift suture path lines 20A. Such arrangement substantially will provide a firmer jawline and plumper cheek for the user.

Figure 18E:
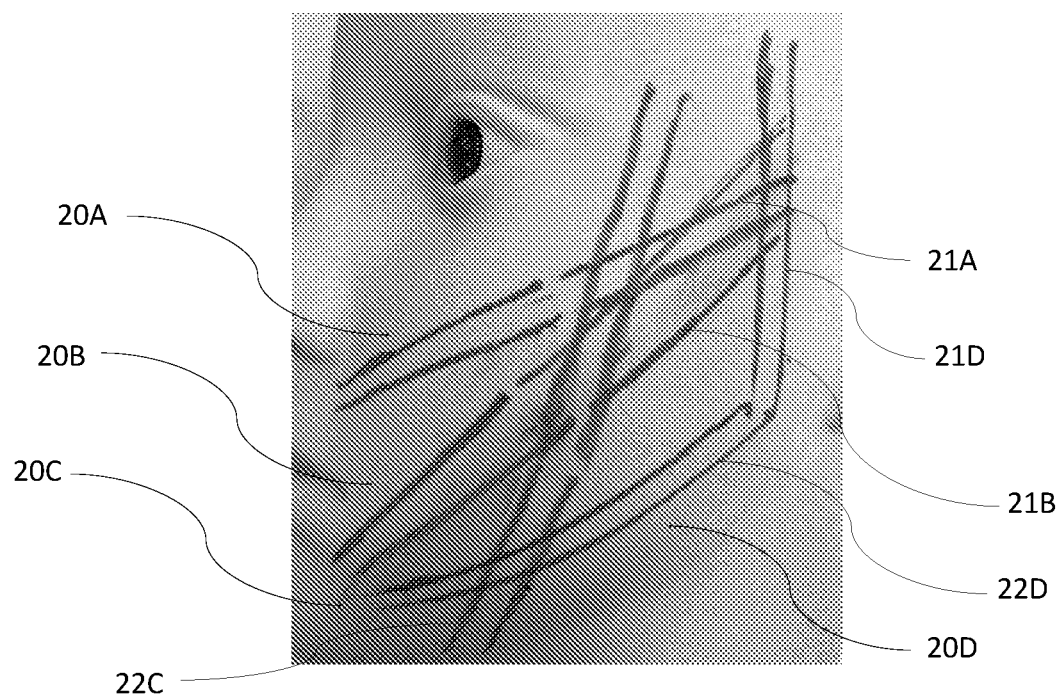

Referring to FIG. 18E an alternative mode of the facelift suture path line marking layout and arrangement as shown in FIG. 16A is illustrated, wherein two additional L-shape jawline facelift suture path lines 20D are marked, wherein the two lower segments 22D of the two jawline facelift suture path lines 20D are intersected with the two lower segments 22C of the two side facelift suture path lines 20C and the two upper segments 21D of the two jawline facelift suture path lines 20D are intersected with the two upper segments 21B of the two mid facelift suture path lines 20B and the two upper segments 21A of the two front facelift suture path lines 20A. Accordingly, the two jawline facelift sutures 10 implanted along the two jawline facelift suture path lines 20D not only provide further suspension and lifting ability to the jawline portion of the user, but also provide a fixing effect to the reshaped jawline of the user and enhance the suspending and lifting ability of the upper segments 11 of the front and mid facelift sutures 10 (as shown in FIG. 1) implanted along the two upper segments 21B of the two mid facelift suture path lines 20B and the two upper segments 21A of the two front facelift suture path lines 20A. Such arrangement substantially will provide a firmer jawline and plumper cheek for the user.

Figure 18F:
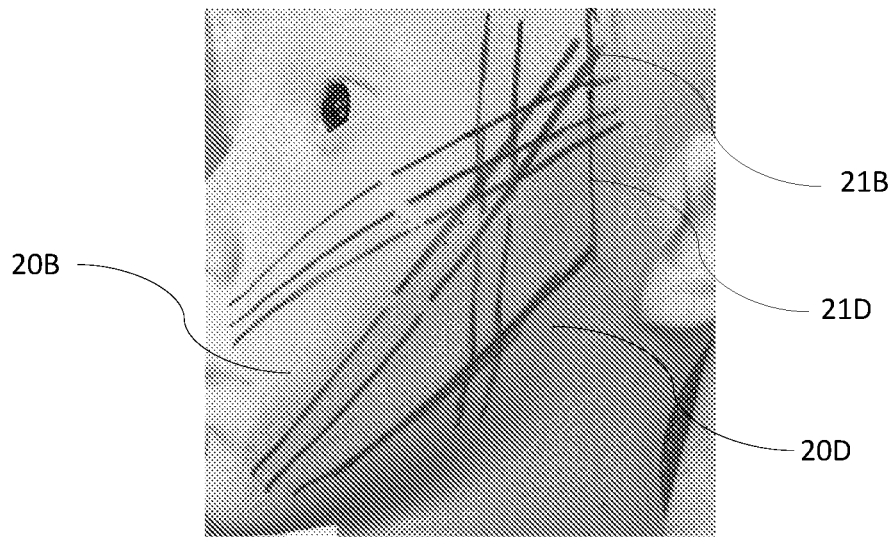

Referring to FIG. 18F, an alternative mode of the facelift suture path line marking layout and arrangement as shown in FIG. 18A is illustrated, wherein the upper segment 21D of the jawline facelift suture path line 20D is also intersected with at least one upper segment 21B of the pair of mid facelift suture path lines 20B such that the upper segment 11 of the jawline facelift suture 10 (as shown in FIG. 1) implanted along the upper segment 21D of the jawline facelift suture path line 20D further provides an upward suspending and lifting effect to the mid facelift sutures 10 implanted along the pair of mid facelift suture path lines 20B.

For treatment for user having large face plate, nine to ten invasive sutures 10 are preferred to be implanted in each half face of the user, wherein the corresponding facelift suture path line marking layout and arrangement is illustrated in FIGS. 19A to 19G and FIGS. 20A to 20D.

Figure 19A:
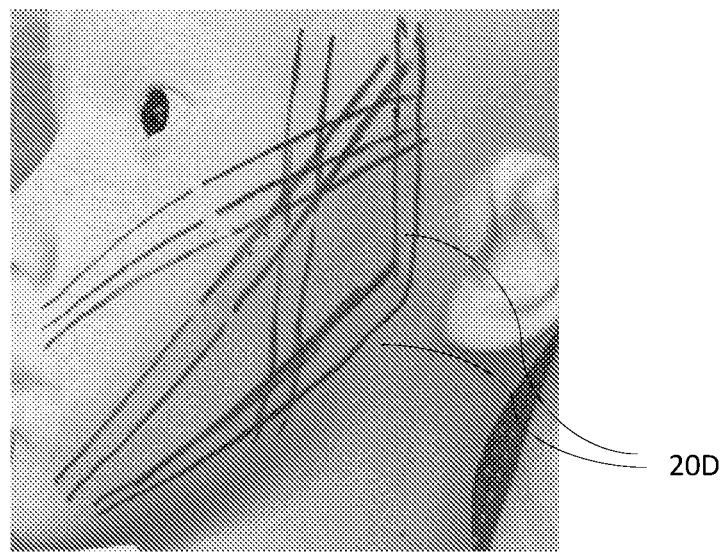
FIGS. 19A to 19G are schematic views illustrating patterns of marking layout and arrangement of nine facelift suture path lines on each half face of a user according to the preferred embodiment of the present invention.

Referring to FIG. 19A, an alternative mode of the facelift suture path line marking layout and arrangement as shown in FIG. 18F is illustrated, wherein one more jawline facelift suture path line 20D is added and marked, such that two jawline facelift sutures 10 (as shown in FIG. 1) are implanted along the jawline of the user to enhance the suspension and lifting effects to better reshape the jawline of the user with larger face plate.

Figure 19B:
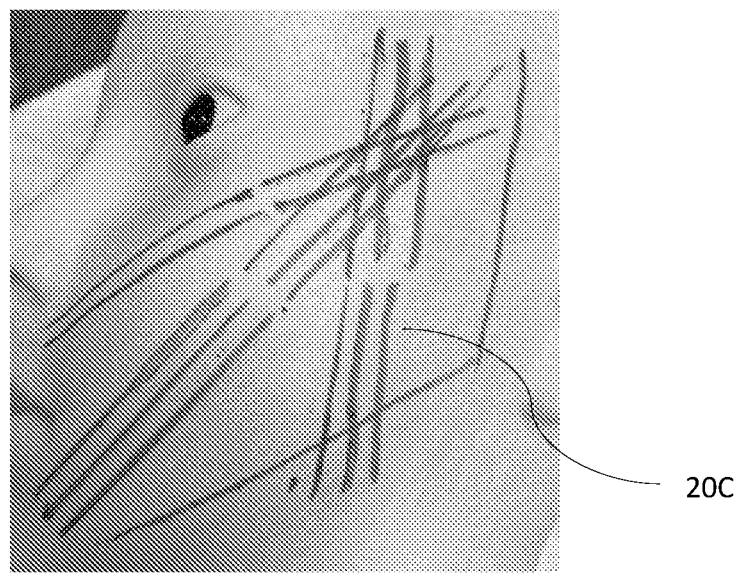

Referring to FIG. 19B, an alternative mode of the facelift suture path line marking layout and arrangement as shown in FIG. 18B is illustrated, wherein one more side facelift suture path line 20C is added and marked for the implant of one more side facelift suture 10 (as shown in FIG. 1) so as to further enhance the upward suspension and lifting ability from the jowl to the cheek and temple portions of the user for further firmer and plumper effect through the three side facelift sutures 10 implanted along the three side facelift suture path lines 20C.

Figure 19C:
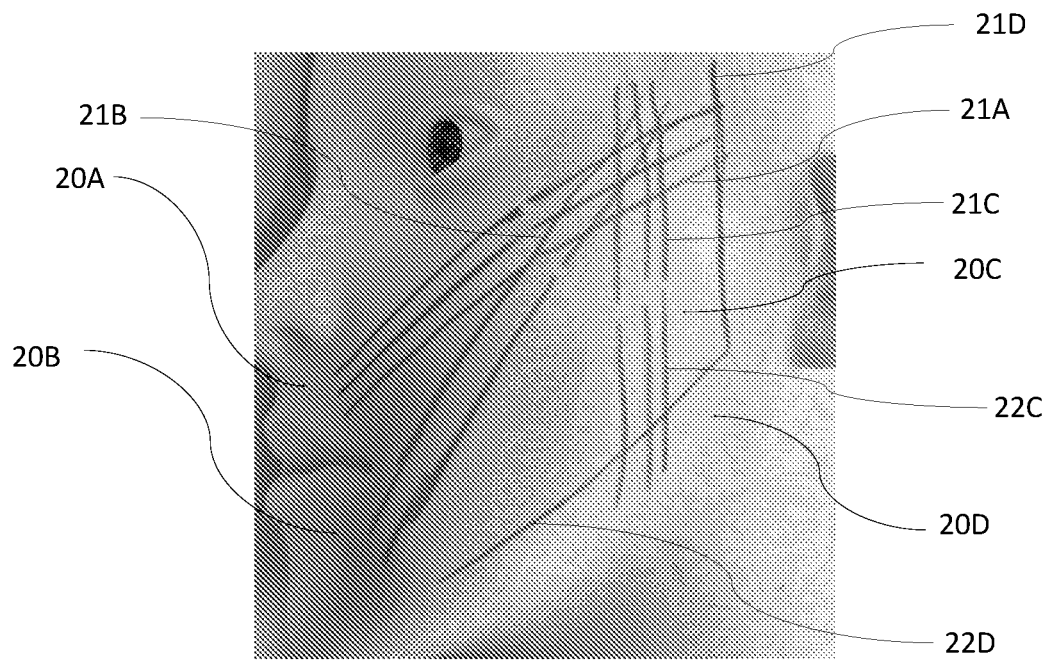

Referring to FIG. 19C, three front facelift suture path lines 20A, two mid facelift suture path lines 20B, three side facelift suture path lines 20C and one jawline facelift suture path line 20D are marked on each half face of the user. The three front facelift suture path lines 20A are marked parallelly in general and extended upwardly, rearwardly and inclinedly from the nasolabial fold to cheek portion and then the temple portion of the user. The two mid facelift suture path lines 20B are marked parallelly in general and extended upwardly, rearwardly and inclinedly from marionette line to the cheek portion and then the temple portion of the user, which two upper segments 21B are intersected with the three upper segments 21A of the three front facelift suture path lines 21A at the cheek portion of the user. The three side facelift suture path lines 20C are marked in parallelly in general and extended upwardly from the jowl position to the crows feet portion of the user, which three upper segments 21C are intersected with the three upper segments 21A of the three front facelift suture path lines 20A and then the two upper segments 21B of the two mid facelift suture path lines 20B. The intersecting of the two upper segments 21B of the two mid facelift suture path lines 20B with the three upper segments 21A of the three front facelift suture path lines 20A is arranged at the cheek portion inclinedly, that is positioned before the intersecting of the upper segments 21C of the three side facelift suture path lines 20C with the upper segments 21A of the three front facelift suture path lines 20A, i.e. around the temple portion. The lower segment 22D of the jawline facelift suture path line 20D is intersected with the lower portions of the three lower segments 22C of the three side facelift suture path lines 20C and the upper portion of the upper segment 21D of the jawline facelift suture path line 20D is intersected with the upper portions of the three upper segments 21A of the three front facelift suture path lines 20A. Such facelift suture path line marking layout and arrangement is specifically preferred for the user who has deeper nasolabial fold and crows feet and more severe cheek sagging problems by providing more intersecting invasive sutures 10 around cheek and temple portions of the user that is significantly good for upward and rearward lifting the facial tissue at the cheek and temple portions of the user to tighten the cheek and reduce crows feet effectively while the three front facelift sutures 10 being implanted along the three front facelift suture path lines 20A enhance the reducing of nasolabial fold. The three side facelift sutures 10 (as shown in FIG. 1) to be implanted along the three side facelift suture path lines 20C substantially enhance the uplifting and fixing effects to the lower segment of the jawline facelift suture 10 implanted along the lower segment 22D of the jawline facelift suture path line 20D that further lifts the jowl portion and reshape the face plate of the user.

Figure 19D:
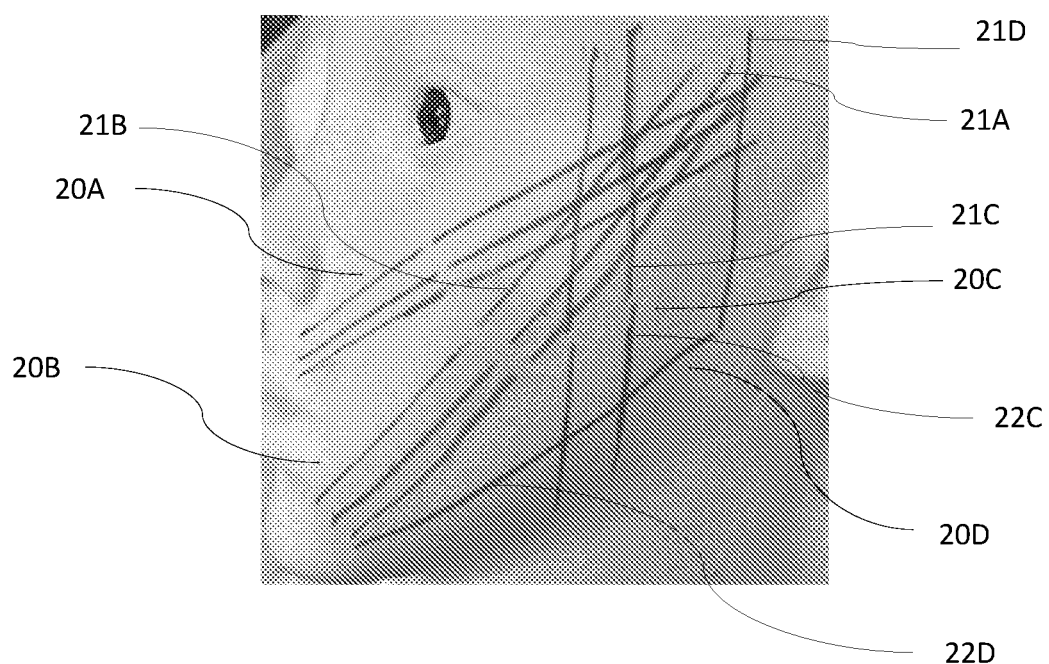

Referring to FIG. 19D, three front facelift suture path lines 20A, three mid facelift suture path lines 20B, two side facelift suture path lines 20C and one jawline facelift suture path line 20D are marked on each half face of the user. The three front facelift suture path lines 20A are marked parallelly in general and extended upwardly, rearwardly and inclinedly from the nasolabial fold to cheek portion and then the temple portion of the user. The three mid facelift suture path lines 20B are marked in parallelly in general and extended upwardly, rearwardly and inclinedly from marionette line to the cheek portion and then the temple portion of the user, which three upper segments 21B are intersected with the three upper segments 21A of the three front facelift suture path lines 21A at the cheek portion of the user. The two side facelift suture path lines 20C are marked parallelly in general and extended upwardly from the jowl position to the crows feet portion of the user, which two upper segments 21C are intersected with the three upper segments 21A of the three front facelift suture path lines 20A and the three upper segments 21B of the three mid facelift suture path lines 20B. The intersecting of the upper segments 21C of the two side facelift suture path lines 20C with the three upper segments 21A of the three front facelift suture path lines 20B is arranged at the cheek portion and positioned before the intersecting of the three upper segments 21B of the three mid facelift suture path lines 20B with three upper segments 21A of the three front facelift suture path lines 20A inclinedly at the temple portion. The lower segment 22D of the jawline facelift suture path line 20D is intersected with the lower portions of the three lower segments 22C of the three side facelift suture path lines 20C and the upper portion of the upper segment 21D of the jawline facelift suture path line 20D is intersected with the upper portions of the three upper segments 21A of the three front facelift suture path lines 20A. Such facelift suture path line marking layout and arrangement is specifically preferred for the user who has deeper nasolabial fold, marionette line and crows feet and more severe cheek sagging problems by providing more intersecting invasive sutures 10 (as shown in FIG. 1) around cheek and temple portions of the user that is significantly good for upward and rearward lifting the facial tissue at the cheek and temple portions of the user to tighten the cheek and reduce crows feet effectively while the three front facelift sutures 10 and the three mid facelift sutures 10 (as shown in FIG. 1) implanted along the three front facelift suture path lines 20A and the three mid facelift suture path lines 20B enhance the reducing of nasolabial fold and marionette line respectively.

Figure 19E:
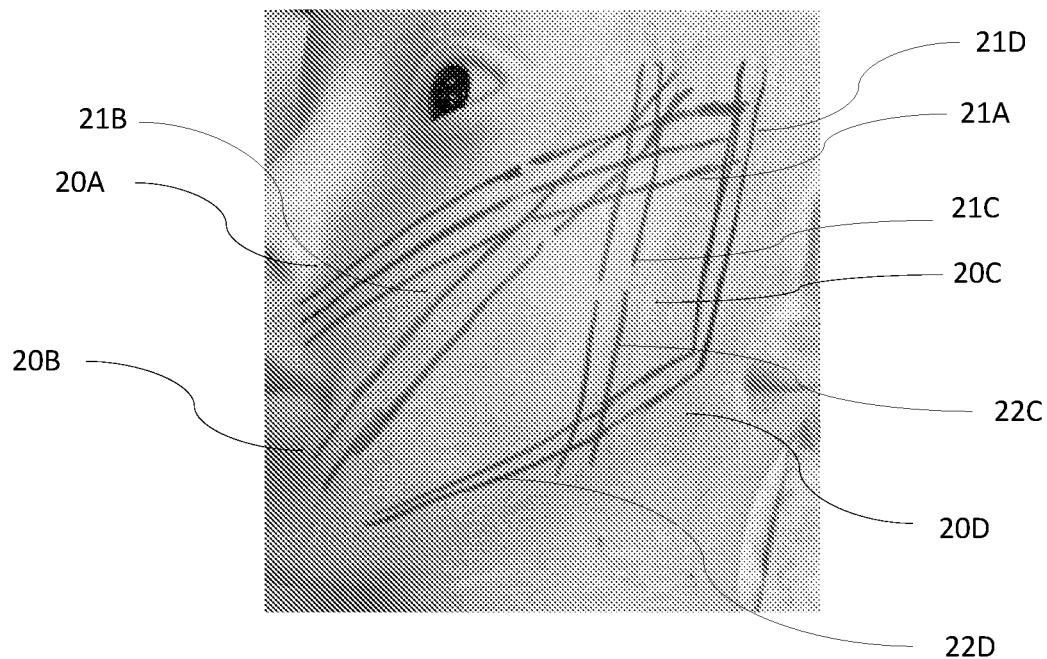

Referring to FIG. 19E, three front facelift suture path lines 20A, two mid facelift suture path lines 20B, two side facelift suture path lines 20C and two jawline facelift suture path lines 20D are marked on each half face of the user. The three front facelift suture path lines 20A are marked parallelly in general and extended upwardly, rearwardly and inclinedly from the nasolabial fold to cheek portion and then the temple portion of the user. The two mid facelift suture path lines 20B are marked parallelly in general and extended upwardly, rearwardly and inclinedly from marionette line to the cheek portion and then the temple portion of the user, which two upper segments 21B are intersected with the three upper segments 21A of the three front facelift suture path lines 21A at the cheek portion of the user. The two side facelift suture path lines 20C are marked parallelly in general and extended upwardly from the jowl position to the crows feet portion of the user, which two upper segments 21C are intersected with the three upper segments 21A of the three front facelift suture path lines 20A and the two upper segments 21B of the two mid facelift suture path lines 20B at the temple portion of the user. The intersecting of the upper segments 21B of the two mid facelift suture path lines 20B with the three upper segments 21A of the three front facelift suture path lines 20A is arranged inclinedly around the cheek portion and positioned before the intersecting of the upper segments 21C of the two side facelift suture path lines 20C with the three upper segments 21A of the three front facelift suture path lines 20A around the temple portion while the upper segments 21B, 21C of the mid and side facelift suture path lines 20B, 20C are intersected near to the crow feet of the user that, therefore, the upwardly lifting side facelift sutures 10 implanted along the side facelift suture path lines 20C and the upwardly and rearwardly lifting of mid facelift sutures 10 being implanted along the mid facelift suture path lines 20B can effectively reduce the crows feet of the user and tighten the cheek of the user. The lower segments 22D of the two jawline facelift suture path lines 20D are intersected with the lower portions of the two lower segments 22C of the two side facelift suture path lines 20C and the upper portion of at least one of the two upper segments 21D of the two jawline facelift suture path lines 20D are intersected with the upper portions of the three upper segments 21A of the three front facelift suture path lines 20A. Such facelift suture path line marking layout and arrangement is specifically preferred for the user who has deeper nasolabial fold and crows feet and more severe jawline sagging problems by providing more intersecting invasive sutures 10 (as shown in FIG. 1) around cheek and temple portions of the user that is significantly good for upward and rearward lifting the facial tissue at the cheek and temple portions of the user to tighten the cheek and reduce crows feet effectively while the three front facelift sutures 10 (as shown in FIG. 1) being implanted along the three front facelift suture path lines 20A enhance the reducing of nasolabial fold. The two jawline facelift sutures 10 to be implanted along the two jawline facelift suture path lines 20D substantially enhance the uplifting and fixing effects to the jawline by reinforcing the lifting of the jowl portion to reshape the face plate of the user.

Figure 19F:
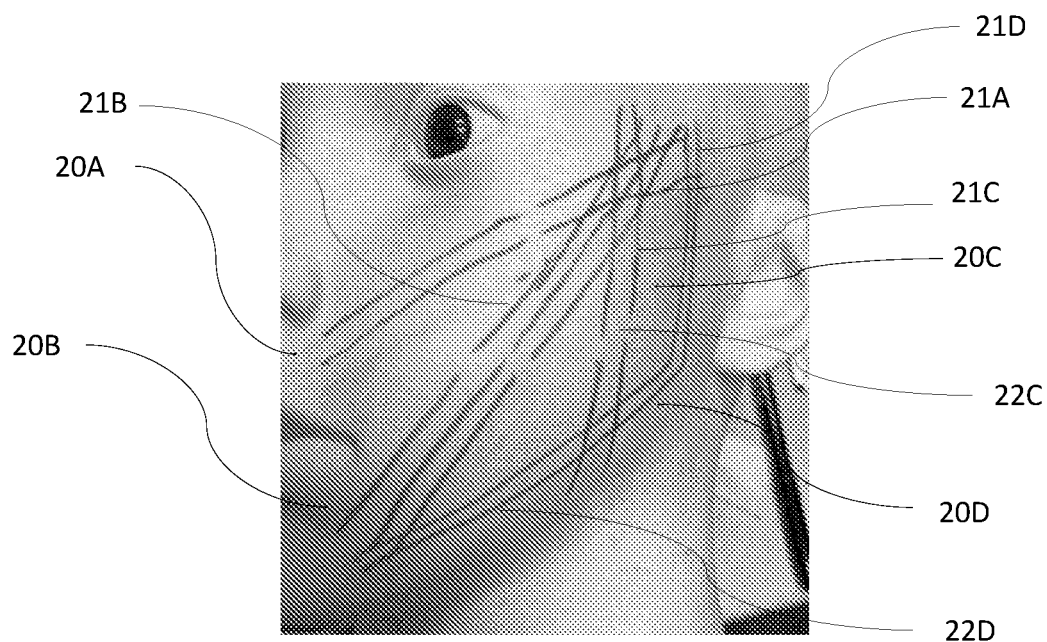

Referring to FIG. 19F, two front facelift suture path lines 20A, three mid facelift suture path lines 20B, two side facelift suture path lines 20C and two jawline facelift suture path lines 20D are marked on each half face of the user. The two front facelift suture path lines 20A are marked parallelly in general and extended upwardly, rearwardly and inclinedly from the nasolabial fold to cheek portion and then the temple portion of the user. The three mid facelift suture path lines 20B are marked parallelly in general and extended upwardly, rearwardly and inclinedly from marionette line to the cheek portion and then the temple portion of the user, which three upper segments 21B are intersected with the two upper segments 21A of the two front facelift suture path lines 21A at the cheek or temple portion of the user. The two side facelift suture path lines 20C are marked parallelly in general and extended upwardly from the jowl position to the crows feet portion of the user, which two upper segments 21C are intersected with the three upper segments 21B of the three mid facelift suture path lines 20B and the two upper segments 21A of the two front facelift suture path lines 20A at the temple portion of the user. The intersecting of the upper segments 21B of the three mid facelift suture path lines 20B with the two upper segments 21A of the two front facelift suture path lines 20A is arranged inclinedly around the cheek or temple portion where the upper segments 21C of the two side facelift suture path lines 20C are intersected with the three upper segments 21B of the three mid facelift suture path lines 20B and the two upper segments 21A of the two front facelift suture path lines 20A. Accordingly, the upper segments 11 of the seven front, mid and side facelift sutures 10 (as shown in FIG. 1) are intersected at the cheek or temple portion of the user that provides an effective suspension and lifting ability to the cheek or temple portion through upwardly, rearwardly and inclinedly lifting of the implanted front, mid and side facelift sutures 10 (as shown in FIG. 1) so as to provide a firmer and plumper cheek and temple portion for the user while efficiently reducing crows feet for the user. The lower segments 22D of the two jawline facelift suture path lines 20D are intersected with the lower portions of the two lower segments 22C of the two side facelift suture path lines 20C and the upper portions of the two upper segments 21D of the two jawline facelift suture path lines 20D are intersected with the upper portion of at least one of the two upper segments 21A of the two front facelift suture path lines 20A. Such facelift suture path line marking layout and arrangement is specifically preferred for the user who has deeper marionette line and crows feet and more severe jawline sagging problems by providing more intersecting invasive sutures 10 (as shown in FIG. 1) around cheek and temple portions of the user that is significantly good for upward and rearward lifting the facial tissue at the cheek and temple portions of the user to tighten the cheek and reduce crows feet effectively while the three mid facelift sutures 10 (as shown in FIG. 1) being implanted along the three mid facelift suture path lines 20B enhance the reducing of marionette line(s). The two jawline facelift sutures 10 (as shown in FIG. 1) to be implanted along the two jawline facelift suture path lines 20D substantially enhance the uplifting and fixing effects to the jawline by reinforcing the lifting of the jowl portion to reshape the face plate of the user.

Figure 19G:
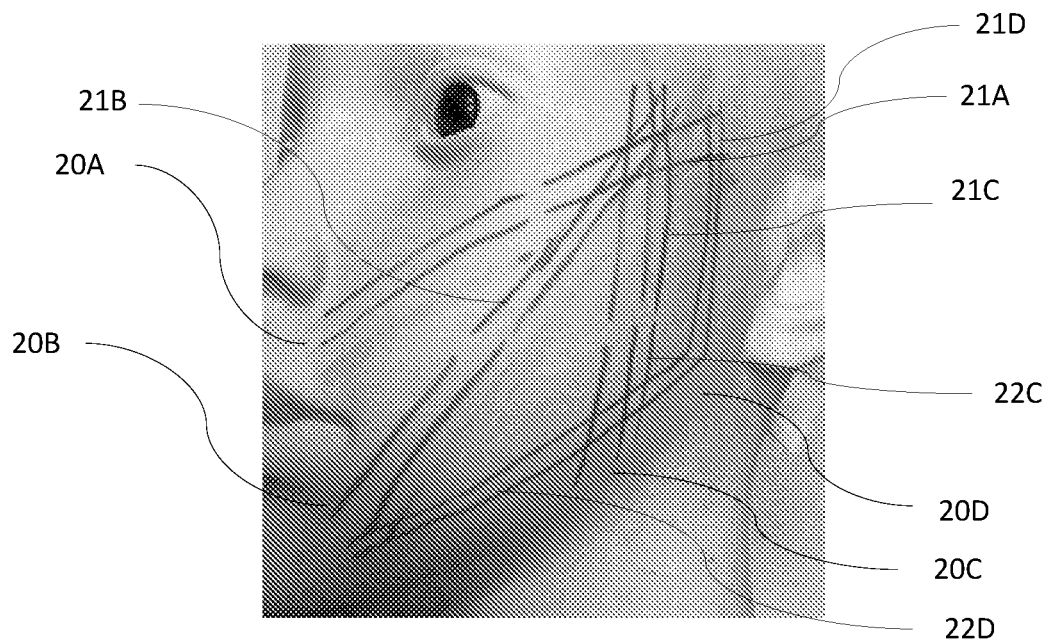

Referring to FIG. 19G, two front facelift suture path lines 20A, two mid facelift suture path lines 20B, three side facelift suture path lines 20C and two jawline facelift suture path lines 20D are marked on each half face of the user. The two front facelift suture path lines 20A are marked parallelly in general and extended upwardly, rearwardly and inclinedly from the nasolabial fold to cheek portion and then the temple portion of the user. The two mid facelift suture path lines 20B are marked parallelly in general and extended upwardly, rearwardly and inclinedly from marionette line to the cheek portion and then the temple portion of the user, which two upper segments 21B are intersected with the two upper segments 21A of the two front facelift suture path lines 21A at the cheek or temple portion of the user. The three side facelift suture path lines 20C are marked parallelly in general and extended upwardly from the jowl position to the crows feet portion of the user, which three upper segments 21C are intersected with the two upper segments 21B of the two mid facelift suture path lines 20B and the two upper segments 21A of the two front facelift suture path lines 20A at the temple portion of the user. The intersecting of the upper segments 21B of the twp mid facelift suture path lines 20B with the two upper segments 21A of the two front facelift suture path lines 20A is arranged inclinedly around the cheek or temple portion where the upper segments 21C of the three side facelift suture path lines 20C are intersected with the two upper segments 21B of the two mid facelift suture path lines 20B and the two upper segments 21A of the two front facelift suture path lines 20A. Accordingly, the upper segments 11 of the seven front, mid and side facelift sutures 10 (as shown in FIG. 1) are intersected at the cheek or temple portion of the user that provides an effective suspension and lifting ability to the cheek or temple portion through upwardly, rearwardly and inclinedly lifting of the implanted front, mid and side facelift sutures 10 so as to provide a firmer and plumper cheek and temple portion for the user while efficiently lifting the jowl portion to reshape the jawline the user. The lower segments 22D of the two jawline facelift suture path lines 20D are intersected with the lower portions of the three lower segments 22C of the three side facelift suture path lines 20C and the upper portions of the two upper segments 21D of the two jawline facelift suture path lines 20D are intersected with the upper portions of the two upper segments 21A of the two front facelift suture path lines 20A. Such facelift suture path line marking layout and arrangement is specifically preferred for the user who has severe sagging problems at the cheek, temple and jowl portions of the user by providing more intersecting invasive sutures 10 (as shown in FIG. 1) around cheek and temple portions of the user that is significantly good for upward and rearward lifting the facial tissue at the cheek and temple portions of the user to tighten the cheek while the three side facelift sutures 10 being implanted along the three side facelift suture path lines 20C enhance the suspension and fixing of the two jawline facelift sutures 10 (as shown in FIG. 1) implanted along the two jawline facelift suture path lines 20D by reinforcing the lifting of the jowl portion to reshape the face plate of the user.

For best improvement to user having deeper folds and lines and severe aging sagging, a total of ten invasive sutures 10 (as shown in FIG. 1) are able to be implanted to each half face of the user as, for example, illustrated in FIG. 20A to 20D according to the present invention. Accordingly, ten facelift suture path lines 20 are marked on each half face of the user to guide the placing and aligning of the corresponding ten facelift sutures 10 respectively.

Figure 20A:
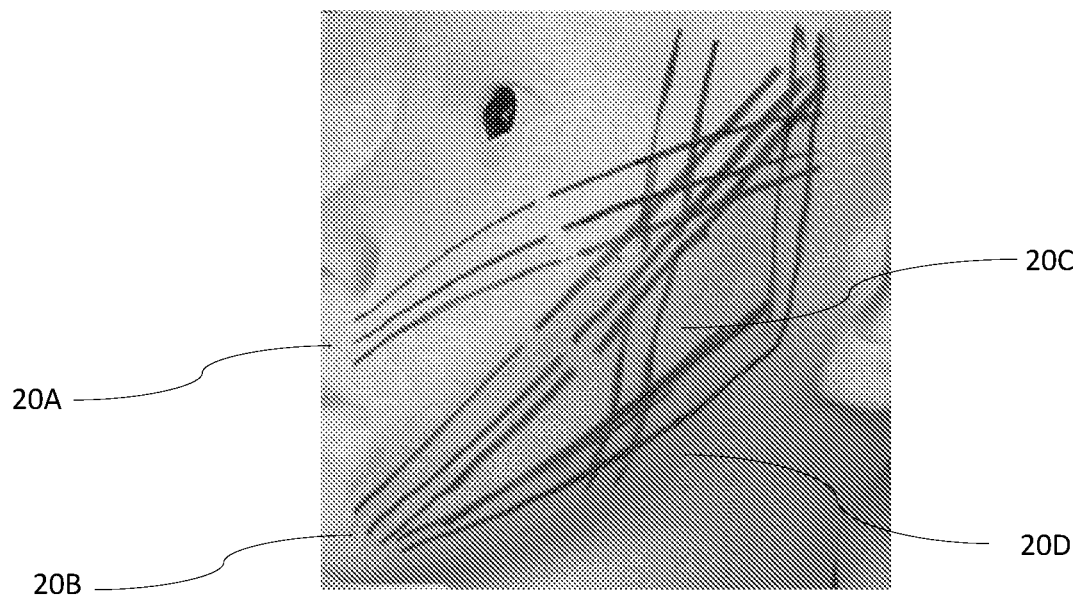
FIGS. 20A to 20D are schematic views illustrating patterns of marking layout and arrangement of ten facelift suture path lines on each half face of a user according to the preferred embodiment of the present invention.

Referring to FIG. 20A, an alternative mode of the facelift suture path line marking layout and arrangement as shown in FIG. 19A is illustrated, wherein one more mid facelift suture path line 20B is marked parallelly in general so that three mid facelift sutures 10 (as shown in FIG. 1) are implanted along the three mid facelift suture path lines 20B to enhance the suspension and lifting effects to the cheek and temple portions of the user and the ability of reducing of marionette line of the user.

Figure 20B:
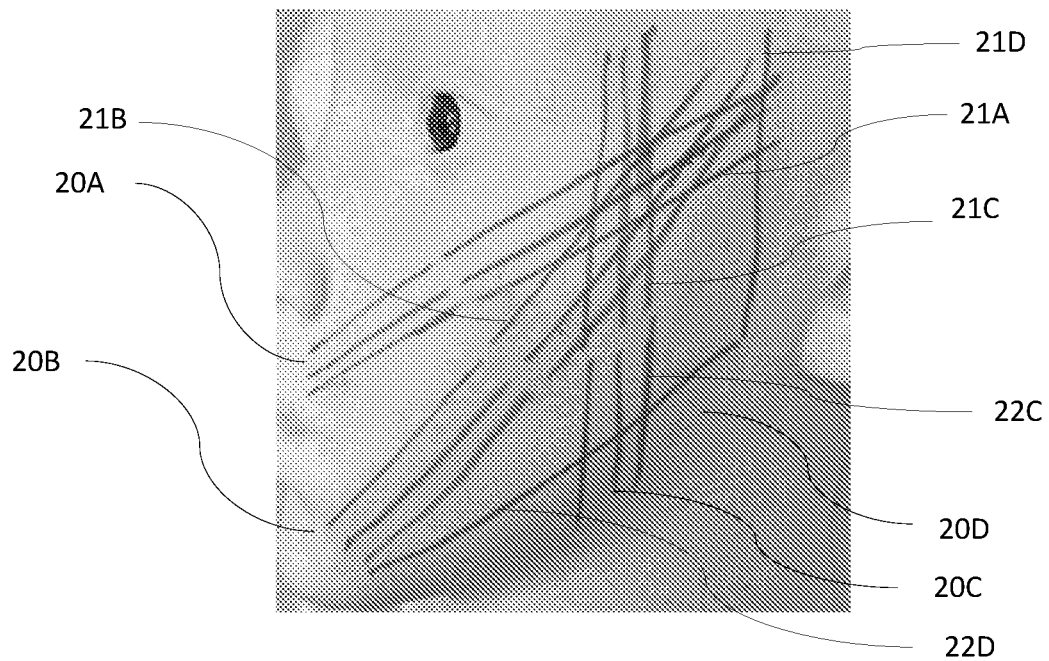

Referring to FIG. 20B, three front facelift suture path lines 20A, three mid facelift suture path lines 20B, three side facelift suture path lines 20C and one jawline facelift suture path line 20D are marked on each half face of the user who has deeper nasolabial fold and marionette line and more severe cheek sagging problems with less jawline sagging condition. The three front facelift suture path lines 20A are marked parallelly in general and extended upwardly, rearwardly and inclinedly from the nasolabial fold to cheek portion and then the temple portion of the user. The three mid facelift suture path lines 20B are marked parallelly in general and extended upwardly, rearwardly and inclinedly from marionette line to the cheek portion and then the temple portion of the user, which three upper segments 21B are intersected with the three upper segments 21A of the three front facelift suture path lines 21A at the cheek portion of the user. The three side facelift suture path lines 20C are marked in parallelly in general and extended upwardly from the jowl position to the crows feet portion of the user, which three upper segments 21C are intersected with the three upper segments 21A of the three front facelift suture path lines 20A and then the two upper segments 21B of the two mid facelift suture path lines 20B. The three upper segments 21B of the three front, mid and side facelift suture path lines 20A, 20B 20C are intersected at the cheek and/or temple portion of the user for guiding a total of nine facelift sutures 10 (as shown in FIG. 1) intersecting at the cheek and/or temple portion to provide firmer and plumper effects to the cheek and/or temple portion of the user while enhancing the lifting and reducing of the nasolabial fold and marionette line. Accordingly, such facelift suture path line marking layout and arrangement is specifically preferred for the user who has deeper nasolabial fold, marionette line and crows feet and more severe cheek or temple sagging problems by providing more intersecting invasive sutures 10 (as shown in FIG. 1) around cheek and temple portions of the user that is significantly good for upward and rearward lifting the facial tissue at the cheek and temple portions of the user to tighten the cheek and reduce crows feet effectively while the three front facelift sutures 10 (as shown in FIG. 1) being implanted along the three front facelift suture path lines 20A and the three mid facelift sutures 10 (as shown in FIG. 1) being implanted along the three mid facelift suture path lines 20B enhance the reducing of nasolabial fold and the marionette line respectively. The three side facelift sutures 10 (as shown in FIG. 1) to be implanted along the three side facelift suture path lines 20C substantially enhance the uplifting and fixing effects to the lower segment of the jawline facelift suture 10 (as shown in FIG. 1) implanted along the lower segment 22D of the jawline facelift suture path line 20D for lifting the jowl portion and reshaping the face plate of the user.

Figure 20C:
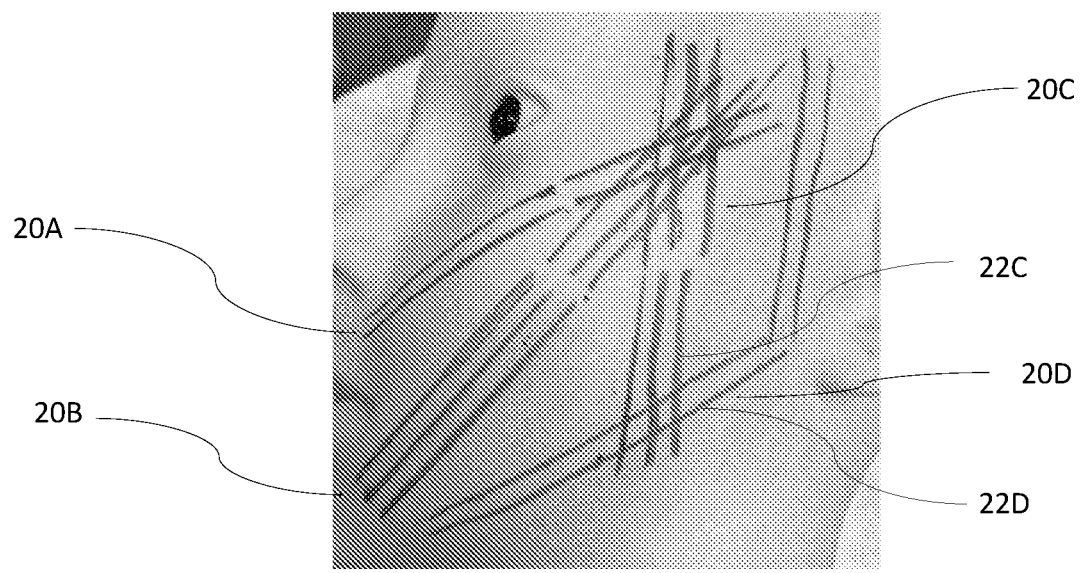

Referring to FIG. 20C, an alternative mode of facelift suture path line layout and arrangement as shown in FIG.

20B is illustrated, wherein only two front facelift suture path lines 20A is marked and two jawline facelift suture path lines 20D are marked. Such facelift suture path line layout and arrangement is adapted for user who has more severe jowl sagging problem and a lesser nasolabial fold, wherein the lower segments 22D of the two jawline facelift suture path lines 20D are intersected with the lower portions of the three lower segments 22C of the three side facelift suture path lines 20C. The upper segments 21A, 21B, 21C of the two front facelift suture path lines 20A, the three mid facelift suture path lines 20B and the three side facelift suture path lines 20C are intersected at the cheek or temple portion of the user. Such facelift suture path line marking layout and arrangement is specifically preferred for the user who has deeper marionette line and crows feet and more severe jawline sagging problems by providing a pair of jawline facelift sutures 10 (as shown in FIG. 1) implanted along the two jawline facelift suture path lines 20D that substantially enhances the uplifting and fixing effects to the jawline by reinforcing the lifting of the jowl portion to reshape the face plate of the user.

Figure 20D:
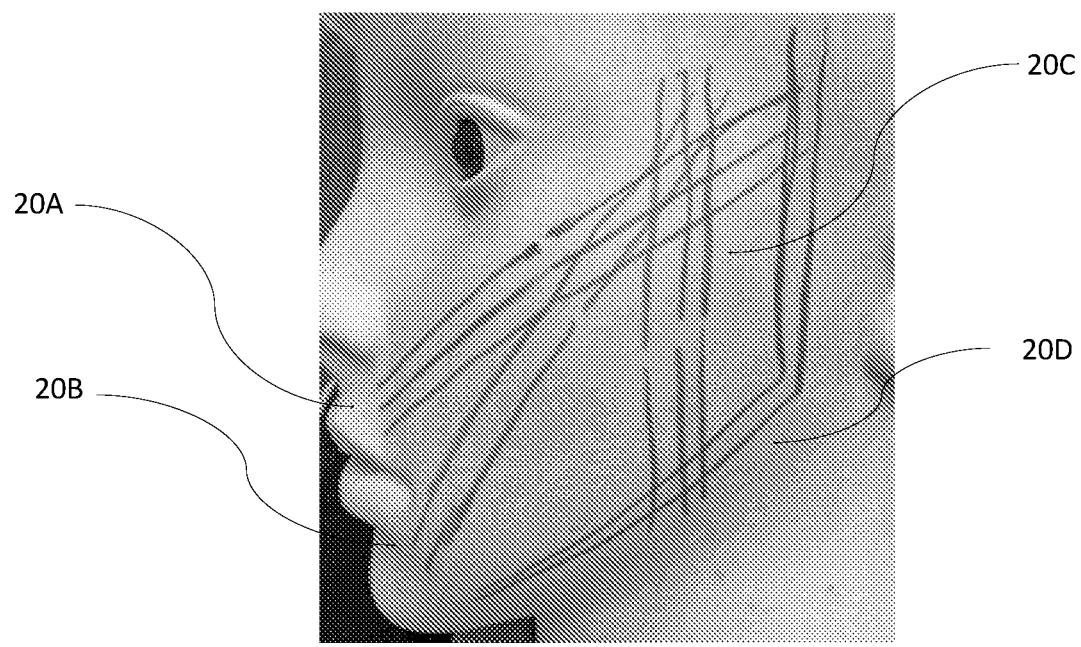

Referring to FIG. 20D, an alternative mode of facelift suture path line marking layout and arrangement as shown in FIG. 19E is illustrated, wherein one more side facelift suture path line 20C is marked such that three side facelift sutures 10 are implanted along the three side facelift suture path lines 20C to provide a firmer and plumper cheek portion of the user and enhance the uplifting and fixing effects to the two jawline facelift sutures 10 (as shown in FIG. 1) implanted along the two jawline facelift suture path lines 20D that can reinforce the lifting of the jowl portion to reshape the face plate of the user.

It is appreciated that the facelift suture path line marking layout and arrangement as illustrated in FIGS. 16A to 20D provides basic guideline for the implant of invasive sutures 10 accordingly, wherein fine adjustments including the exact position of each facelift suture path line 20, the distance between each two facelift suture path lines 20, the inclination between each two facelift suture path lines 20, the location of the intersection of the facelift suture path lines 20, the position of the insertion mark 23 of each facelift suture path line 20, and the position of the end or outlet mark 211, 221 of each segment of each facelift suture path line 20 are determined by the user and the operator for preferred suspension and lifting effects according to the actual facial and skin condition of the user. According to the preferred embodiment of the present invention, the following guidelines, but not limited to, should be noted and determined:

(a) The end or outlet mark 221 of each of the front and mid facelift suture path lines 20A, 20B should be extended passing through any fold or line would like to be reduced, such as the nasolabial fold or marionette line, correspondingly.

(b) The insertion mark 23 is preferred to be located at a position with relatively thicker subcutaneous tissue layer of the skin that is thick enough to allow the point end of the needle 11, 12 to turn from a perpendicular insertion direction to a horizontal penetration direction.

(c) The intersection of every two or three facelift suture path lines 20 is preferred to be location at a position that the subcutaneous tissue layer is thick enough to allow the corresponding two or three facelift sutures 10 being implanted intersectingly without contacting with each other.

(d) The more sagging area of the user's face, the more intersecting of facelift suture path lines 20.

(e) The inclined angle of the facelift suture path line should be aligned as perpendicular with the folds or lines as possible and passing through the sagging area of the user's face, so as to provide more effective and efficient suspending and lifting ability to the invasive sutures 10 implanted therealong.

(f) Every two front, mid, side, or jawline facelift suture path lines do not need to be aligned in absolute parallel manner, wherein the co-relationship of the skin tissue between the two adjacent extending facelift suture path lines should be taken into account for providing desired suspension, fixing and lifting effects to the invasive sutures 10 implanted therealong.

Figure 21:
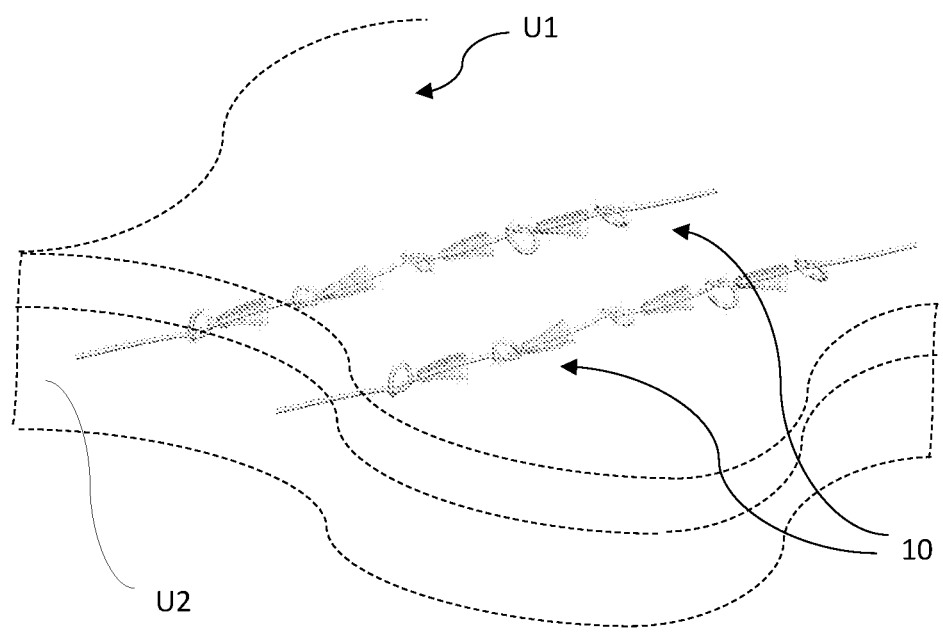
FIG. 21 is a perspective schematic view illustrating the arrangement of two parallel invasive sutures in the subcutaneous tissue layer of the user's skin according to the preferred embodiment of the present invention.

In the procedure (C), referring to FIGS. 12A to 12T, each of the facelift invasive sutures 10 is implanted along the corresponding front, mid, side or jawline facelift suture path line 20A, 20B, 20C, 20D, wherein each facelift suture 10 is implanted according to the following steps:

(C1) Determine the order of the facelift suture path lines 20A, 20B, 20C, 20D to be implanted with the invasive sutures 10 according to the facial and skin condition of the user referencing the following guidelines as example:

(C1-1) if the nasolabial fold is obvious and the cheek sagging is not obvious to the user, place the invasive sutures 10 along the front facelift suture path lines 20A first;

(C1-2) if the marionette line(s) or the cheek sagging is relatively more obvious, place the invasive sutures 10 along the mid facelift suture path lines 20B first;

(C1-3) if the crows feet or the jowl sagging is relatively more obvious, place the invasive sutures 10 along the mid facelift suture path lines 20C first;

(C1-4) for preventive treatment as shown in FIGS. 16A to 16C, since the aging sagging is relatively mild, the placement of the invasive sutures 10 along the pair of side facelift suture path lines 20C is preferred to be performed after the placement of the invasive sutures 10 along the front and the mid facelift suture path lines 20A, 20B;

(C1-5) for anti-aging treatment as illustrated in FIGS. 17A to 17C, the placement of the invasive sutures 10 along the front and the mid facelift suture path lines 20A, 20B can be performed after the placement of the side facelift suture path lines 20C and/or the placement of the jawline facelift suture path line 20D;

(C1-6) for treatment for tighter and plumper face as illustrated in FIGS. 18A to 18F, the placement of the invasive sutures 10 can be performed firstly to the more obvious fold or line or more aging sagging facial portion;

(C1-7) for treatment for user having large face plate as illustrated in FIGS. 19A to 20D, the placement of the invasive sutures 10 along the jawline facelift suture path line(s) 20D can be preformed prior to the placement of the invasive sutures 10 along the front, the mid and the side facelift suture path lines 20A, 20B, 20C, and then, the placement of the invasive sutures 10 along the side facelift suture path lines 20C can be performed before the placement of the invasive sutures 10 along the front and the mid suture path lines 20A, 20C;

(C1-8) place invasive suture 10 to specific facelift suture path line 20 marked on the face of the user having relatively thinner skin tissue than that of other facelift suture path lines 20;

(C1-9) the placement of the adjacent invasive sutures 10 such as along the two or three front, mid or side facelift suture path lines 20A, 20B, 20C are preferred to be placed about the same deep of the subcutaneous tissue layer U2 of the user's facial skin U1, as shown in FIG. 21;

(C1-10) the placement of two or three intersecting invasive sutures 10, the invasive suture 10' to be placed first should be underlaid closer to the skin surface and the invasive suture 10" to be placed later should be underlaid deeper than the firstly placed invasive suture 10', as shown in FIG. 22, wherein according to the preferred embodiment of the present invention, the deeper invasive suture 10" is spacedly underlaid in the subcutaneous tissue layer and intersecting with the firstly placed invasive suture 10' without contacting with each other; and (C1-11) at the intersection portion U3 of every two invasive sutures 10 should not be in contact with each other, preferably overlapping spacedly the two flexible thread bodies (threads) 13 of the two invasive sutures 10, and to avoid the overlapping of the frusto-conically shaped tissue engaging elements 14 and the thread nodes 133, as shown in FIG. 22.

(C2) Determine which path line of the front, mid or side facelift suture path lines 20A, 20B, 20C to be placed and introduced with invasive suture 10 first according to the following guidelines:

(C2-1) generally place invasive suture along the path line closer to the ear of the face of the user for each of the front, mid or side facelift suture path lines 20A, 20B, 20C;

(C2-2) the portion of the face tissue along the front, mid or side facelift suture path lines 20A, 20B, 20C having more obvious sagging and drooping condition should be placed with invasive suture 10 correspondingly first; and (C2-3) place invasive suture to the facelift suture path line 20 marked on the face of the user having relatively thinner subcutaneous tissue than that of the other facelift suture path line 20 of the front, mid or side facelift suture path lines 20A, 20B, 20C.

(C3) Determine which facelift suture path line 20 of the intersecting facelift suture path lines 20, as illustrated in the intersection area (IA) in FIG. 16A and the intersection portion in FIG. 22, to be placed with the invasive suture 10 in an upper position than the other according to the following guidelines:

(C3-1) the invasive suture 10 placed along the corresponding facelift suture path line 20 will be pulled to lift the skin tissue first as major suspension and lifting of a desired portion of the face of the user, such that the pulling of the invasive sutures 10 placed below the first pulling invasive suture 10 will become a fine adjustment of the desired portion of the face of the user.

(C4) Determine to place the upper segment 101 or the lower segment 102 of each of the invasive sutures 10 first and then the other. Generally, the upper segment 101 of the invasive suture 10 is placed in the subcutaneous tissue layer underlying the upper segment 21 of the corresponding facelift suture path line 20 and then the lower segment 102 of the invasive suture 10 is placed in the subcutaneous tissue layer underlying the lower segment 22 of the corresponding facelift suture path line 20. For some situations, such as the user and operator would like to fix and suspend the sagging jowl portion or to fix and lift the fold or line first, the lower segment 102 of the invasive suture 10 can be placed in the subcutaneous tissue layer underlying the lower segment 22 of the facelift suture path line 20 before the placement of the upper segment 101 of the invasive suture 10.

(C5) Implant of the invasive sutures 10 along the facelift suture path lines 20 marked on the user's face, including the following steps:

(C5-1) For example, insert a pointed end of a first needle 11 into a subcutaneous tissue layer of a facial skin of the user at the insertion mark 23 of one of the facelift suture path lines 20A, 20B, 20C, as shown in FIG. 12A. A hole can be premade at the insertion mark 23 by a hole punching gauge for the first needle 11 to insert. Although the preferred deep of the invasive suture 10 to be placed is at least 3 mm to about 3 mm under the skin surface, the preferred insertion depth of the first needle 11 is the operator's finger touching on the skin may still feel the pointed end of the first needle 11 in the subcutaneous tissue layer.

(C5-2) Rotate the first needle 11 for a predetermined angle to be inclined with respect to the facial skin surface, as shown in FIGS. 3B to 3D and FIGS. 12B and 12J, to prepare for insertion of the first needle 11 into the subcutaneous tissue layer by extruding the adjacent facial skin to raise through the inclined first needle 11.

(C5-3) Continuously insert the first needle 11 into the subcutaneous tissue layer until general parallel to the subcutaneous tissue layer, as shown in FIGS. 3F to 3G and FIGS. 12C to 12G, and stab the pointed end of the first needle 11 out of the facial skin of the user at a position of the end or outlet mark 211 of the upper segment 21 of the corresponding facelift suture path line 20, as shown in FIGS. 3H to 3I and FIGS. 12O to 12P, whereas a protective tube T1 is placed at the end or outlet mark 211 of the upper segment 21 of the facelift suture path line 20.

According to the preferred embodiment of the present invention, during the insertion of the first needle 11 by the dominant hand of the operator, the user is preferred to use his or her other hand to touch along the respective upper segment 21 of the facelift suture path line 20 with a slight pressure to feel the inserting needle 11 and the depth of the needle 11 as shown in FIG. 12M, wherein to thinner subcutaneous tissue layer that the first needle 11 penetrating through, the operator may press and squeeze to extruding the tissue around the first needle 11 to raise for ease of precisely penetrating the first needle 11 therethrough, as shown in FIGS. 12K to 12L, which is essential for ensuring there is enough tissue for the first needle 11 to pass through but also increase the suspension and lifting effect by ensuring the frusto-conical shaped tissue engaging elements 14 engaged with enough surrounding tissue. At the end or outlet mark 211 of the upper segment 21 of the facelift suture path line 20, the opening of the protective tube T1 is preferred to press against the skin surface that allows the pointed end of the first needle 11 to precisely insert into the protective tube T1 for protection from being contact with the operator and help the first needle 11 to stab out from the skin surface too.

(C5-4) Pull the elongated flexible thread body 13 until the first section of the frusto-conically shaped tissue engaging elements 14 distributed along the upper segment 11 of the invasive suture 10 is pulled and distributed in the subcutaneous tissue layer underlying the upper segment 21 of the corresponding facelift suture path line 20, as shown in FIGS. 3J to 3L and FIGS. 12G, 12H and 12N, wherein the narrow ends of the first section of the tissue engaging elements 14 are directed to the first needle 11.

Figure 3A:
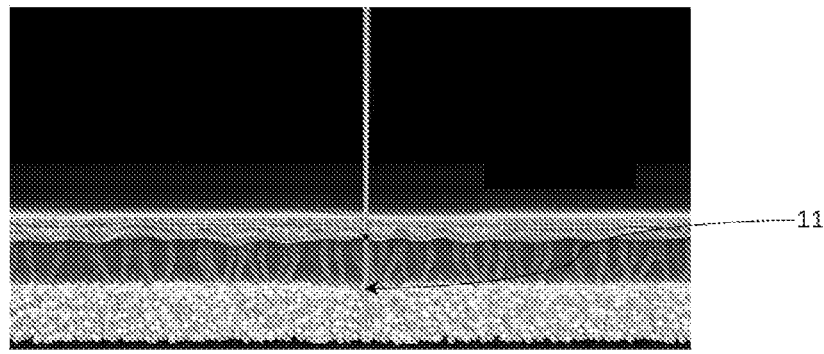
FIG. 3A to FIG. 3Y are schematic views illustrating the steps of placing an invasive suture in the skin tissue.
Figure 3B:
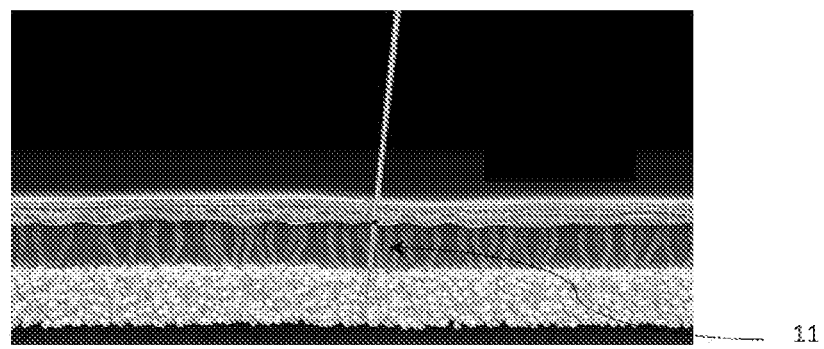
Figure 3C:
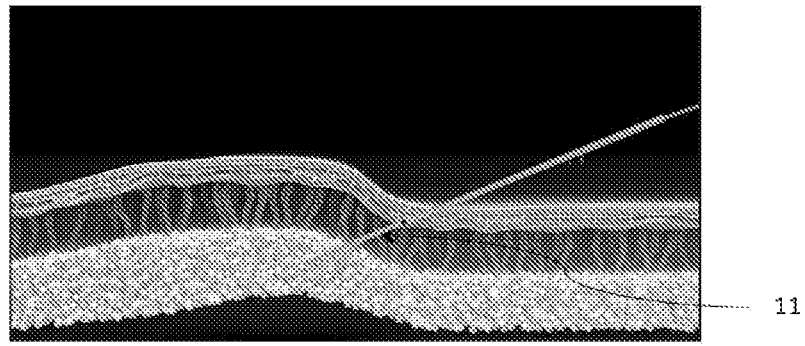
Figure 3D:
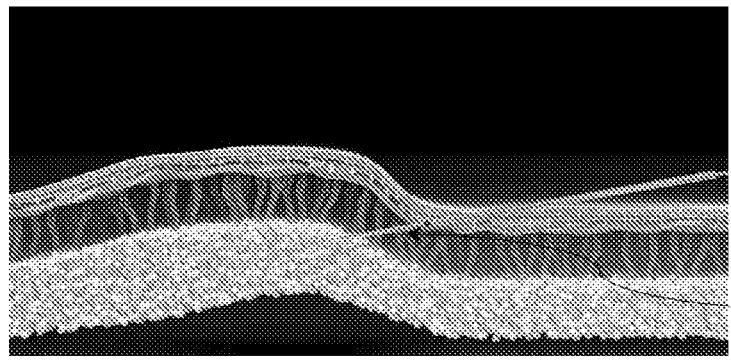
Figure 3E:
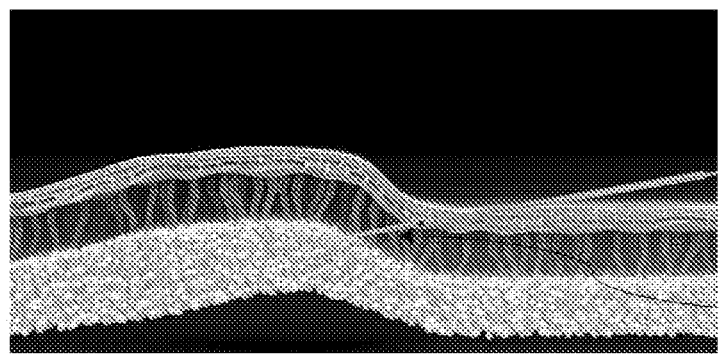
Figure 3F:
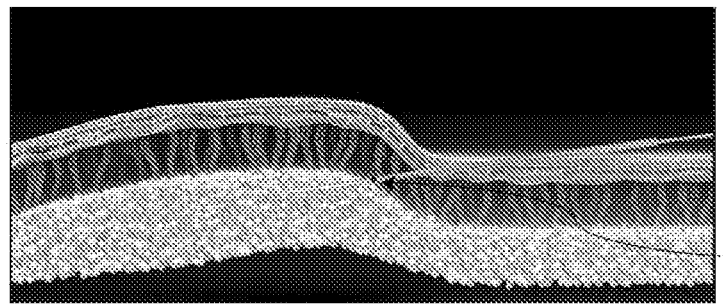
Figure 3G:
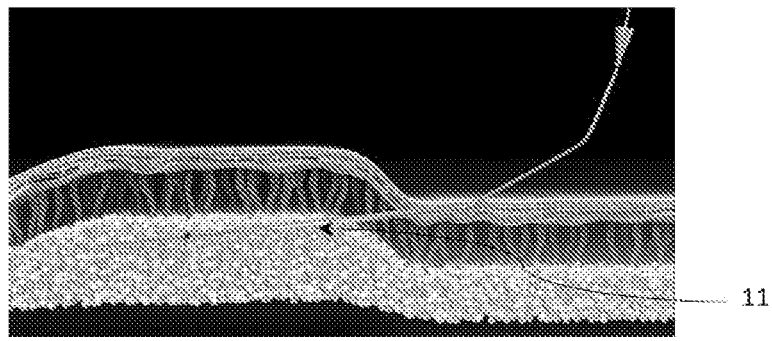
Figure 3H:
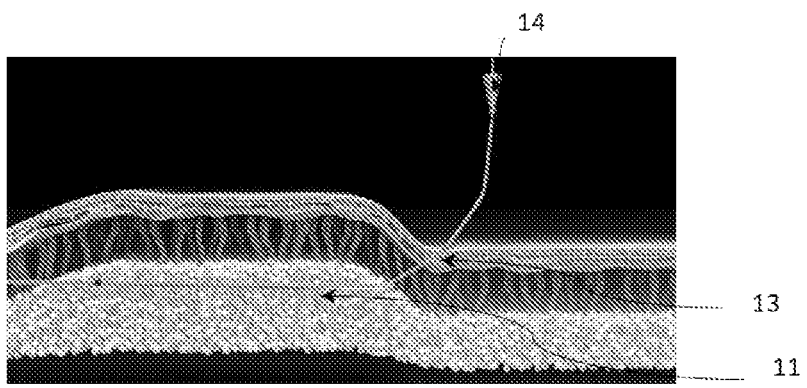
Figure 3I:
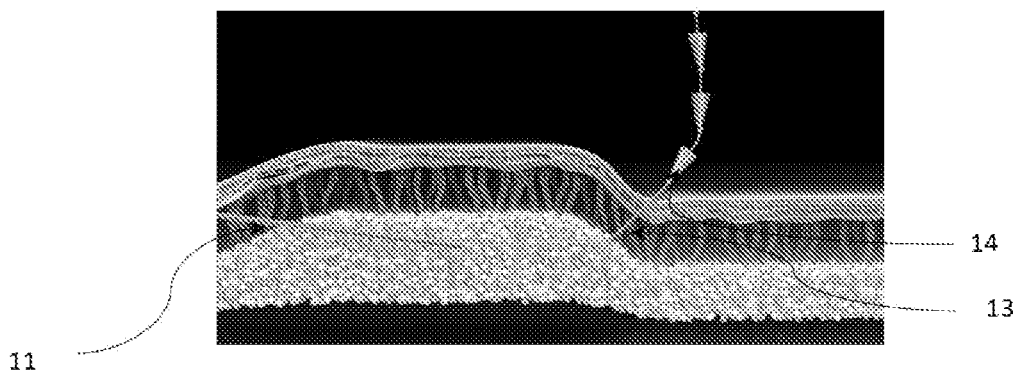
Figure 3J:
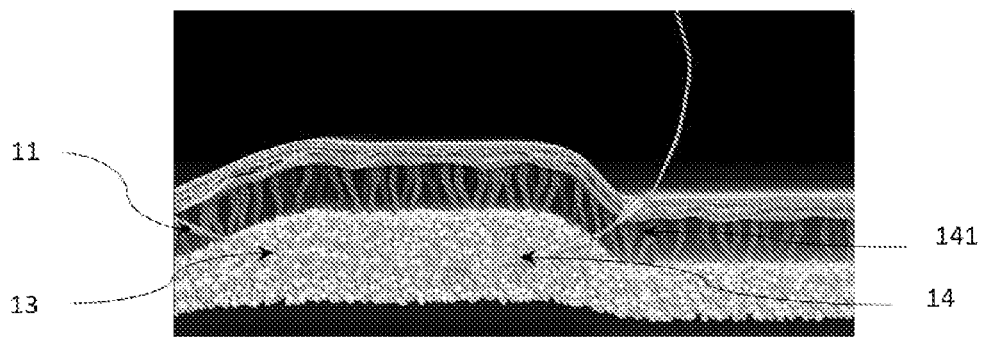
Figure 3K:
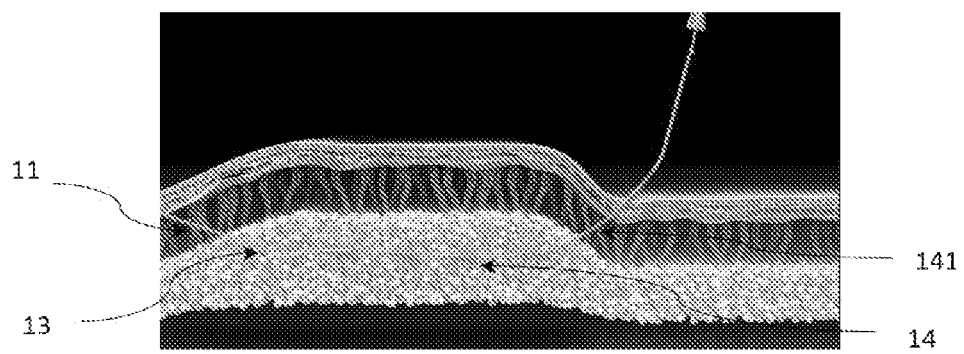
Figure 3L:
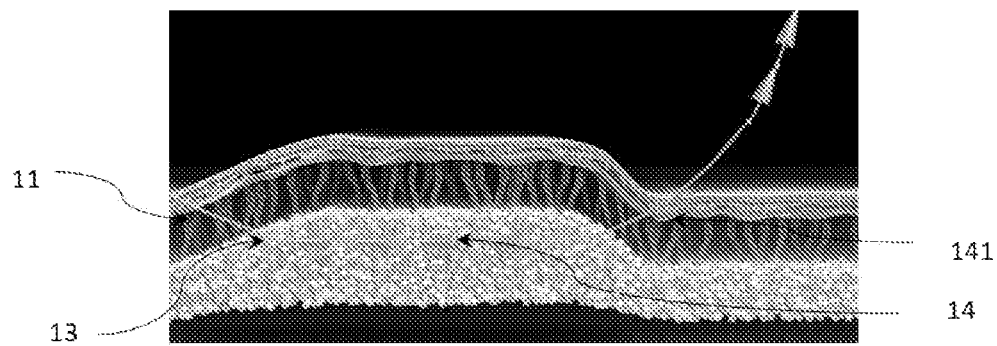
Figure 3M:
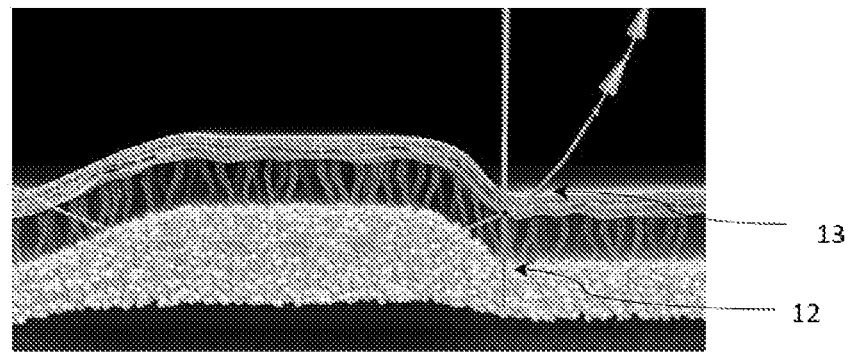
Figure 3N:
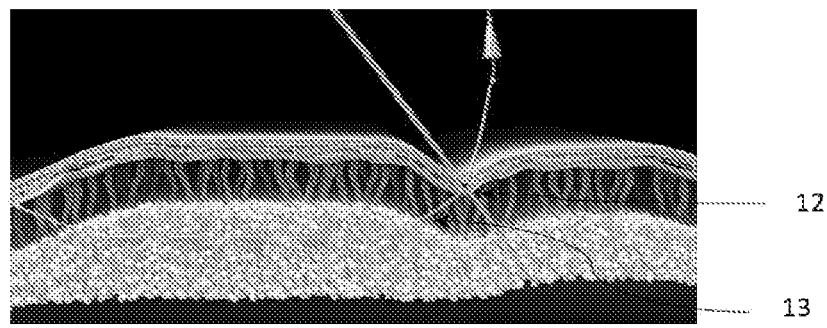
Figure 3O:
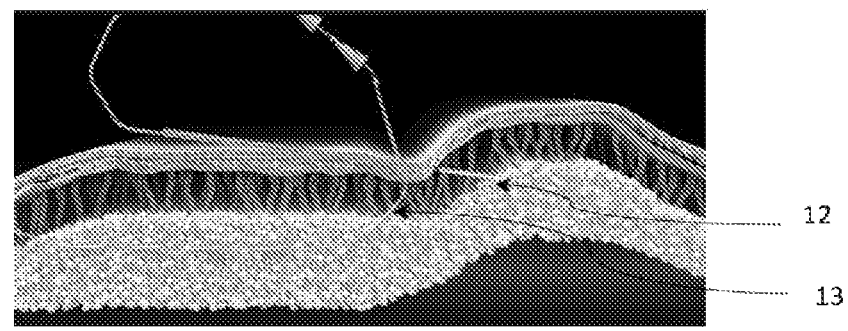
Figure 3P:
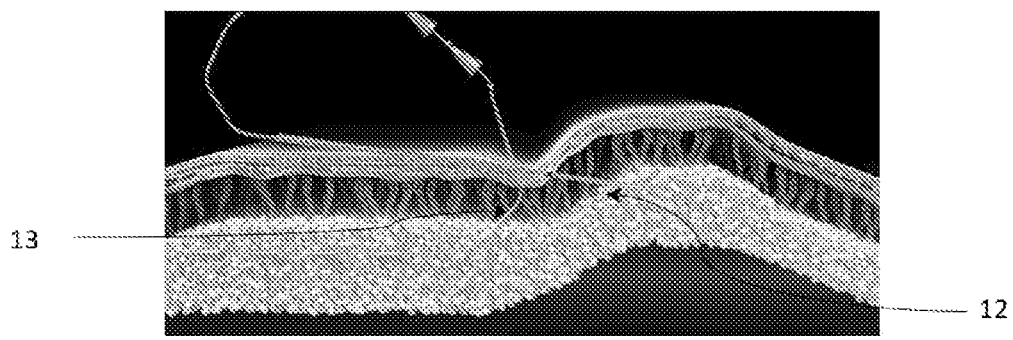
Figure 3Q:
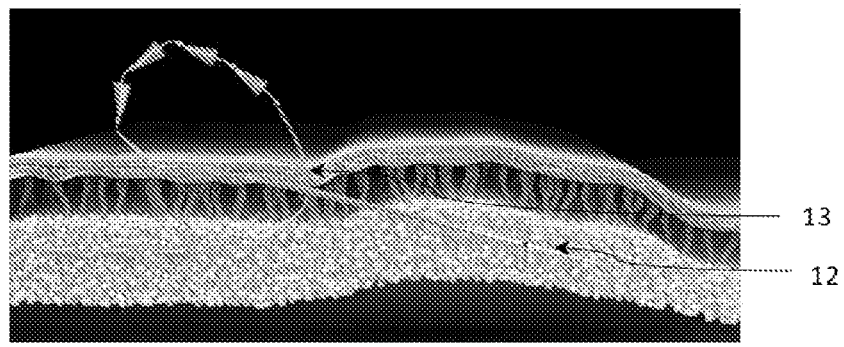
Figure 3R:
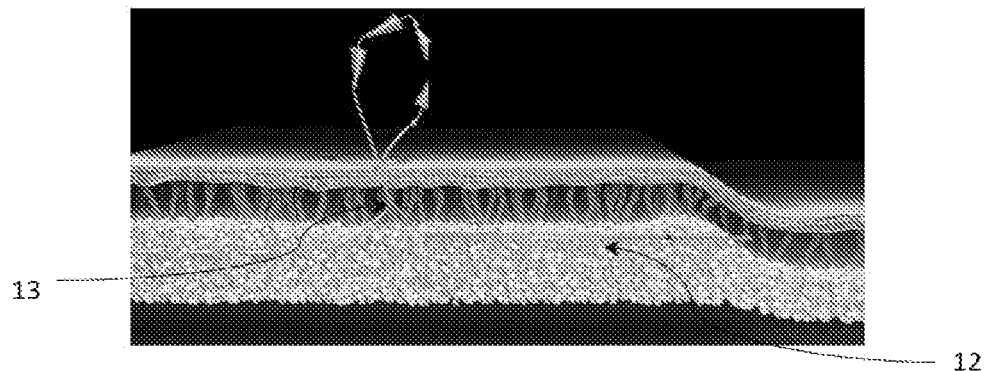
Figure 3S:
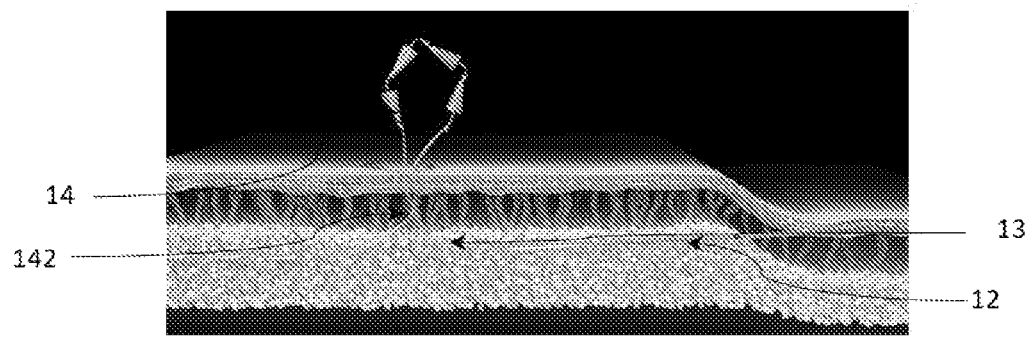
Figure 3T:
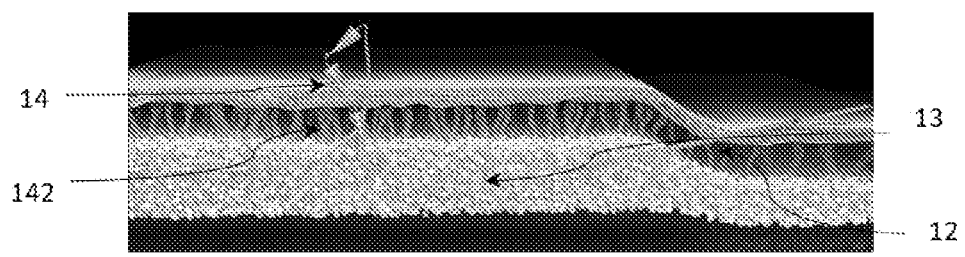
Figure 3U:
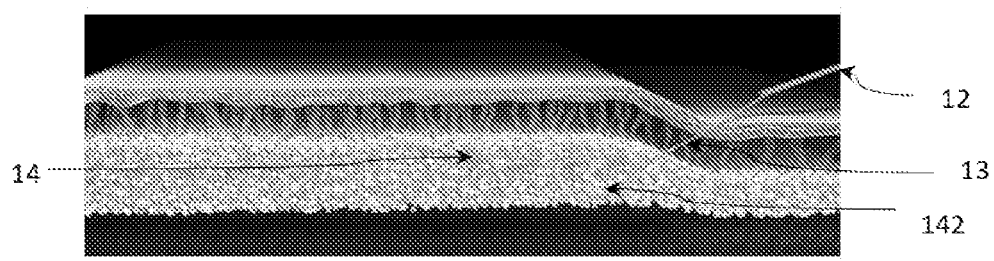
Figure 3V:
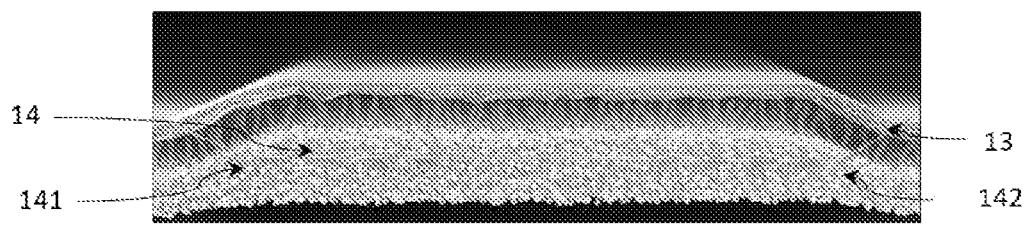
Figure 3W:
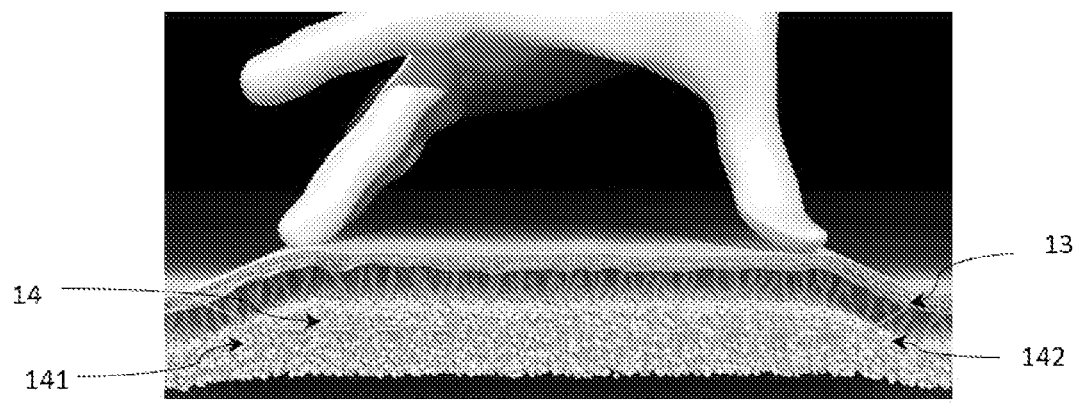
Figure 3X:
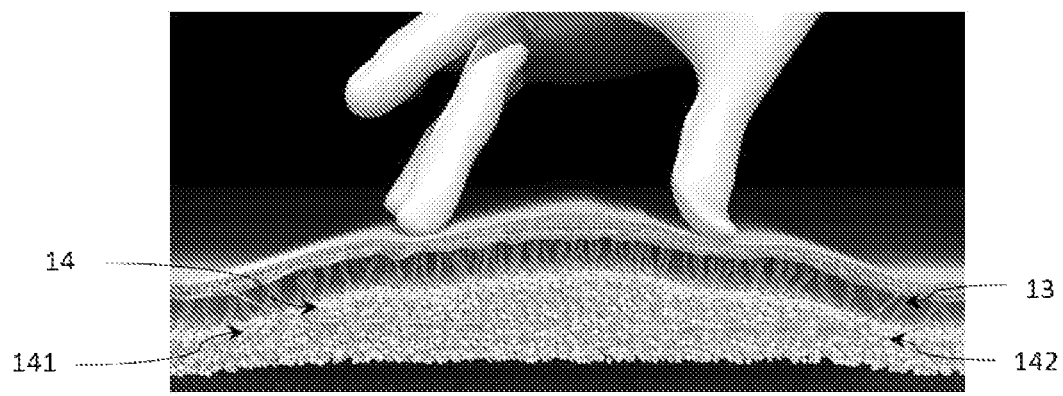
Figure 3Y:
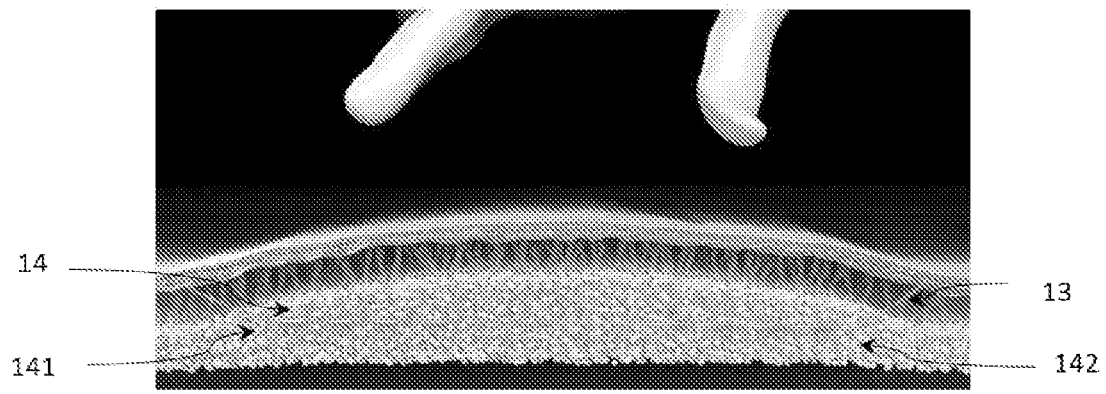

(C5-6) After the upper segment 101 of the invasive suture 10 is placed underlying the upper segment 21 of the facelift suture path line 20, insert the pointed end of the second needle 12 into the subcutaneous tissue layer of the facial skin at the same insertion mark 23 of the same facelift suture path line 20 that the upper segment 101 of the invasive suture 10 placed, that is inserting the pointed end of the second needle 12 through the same hole of the first needle 11 inserted into the skin surface, as shown in FIG. 3M and FIG. 12I, until the second needle 12 penetrates through the stratum corneum layer and the pigment layer and is positioned in the subcutaneous tissue layer.

(C5-7) Like the first needle 11, rotate the second needle 12 for a predetermined angle to be inclined with respect to the facial skin surface, as shown in FIGS. 3N to 3P and FIG. 12J, to prepare for insertion of the second needle 12 into the subcutaneous tissue layer by extruding the adjacent facial skin to raise through the inclined second needle 12.

(C5-8) Continuously insert the second needle 12 into the subcutaneous tissue layer until general parallel to the subcutaneous tissue layer, as shown in FIGS. 3F to 3G, and stab the pointed end of the second needle 12 out of the facial skin of the user at a position of the end or outlet mark 221 of the lower segment 22 of the corresponding facelift suture path line 20, as shown in FIGS. 3H to 3I, whereas a protective tube T1 is placed at the end or outlet mark 221 of the lower segment 21 of the facelift suture path line 20.

According to the preferred embodiment of the present invention, during the insertion of the second needle 11 by the dominant hand of the operator, the user is preferred to use his or her other hand to touch along the respective upper segment 22 of the facelift suture path line 20 with a slight pressure to feel the inserting needle 12 and the depth of the second needle 12, wherein to thinner subcutaneous tissue layer that the second needle 12 penetrating through, the operator may press and squeeze to extruding the tissue around the second needle 12 to raise for ease of precisely penetrating the second needle 12 therethrough, that is essential for ensuring there is enough tissue for the first needle 11 to pass through but also increase the suspension and lifting effect by ensuring the frusto-conical shaped tissue engaging elements 14 engaged with enough surrounding tissue. At the end or outlet mark 221 of the lower segment 22 of the facelift suture path line 20, the opening of the protective tube T1 is preferred to press against the skin surface that allows the pointed end of the second needle 12 to precisely insert into the protective tube T1 for protection from being contact with the operator and help the second needle 12 to stab out from the skin surface too.

(C5-9) Pull the elongated flexible thread body (thread) 13 until the second section of the frusto-conically shaped tissue engaging elements 14 distributed along the lower segment 12 of the invasive suture 10 is pulled and distributed in the subcutaneous tissue layer underlying the lower segment 22 of the corresponding facelift suture path line 20, as shown in FIGS. 3J to 3L, wherein the narrow ends of the second section of the tissue engaging elements 14 are directed to the second needle 12.

(C5-10) Distribute the frousto-conically shaped tissue engaging elements 14 of the first segment 101 and second segment 102 of the invasive suture 10 placed along the upper segment 21 and second segment 22 of the facelift suture path line 20 respectively. According to the preferred embodiment of the present invention, each of the frousto-conically shaped tissue engaging elements 14 is movably mounted between two adjacent nodes 133 and each frousto-conically shaped tissue engaging element 14 can be fine adjusted between the two adjacent nodes 133 to the desired position for tightening the underlying tissue around the frousto-conically shaped tissue engaging elements 14 for effectively suspension and lifting effects of the subcutaneous tissue through straddling, pushing, pressing, squeezing and extruding the skin tissue, as shown in FIGS. 12Q to 12S.

(C6) After the invasive sutures 10 are implanted, remove the first and second needle 11, 12 from the invasive suture 10 successfully placed in the subcutaneous tissue layer underlying the corresponding facelift suture path line 20, as shown in FIG. 12T.

For better operation with the implanted invasive sutures 10, it is preferred to remove the marking of all the facelift suture path lines 20 before the procedure (D) and then preform another sterilization for the user's face, as shown in FIG. 13.

In the procedure (D), referring to FIGS. 14A to 14H, according to the preferre embodiment of the present invention, the facelifting and tightening of the user can be performed according to the following steps:

(D-1) Adjust the upper segment 101 and the lower segment 102 of each of the implanted invasive sutures 10 separately by slightly pulling and tightening the elongated end portion of each of the upper segment 101 or lower segment 102 extended out of the user's skin.

Figure 14A:
FIGS. 14A to 14H are schematic view illustrating the facial shaping with the implanted invasive sutures according to the above preferred embodiment of the present invention.

(D-2) Selectively adjust the lower segment 102 or the upper segment 101 of the implanted suture 10 first, or vice verse. According to the preferred embodiment, prefer to adjust the lower segment 102 of each of the implanted suture 10 first to ensure the lowest frusto-conically shaped tissue engaging element 14 is positioned in the desired position and engaged with the surrounding tissue by pulling the thread body 13 of the lower segment 102 and/or the upper segment 101 while using a thumb to press on the flexible thread body 13 where just penetrated out of the skin surface, as shown in FIGS. 14A to 14B.

Figure 14B:

(D-3) Rub the skin tissue upwardly along the lower segment 102 of the implanted suture 10 until desired shape and condition is occurred by distributing the frusto-conically shaped tissue engaging elements 14 to engage and tighten the underlying tissue, as shown in FIG. 14B.

Figure 14C:
Figure 14D:
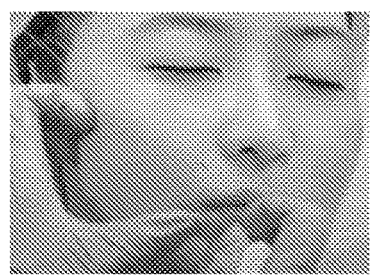
Figure 14E:
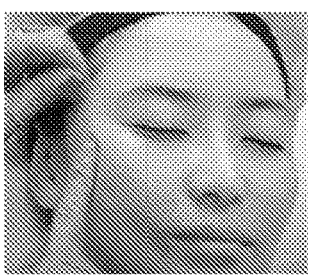
Figure 14F:
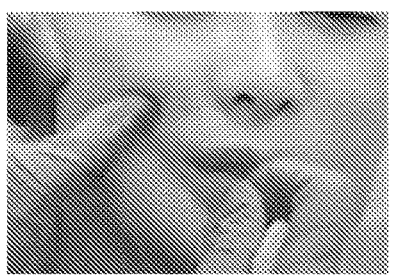
Figure 14G:
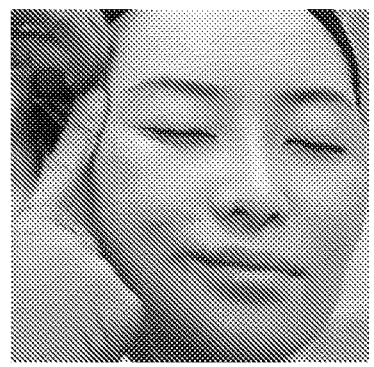
Figure 14H:

(D-4) adjust the upper segment 101 of the implanted suture 10 with its lower segment 102 being adjusted by pulling upwardly the thread body 13 of the upper segment 101 penetrated out of the skin surface to tighten the implanted suture 10 and distribute the frusto-conical shaped tissue engaging elements 14 of the upper segment 101, as shown in FIG. 14C.

(D-5) Rub the skin tissue upwardly along the upper segment 101 of the implanted suture 10 until desired shape and condition is occurred by distributing the frusto-conically shaped tissue engaging elements 14 to engage and tighten the underlying tissue.

(D-6) Adjust both the upper and lower segments 101, 102 of each of the implanted invasive sutures 10 to achieve a smoother and firmer skin surface along the implanted invasive suture 10 by gradually pulling the thread body 13 while straddling, pushing, pressing, squeezing, shoving, extruding, and/or caressing the facial skin and tissue around the implanted suture 10, as shown in FIGS. 14D to 14H.

(D-7) After all invasive sutures 10 are implanted in position in the desired subcutaneous tissue layer of the user's facial skin, slightly adjust and tighten (below 100% tightness) the implanted suture(s) for the portion the needs desired improvement the most, for example the front facelift sutures 10 implanted along the two or three front facelift suture path lines 20A for reducing nasolabial fold. Then, adjust and tighten the implanted suture(s) 10 for portion that needs desired improvement the second, for example the mid facelift sutures 10 implanted along the two or three mid facelift suture path lines 20B for reducing marionette line. Thereafter, adjust and tighten the other implanted suture(s) 10 in desired order. After such initial adjustment, observe the suspension and lifting result of the user and further adjust and tighten the corresponding implanted sutures 10 to prefect the facelifting result until satisfactory.

(D-8) The pulling and tightening of each of the implanted sutures 10 are preferred to gradually perform for once the most tightness of the implanted suture 10 is achieved, the further pulling may break the thread body 13.

(D-9) For intersecting implanted sutures 10, as illustrated in FIG. 22, the two intersecting implanted sutures 10 are spacedly overlapped without contacting with each other. Practically, neither the thread body 13, the frusto-conical shaped tissue engaging element 14 nor the node 133 of one implanted suture 10 can contact with any of the thread body 13, the frusto-conical shaped tissue engaging element 14 and the node 133 of another implanted suture 10 of the user. The adjusting and tightening of the intersecting implanted sutures 10 should be performed firstly with the implanted suture 10' positioning closest to the skin surface, and the last one to be adjusted and tighten should be the one positioned farest from the skin surface. In other words, adjust and tighten the upper one and then the lower one.

According to the present invention, each of the intersecting invasive sutures 10 provides suspension, lifting and fixing effect in lower and upper directions thereof (single linear dimension) while the other intersecting invasive suture 10 provides suspension, lifting and fixing effect in another two directions (dual plan dimension) underneath the skin surface. At the intersecting area of the two or more intersecting invasive sutures 10, the intersecting invasive suture 10 closer to the skin surface and the intersecting invasive suture 10 in a deeper position provide a suspension, lifting and fixing effect in a perpendicular direction such that a three-dimensional suspension, lifting and fixing effect is applied to the skin tissue of the user.

The procedure (E), referring to FIGS. 15A and 15B, comprises steps of:

(E-1) pulling the end portion of each of the first segment 101 and the second segment 102 of the thread body 13 of each of the implanted sutures 10 until a little bit piercing out of skin surface;

(E-2) removing the residual thread of each of the first segment 101 and second segment 102 of the implanted suture 10 piercing out of the user's skin surface; and (E-3) retracting of the ends of the thread body 13 of each of the implanted sutures 10 into the skin surface while the skin surface is clear from any thread body 13 as shown in FIG. 15B.

The implanted sutures 10 function by simulating the user's own collagen into neocollagenesis production which is achieved by way of fibrosis formation around the implanted sutures 10. After approximately six to nine months from the implant of invasive sutures 10, the implanted sutures are absorbed by the user's body but the fibrosis formed fill and suspend the skin tissue and last two to three years in maximum, depending on the individual health condition of the user.

To achieve even more plumper facial result, after the implant of the invasive sutures 10 according to the treatment method of the present invention, a predetermined amount of hyaluronic acid can be injected into the desired portions of the user's facial skin tissue, such as the tissue around the nasolabial fold, the marionette lines, the crows feet, apple muscle, and etc.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A facial invasive tissue treatment method, comprising steps of:

(i) marking one or more front facelift suture path lines, one or more mid facelift suture path lines and one or more side facelift suture path lines on at least one half face of a user, wherein each of the front, mid and side facelift suture path lines has an upper segment, a lower segment, an insertion mark between the upper segment and the lower segment, and outlet marks at ends of the upper segment and the lower segment, the one or more front facelift suture path lines being extended upwardly, rearwardly and inclinedly, starting from a position of a nasolabial fold to a malar mound and then ending at a position adjacent to an ear of at least the at least one half face of the user while the insertion mark of each of the one or more front facelift suture path lines are positioned around the malar mound, wherein the outlet mark of the lower segment of each of the one or more front facelift suture path lines is extended passing through the nasolabial fold and marked beyond the nasolabial fold, the one or more mid facelift suture path lines being extended upwardly, rearwardly and inclinedly, starting from a position of a marionette line to a cheek and then ending at a position adjacent to a temple portion on the at least one half face of the user while the insertion mark is positioned at the cheek of the user, wherein the outlet mark of the lower segment of each of the one or more mid facelift suture path lines is extended passing through the marionette line and marked beyond the marionette line, the one or more side facelift suture path lines being extended upwardly, starting from a jowl position to a crows feet position on the at least one half face of the user while the insertion mark is positioned below the one or more mid facelift suture path lines;

(ii) implanting invasive sutures in a tissue layer of the at least one half face of the user along and underlying the one or more front facelift suture path lines, the one or more mid facelift suture path lines and the one or more side facelift suture path lines marked on the at least one half face of the user; and (iii) performing facial shaping by tightening the tissue layer through the invasive sutures implanted.

2. The facial invasive tissue treatment method, as recited in claim 1, wherein the step (i) further comprises a step of marking one or two jawline facelift suture path lines, wherein each of the one or two jawline suture path lines has an upper segment, a lower segment, an insertion mark between the upper segment and the lower segment, and outlet marks at ends of the upper segment and the lower segment, wherein the lower segment of each of the one or two jawline facelift suture path lines is marked and extended inclinedly and rearwardly along a jawline of the each half face of the user and the upper segment of each of the one or two jawline facelift suture path lines is marked and extended upwardly along a rear portion of the each half face of the user, starting from a jaw portion to the temple portion of the each half face of the user, wherein the one or more lower segments of the one or more jawline facelift suture path lines are intersected with the lower segments of the side facelift suture path lines and the one or more upper segments of the one or more jawline facelift suture path lines are intersected with at least one of the upper segments of the mid facelift suture path lines and the front facelift suture path lines, and that the step (ii) further comprises a step of implanting one or more invasive sutures in the tissue layer of the at least one half face of the user along and underlying the one or two jawline facelift suture path lines marked on the at least one half face of the user.

3. The facial invasive tissue treatment method, as recited in claim 2, wherein the upper segment of each of the one or more front facelift suture path lines is upwardly, rearwardly and inclinedly extended to intersect with the upper segments of each of the one or more mid facelift suture path lines and each of the one or more side facelift suture path lines.

4. The facial invasive tissue treatment method, as recited in claim 3, further comprising a step of:

(iv) removing residual thread bodies of the first segment and the second segment of each of the invasive sutures implanted piercing out of a skin surface of the at least one half face of the user, wherein each of the invasion sutures comprises a first needle, a second needle, an elongated flexible thread body, a first section of a plurality of frusto-conical shaped tissue engaging elements movably provided along the thread body to form a first segment, and a second section of a plurality of frusto-conical shaped tissue engage elements movably provided along the thread body to form a second segment, wherein the step (ii) further comprises steps of:

(ii-1) adjusting and tightening the upper segment and the lower segment of each of the invasive sutures implanted separately by slightly pulling and tightening an elongated end portion of each of the upper segment and lower segment extended out of the facial skin of the user; and (ii-2) rubbing the facial skin and tissue of the user upwardly along the lower segment of each of the invasive sutures implanted until desired shape and condition are occurred by distributing the frusto-conically shaped tissue engaging elements to engage and tighten the facial skin and tissue of the user.

5. The facial invasive tissue treatment method, as recited in claim 4, wherein the step (ii) further comprises firstly adjusting and tightening one of the invasive sutures which is implanted in an upper position in the skin tissue of the user before adjusting and tightening another one of the invasive sutures which is implanted in a lower position below the one in the upper position.

6. The facial invasive tissue treatment method, as recited in claim 2, wherein the upper segment of each of the one or more mid facelift suture path lines is upwardly, rearwardly and inclinedly extended to intersect with the upper segments of each of the one or more front facelift suture path lines and the one or more side facelift suture path lines.

7. The facial invasive tissue treatment method, as recited in claim 6, further comprising a step of:

(iv) removing residual thread bodies of the first segment and the second segment of each of the invasive sutures implanted piercing out of a skin surface of the at least one half face of the user, wherein each of the invasion sutures comprises a first needle, a second needle, an elongated flexible thread body, a first section of a plurality of frusto-conical shaped tissue engaging elements movably provided along the thread body to form a first segment, and a second section of a plurality of frusto-conical shaped tissue engage elements movably provided along the thread body to form a second segment, wherein the step (ii) further comprises steps of:

(ii-1) adjusting and tightening the upper segment and the lower segment of each of the invasive sutures implanted separately by slightly pulling and tightening an elongated end portion of each of the upper segment and lower segment extended out of the facial skin of the user; and (ii-2) rubbing the facial skin and tissue of the user upwardly along the lower segment of each of the invasive sutures implanted until desired shape and condition are occurred by distributing the frusto-conically shaped tissue engaging elements to engage and tighten the facial skin and tissue of the user.

8. The facial invasive tissue treatment method, as recited in claim 7, wherein the step (ii) further comprises firstly adjusting and tightening one of the invasive sutures which is implanted in an upper position in the skin tissue of the user before adjusting and tightening another one of the invasive sutures which is implanted in a lower position below the one in the upper position.

9. The facial invasive tissue treatment method, as recited in claim 2, wherein each of the one or more side facelift suture path lines is intersected with the one or more mid facelift suture path lines and the one or more front facelift suture path lines.

10. The facial invasive tissue treatment method, as recited in claim 9, wherein the upper segment of each of the one or more side facelift suture path lines is upwardly extended to intersect with upper segment of the one or more mid facelift suture path lines and the one or more front facelift suture path lines.

11. The facial invasive tissue treatment method, as recited in claim 10, further comprising a step of:

(iv) removing residual thread bodies of the first segment and the second segment of each of the invasive sutures implanted piercing out of a skin surface of the at least one half face of the user, wherein each of the invasion sutures comprises a first needle, a second needle, an elongated flexible thread body, a first section of a plurality of frusto-conical shaped tissue engaging elements movably provided along the thread body to form a first segment, and a second section of a plurality of frusto-conical shaped tissue engage elements movably provided along the thread body to form a second segment, wherein the step (ii) further comprises steps of:
(ii-1) adjusting and tightening the upper segment and the lower segment of each of the invasive sutures implanted separately by slightly pulling and tightening an elongated end portion of each of the upper segment and lower segment extended out of the facial skin of the user; and
(ii-2) rubbing the facial skin and tissue of the user upwardly along the lower segment of each of the invasive sutures implanted until desired shape and condition are occurred by distributing the frusto-conically shaped tissue engaging elements to engage and tighten the facial skin and tissue of the user.

12. The facial invasive tissue treatment method, as recited in claim 11, wherein the step (ii) further comprises firstly adjusting and tightening one of the invasive sutures which is implanted in an upper position in the skin tissue of the user before adjusting and tightening another one of the invasive sutures which is implanted in a lower position below the one in the upper position.

13. The facial invasive tissue treatment method, as recited in claim 2, further comprising a step of:
(iv) removing residual thread bodies of the first segment and the second segment of each of the invasive sutures implanted piercing out of a skin surface of the at least one half face of the user,
wherein each of the invasion sutures comprises a first needle, a second needle, an elongated flexible thread body, a first section of a plurality of frusto-conical shaped tissue engaging elements movably provided along the thread body to form a first segment, and a second section of a plurality of frusto-conical shaped tissue engage elements movably provided along the thread body to form a second segment, wherein the step (ii) further comprises steps of:
(ii-1) adjusting and tightening the upper segment and the lower segment of each of the invasive sutures implanted separately by slightly pulling and tightening an elongated end portion of each of the upper segment and lower segment extended out of the facial skin of the user; and
(ii-2) rubbing the facial skin and tissue of the user upwardly along the lower segment of each of the invasive sutures implanted until desired shape and condition are occurred by distributing the frusto-conically shaped tissue engaging elements to engage and tighten the facial skin and tissue of the user.

14. The facial invasive tissue treatment method, as recited in claim 13, wherein the step (ii) further comprises firstly adjusting and tightening one of the invasive sutures which is implanted in an upper position in the skin tissue of the user before adjusting and tightening another one of the invasive sutures which is implanted in a lower position below the one in the upper position.

15. The facial invasive tissue treatment method, as recited in claim 1, wherein the upper segment of each of the one or more front facelift suture path lines is upwardly, rearwardly and inclinedly extended to intersect with the upper segments of each of the one or more mid facelift suture path lines and each of the one or more side facelift suture path lines.

16. The facial invasive tissue treatment method, as recited in claim 1, wherein the upper segment is each of the one or more mid facelift suture path lines is upwardly, rearwardly and inclinedly extended to intersect with the upper segments of each of the one or more front facelift suture path lines and the one or more side facelift suture path lines.

17. The facial invasive tissue treatment method, as recited in claim 1, wherein each of the one or more side facelift suture path lines is intersected with the one or more mid facelift suture path lines and the one or more front facelift suture path lines.

18. The facial invasive tissue treatment method, as recited in claim 17, wherein the upper segment of each of the one or more side facelift suture path lines is upwardly extended to intersect with upper segment of the one or more mid facelift suture path lines and the one or more front facelift suture path lines.

19. The facial invasive tissue treatment method, as recited in claim 1, further comprising a step of:
(iv) removing residual thread bodies of the first segment and the second segment of each of the invasive sutures implanted piercing out of a skin surface of the at least one half face of the user,
wherein each of the invasion sutures comprises a first needle, a second needle, an elongated flexible thread body, a first section of a plurality of frusto-conical shaped tissue engaging elements movably provided along the thread body to form a first segment, and a second section of a plurality of frusto-conical shaped tissue engage elements movably provided along the thread body to form a second segment, wherein the step (ii) further comprises steps of:
(ii-1) adjusting and tightening the upper segment and the lower segment of each of the invasive sutures implanted separately by slightly pulling and tightening an elongated end portion of each of the upper segment and lower segment extended out of the facial skin of the user; and
(ii-2) rubbing the facial skin and tissue of the user upwardly along the lower segment of each of the invasive sutures implanted until desired shape and condition are occurred by distributing the frusto-conically shaped tissue engaging elements to engage and tighten the facial skin and tissue of the user.

20. The facial invasive tissue treatment method, as recited in claim 19, wherein the step (ii) further comprises firstly adjusting and tightening one of the invasive sutures which is implanted in an upper position in the skin tissue of the user before adjusting and tightening another one of the invasive sutures which is implanted in a lower position below the one in the upper position.

* * * * *